US009603906B2

(12) United States Patent
Shaaltiel et al.

(10) Patent No.: US 9,603,906 B2
(45) **Date of Patent: *Mar. 28, 2017**

(54) INHALABLE LIQUID FORMULATIONS OF DNASE I

(71) Applicant: Protalix Ltd., Carmiel (IL)

(72) Inventors: Yoseph Shaaltiel, Timrat (IL); Uri Hanania, Carmiel (IL); Tali Kizhner, Yishuv Atzmon-Segev (IL); Yulia Matiuhin, Pardes Chana-Karkur (IL); Liat Fux, Kiryat-Motzkin (IL); Avidor Shulman, Rakefet (IL)

(73) Assignee: Protalix Ltd., Carmiel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/375,439

(22) PCT Filed: Jan. 31, 2013

(86) PCT No.: PCT/IL2013/050096

§ 371 (c)(1),
(2) Date: Jul. 30, 2014

(87) PCT Pub. No.: WO2013/114373

PCT Pub. Date: Aug. 8, 2013

(65) Prior Publication Data

US 2015/0010617 A1 Jan. 8, 2015

Related U.S. Application Data

(60) Provisional application No. 61/593,350, filed on Feb. 1, 2012, provisional application No. 61/593,676, filed on Feb. 1, 2012, provisional application No. 61/593,788, filed on Feb. 1, 2012.

(51) Int. Cl.

| | |
|---|---|
| *A61K 38/46* | (2006.01) |
| *C12N 9/22* | (2006.01) |
| *C12N 15/82* | (2006.01) |
| *A61K 9/00* | (2006.01) |
| *A61K 38/47* | (2006.01) |
| *A61K 33/06* | (2006.01) |
| *A61K 45/06* | (2006.01) |
| *A61K 9/14* | (2006.01) |
| *A61K 33/14* | (2006.01) |

(52) U.S. Cl.

CPC ............ *A61K 38/465* (2013.01); *A61K 9/007* (2013.01); *A61K 9/0075* (2013.01); *A61K 9/14* (2013.01); *A61K 33/06* (2013.01); *A61K 33/14* (2013.01); *A61K 38/47* (2013.01); *A61K 45/06* (2013.01); *C12N 9/22* (2013.01); *C12N 15/8221* (2013.01); *C12N 15/8257* (2013.01); *C12Y 301/21001* (2013.01); *C12Y 302/01052* (2013.01)

(58) Field of Classification Search

None

See application file for complete search history.

(56) References Cited

U.S. PATENT DOCUMENTS

| | | | |
|---|---|---|---|
| 3,991,761 | A | 11/1976 | Cocozza |
| 4,855,237 | A | 8/1989 | Morinaga et al. |
| 4,945,050 | A | 7/1990 | Sanford et al. |
| 5,035,237 | A | 7/1991 | Newell et al. |
| 5,316,931 | A | 5/1994 | Donson et al. |
| 5,351,683 | A | 10/1994 | Chiesi et al. |
| 5,352,461 | A | 10/1994 | Feldstein et al. |
| 5,437,270 | A | 8/1995 | Braithwaite |
| 5,447,150 | A | 9/1995 | Bacon |
| 5,458,135 | A | 10/1995 | Patton et al. |
| 5,469,750 | A | 11/1995 | Lloyd et al. |
| 5,503,144 | A | 4/1996 | Bacon |
| 5,503,852 | A | 4/1996 | Steiner et al. |
| 5,509,404 | A | 4/1996 | Lloyd et al. |
| 5,522,378 | A | 6/1996 | Ritson et al. |
| 5,522,385 | A | 6/1996 | Lloyd et al. |
| 5,525,519 | A | 6/1996 | Woiszwillo et al. |
| 5,554,730 | A | 9/1996 | Woiszwillo et al. |
| 5,578,709 | A | 11/1996 | Woiszwillo |
| 5,599,719 | A | 2/1997 | Woiszwillo et al. |
| 5,651,359 | A | 7/1997 | Bougamont et al. |
| 5,673,686 | A | 10/1997 | Villax et al. |
| 5,678,538 | A | 10/1997 | Drought |
| 5,693,507 | A | 12/1997 | Daniell et al. |
| 5,694,919 | A | 12/1997 | Rubsamen et al. |
| 5,735,263 | A | 4/1998 | Rubsamen et al. |
| 5,740,794 | A | 4/1998 | Smith et al. |

(Continued)

FOREIGN PATENT DOCUMENTS

| | | |
|---|---|---|
| AU | 775629 | 12/1999 |
| CA | 2298448 | 10/1999 |

(Continued)

OTHER PUBLICATIONS

Zijlstra et al., "Pharmacoeconomic review of recombinant human DNase in the management of cystic fibrosis", Expert Rev. Pharmacoeconomics Outcomes Res. 4(1), 49-59 (2004).*
Bosch et al., "N-Glycosylation of Plant-produced Recombinant Proteins", Current Pharmaceutical Design, 2013, 19, 5503-5512.*
Chen et al., "Involvement of the N- and C-terminal Fragments of Bovine Pancreatic Deoxyribonuclease in Active Protein Folding", Biochemistry, 2004, 43:10653-10663.*
International Preliminary Report on Patentability Dated Aug. 14, 2014 From the International Bureau of WIPO Re. PCT/IL2013/050096.
International Preliminary Report on Patentability Dated Aug. 14, 2014 From the International Bureau of WIPO Re. PCT/IL2013/050097.
International Preliminary Report on Patentability Dated Aug. 14, 2014 From the International Searching Authority Re. PCT/IL2013/050094.
International Search Report and the Written Opinion Dated Jun. 19, 2013 From the International Searching Authority Re. PCT/IL2013/050097.
International Search Report and the Written Opinion Dated Jul. 24, 2013 From the International Searching Authority Re. PCT/il2013/050094.

(Continued)

*Primary Examiner* — Suzanne M Noakes

(57) ABSTRACT

An inhalable pharmaceutical composition for pulmonary administration comprising human DNase I and a liquid carrier and, more particularly, but not exclusively, to methods, liquid pharmaceutical inhalation devices and systems for the therapeutic use thereof are provided.

19 Claims, 19 Drawing Sheets
(7 of 19 Drawing Sheet(s) Filed in Color)

(56) References Cited

U.S. PATENT DOCUMENTS

| | | | |
|---|---|---|---|
| 5,775,320 | A | 7/1998 | Patton et al. |
| 5,785,049 | A | 7/1998 | Smith et al. |
| 5,797,392 | A | 8/1998 | Keldmann et al. |
| 5,829,434 | A | 11/1998 | Ambrosio et al. |
| 5,840,279 | A | 11/1998 | Narodylo et al. |
| 5,855,564 | A | 1/1999 | Ruskewicz |
| 5,879,352 | A | 3/1999 | Filoso et al. |
| 5,881,719 | A | 3/1999 | Gottenauer et al. |
| 5,881,721 | A | 3/1999 | Bunce et al. |
| 5,934,272 | A | 8/1999 | Lloyd et al. |
| 5,960,792 | A | 10/1999 | Lloyd et al. |
| 5,976,574 | A | 11/1999 | Gordon |
| 5,981,719 | A | 11/1999 | Woiszwillo et al. |
| 5,985,248 | A | 11/1999 | Gordon et al. |
| 5,993,783 | A | 11/1999 | Eljamal et al. |
| 6,001,336 | A | 12/1999 | Gordon |
| 6,026,808 | A | 2/2000 | Armer et al. |
| 6,026,809 | A | 2/2000 | Abrams et al. |
| 6,040,498 | A | 3/2000 | Stomp et al. |
| 6,056,169 | A | 5/2000 | Bruna et al. |
| 6,071,497 | A | 6/2000 | Steiner et al. |
| 6,071,498 | A | 6/2000 | Narodylo et al. |
| 6,090,925 | A | 7/2000 | Woiszwillo et al. |
| 6,095,141 | A | 8/2000 | Armer et al. |
| 6,120,752 | A | 9/2000 | Oliver et al. |
| 6,132,394 | A | 10/2000 | Lankinen |
| 6,170,717 | B1 | 1/2001 | Di Giovanni et al. |
| 6,182,655 | B1 | 2/2001 | Keller et al. |
| 6,230,707 | B1 | 5/2001 | Hoerlin |
| 6,331,318 | B1 | 12/2001 | Milstein |
| 6,348,343 | B2 | 2/2002 | Lazarus et al. |
| 6,367,471 | B1 | 4/2002 | Genosar et al. |
| 6,391,607 | B1 | 5/2002 | Lazarus et al. |
| 6,391,638 | B1 | 5/2002 | Shaaltiel |
| 6,391,683 | B1 | 5/2002 | Chiu et al. |
| 6,397,838 | B1 | 6/2002 | Zimlich, Jr. et al. |
| 6,428,771 | B1 | 8/2002 | Steiner et al. |
| 6,458,387 | B1 | 10/2002 | Scott et al. |
| 6,482,391 | B1 | 11/2002 | Hills et al. |
| 6,488,027 | B1 | 12/2002 | Moulin |
| 6,521,260 | B1 | 2/2003 | Staniforth |
| 6,528,096 | B1 | 3/2003 | Musa et al. |
| 6,561,186 | B2 | 5/2003 | Casper et al. |
| 6,645,466 | B1 | 11/2003 | Keller et al. |
| 6,659,364 | B1 | 12/2003 | Humberstone et al. |
| 6,815,184 | B2 | 11/2004 | Stomp et al. |
| 6,901,926 | B2 | 6/2005 | Yamamoto et al. |
| 6,923,175 | B2 | 8/2005 | Poole et al. |
| 6,945,953 | B2 | 9/2005 | Wright |
| 6,962,151 | B1 | 11/2005 | Knoch et al. |
| 7,297,526 | B2 | 11/2007 | Shak |
| 7,407,785 | B2 | 8/2008 | Lazarus et al. |
| 7,432,308 | B2 | 10/2008 | Demeester et al. |
| 7,464,706 | B2 | 12/2008 | Steiner et al. |
| 7,763,610 | B2 | 7/2010 | Takeuchi et al. |
| 7,766,012 | B2 | 8/2010 | Scheuch et al. |
| 7,785,325 | B1 | 8/2010 | Milbank |
| 8,022,270 | B2 | 9/2011 | Dickey et al. |
| 2003/0094173 | A1 | 5/2003 | Burr et al. |
| 2004/0005660 | A1* | 1/2004 | Ludevid Mugica ................ C07K 14/425 435/69.1 |
| 2004/0077013 | A1 | 4/2004 | Ashkenazi et al. |
| 2004/0096403 | A1 | 5/2004 | Steiner et al. |
| 2004/0141961 | A1* | 7/2004 | Demeester ........... A61K 38/465 424/94.61 |
| 2005/0019925 | A1 | 1/2005 | Krummen et al. |
| 2005/0032211 | A1 | 2/2005 | Shaaltiel |
| 2006/0228347 | A1 | 10/2006 | Sunaga et al. |
| 2007/0196503 | A1 | 8/2007 | Wilson et al. |
| 2007/0259367 | A1 | 11/2007 | Ax et al. |
| 2008/0004561 | A1 | 1/2008 | Genkin et al. |
| 2010/0016386 | A1 | 1/2010 | Vocadlo et al. |
| 2010/0087477 | A1 | 4/2010 | Van Alten et al. |
| 2011/0033438 | A1 | 2/2011 | Bartoov et al. |
| 2011/0237631 | A1 | 9/2011 | Vocadlo et al. |
| 2011/0237782 | A1 | 9/2011 | Yang et al. |
| 2012/0046337 | A1 | 2/2012 | Liang et al. |
| 2015/0010527 | A1 | 1/2015 | Shaaltiel et al. |
| 2015/0024050 | A1 | 1/2015 | Shaaltiel et al. |

FOREIGN PATENT DOCUMENTS

| | | |
|---|---|---|
| CN | 1458161 | 11/2003 |
| EP | 0067553 | 12/1982 |
| EP | 0194809 | 9/1986 |
| EP | 0278667 | 8/1988 |
| EP | 0707862 | 4/1996 |
| EP | 0799067 | 10/1997 |
| EP | 0910421 | 4/1999 |
| EP | 1196146 | 4/2002 |
| EP | 1245244 | 10/2002 |
| EP | 1258264 | 11/2002 |
| EP | 1522325 | 4/2005 |
| EP | 2468870 | 6/2012 |
| GB | 2242134 | 9/1991 |
| GB | 2407042 | 4/2005 |
| JP | 63-014693 | 1/1988 |
| WO | WO 87/06261 | 10/1987 |
| WO | WO 90/07572 | 7/1990 |
| WO | WO 93/00951 | 1/1993 |
| WO | WO 93/07278 | 4/1993 |
| WO | WO 93/13713 | 7/1993 |
| WO | WO 93/25670 | 12/1993 |
| WO | WO 94/19042 | 9/1994 |
| WO | WO 94/22465 | 10/1994 |
| WO | WO 95/03846 | 2/1995 |
| WO | WO 96/09085 | 3/1996 |
| WO | WO 96/26278 | 8/1996 |
| WO | WO 96/32149 | 10/1996 |
| WO | WO 96/32152 | 10/1996 |
| WO | WO 97/00703 | 1/1997 |
| WO | WO 97/02061 | 1/1997 |
| WO | WO 97/20589 | 6/1997 |
| WO | WO 97/41833 | 11/1997 |
| WO | WO 98/29096 | 7/1998 |
| WO | WO 98/48873 | 11/1998 |
| WO | WO 98/52634 | 11/1998 |
| WO | WO 99/66903 | 12/1999 |
| WO | WO 99/67401 | 12/1999 |
| WO | WO 00/10541 | 3/2000 |
| WO | WO 00/35523 | 6/2000 |
| WO | WO 00/53158 | 9/2000 |
| WO | WO 01/07107 | 2/2001 |
| WO | WO 01/39823 | 6/2001 |
| WO | WO 01/49350 | 7/2001 |
| WO | WO 01/68169 | 9/2001 |
| WO | WO 01/78693 | 10/2001 |
| WO | WO 01/93933 | 12/2001 |
| WO | WO 02/10244 | 2/2002 |
| WO | WO 02/089880 | 11/2002 |
| WO | WO 03/035137 | 5/2003 |
| WO | WO 03/053501 | 7/2003 |
| WO | WO 03/095012 | 11/2003 |
| WO | WO 2004/003207 | 1/2004 |
| WO | WO 2004/024156 | 3/2004 |
| WO | WO 2004/026380 | 4/2004 |
| WO | WO 2004/041340 | 5/2004 |
| WO | WO 2004/082633 | 9/2004 |
| WO | WO 2004/091475 | 10/2004 |
| WO | WO 2005/056037 | 6/2005 |
| WO | WO 2005/080544 | 9/2005 |
| WO | WO 2006/006963 | 1/2006 |
| WO | WO 2006/040761 | 4/2006 |
| WO | WO 2007/010533 | 1/2007 |
| WO | WO 2008/039989 | 4/2008 |
| WO | WO 2008/064346 | 5/2008 |
| WO | WO 2008/135991 | 11/2008 |
| WO | WO 2009/123950 | 10/2009 |
| WO | WO 2009/152270 | 12/2009 |
| WO | WO 2009/152272 | 12/2009 |
| WO | WO 2011/004476 | 1/2011 |
| WO | WO 2011/053982 | 5/2011 |
| WO | WO 2012/149440 | 11/2012 |

(56) References Cited

FOREIGN PATENT DOCUMENTS

WO WO 2013/114371 8/2013
WO WO 2013/114373 8/2013
WO WO 2013/114374 8/2013

OTHER PUBLICATIONS

International Search Report and the Written Opinion Dated Jun. 28, 2013 From the International Searching Authority Re. Application No. PCT/IL2013/050096.
Chapman et al. "Delivery Characteristics and Patients' Handling of Two Single-Dose Dry-Powder Inhalers Used in COPD", International Journal of Chronic Obstructive and Pulmonary Diseases, COPD, 6: 353-363, 2011.
Erdeve et al. "Efficacy and Safety of Nebulized Recombinant Human DNase as Rescue Treatment for Persistant Atelelctasis in Newborns: Case-Series", Croatian Medical Journal, 48: 234-239, 2007.
Hunsaker et al. "*Homo sapiens* Deoxyribonuclease I (DNASE1), mRNA", Database NCBI GenBank, Version NM_005223.3, GI:58331227, Database Accession No. NM_05223, Feb. 9, 2013.
King et al. "Rheology of Cystic Fibrosis Sputum After in Vitro Treatment With Hypertonic Saline Alone and in Combination With Recombinant Human Deoxyribonuclease I", American Journal of Respiratory and Critical Care Medicine, 156: 173-177, 1997.
Lissens et al. "The Genetics of Male Infertility in Relation to Cystic Fibrosis", Bailliere's Clinical Pbstetrics and Gynaecology, 11(4/Chap.8b): 797-817, Dec. 1997.
Murray et al. "Codon Usage in Plant Genes", Nucleic Acids Research, 17(2): 477-498, 1989.
Nagata et al. "Tobacco By-2 Cells" The Present and Beyond, In Vitro Cellular & Developmental Biology—Plant, 40(2): 163-166, 2004. Abstract.
NBCI "IlomoSapiens Deoxyribonuclease I (DNASE1), mRNA", NCBI Database, Reference Sequence: NM 005223.3, Accession No. NM_005223, Jan. 23, 2012.
Pressler "Review of Recombinant Human Deoxyribonuclease (RhDNase) in the Management of Patients With Cystic Fibrosis", Biologics: Targets & Therapy, 2(4): 611-617, 2008.
Riordan et al. "Identification of the Cystic Fibrosis Gene: Cloning and Characterization of Complementary DNA", Science, 245(4922): 1066-1073, Sep. 8, 1989.
Rosenecker et al. "Airway Surface Liquid Contains Endogenous DNase Activity Which Can Be Activated by Exogenous Magnesium", European Journal of Medical Research, 14(7): 304-308, 2009. Abstract.
Sanders et al. "Role of Magnesium in the Failure of RhDNase Therapy in Patients With Cystic Fibrosis", Thorax, 61: 962-968, 2006.
Sardana et al. "Construction and Rapid Testing of Synthetic and Modified Toxin Gene Sequences CrylA (B&C) by Expression in Maize Endosperm Culture", Plant Cell Reports, 15(9): 677-681, 1996. Abstract.
Shak et al. "Recombinant Human DNase I Reduces the Vicosity of Cystic Fibrosis Sputum", Proc. Natl. Acad. Sci. USA, 87: 9188-9192, Dec. 1990.
Sojikul et al. "A Plant Signal Peptide-Hepatitis B Surface Antigen Fusion Protein With Enhanced Stbility and Immunogenicity Expressed in Plant Cells", Proc. Natl. Acad. Sci. USA, PNAS, XP002473534, 100(5): 2209-2214, Mar. 4, 2003. Abstract, p. 2209, Co1. 2, Lines 32-34.
Tian et al. "Auxin-Binding Protein 1 Does Not Bind Auxin Within the Endoplasmic Reticulum Despite This Being the Predominant Subcellular Location for This Hormone Receptor", The Journal of Biological Chemistry, XP055065756, 270(45): 26962-26969, Nov. 10, 1995. Abstract.
Weide et al. "Secretion of Functional Human Enzymes by Tetrahymena Thermophila", BMC Biotechnology, 6(19): 1-9, Mar. 16, 2006.
Zahm et al. "Dose-Dependent in Vitro Effect of Recombinant Human DNase on Rheological and Transport Properties of Cystic Fibrosis Respiratory Mucus", European Respiratory Journal, 8: 381-386, 1995.
Official Action Dated Aug. 18, 2016 From the US Patent and Trademark Office Re. U.S. Appl. No. 14/375,472.
Chrispeels et al. "The Production of Recombinant Glycoproteins with Defined Non-Immunogenic Glycans", in Owen MRL, Pen J. (eds) Transgenic Plants: A production System for Industrial and Pharmaceutical proteins, p. 99-113, 1996.
Giddings "Transgenic plants as protein factories", Current Opinion in Biotechnology,12(5): 450-454, Oct. 1, 2001.
Gonda et al. "Universality and Structure of the N-end Rule",The Journal of Biological Chemistry, 264(28): 16700-16712, Feb. 2, 1989.
Klode et al. "Expression and Subcellular Localization of Arabidopsis Thaliana Auxin-Binding Protein 1 (ABP1)",Journal of Plant Growth Regulation, 30(4): 416-424, Dec. 1, 2011.
Shimomura et al. "Structure of the Gene for an Auxin-Binding Protein and a Gene for 7SL RNA from Arabidopsis Thaliana", UniprotKB locus ABP1_ARATH, Dalase [Online], Accession No. P33487, 4 P., Nov. 30, 2010.
Worley et al. "Engineering in Vivo Instability of Firefly Luciferase and *Escherichia coli* β-Glucuronidase in Higher Plants Using Recognition Elements from the Ubiquitin Pathway", Plant Molecular Biology, 37(2): 337-347, May 1, 1998.
Official Action Dated Feb. 19, 2016 From the US Patent and Trademark Office Re. U.S. Appl. No. 14/375,485.
Bay et al. "Innovatoin in Drug Delivery by Inhalation", MannKind Corporation, 5 Pages, 2010.
Chan et al. "Spray Dried Powders and Powder Blends of Recombinant Human Deoxyribonuclease (rhDNase) for Aerosol Delivery", Pharmaceutical Research,14(4): 431-437, Apr. 1997.
Pilcer et al. "Formulation Strategy and Use of Excipients in Pulmonary Drug Delivery", International Journal of Pharmaceutics 392(1): 1-19, Mar. 17, 2010.
Communication Pursuant to Article 94(3) EPC Dated Jun. 3, 2016 From the European Patent Office Re. Application No. 13711558.0.
Varshaysky "The N-end Rule: Functions, Mysteries, Uses", Proc. Nat. Acad. Sci. USA, PNAS, 93(22): 12142-12149, Oct. 1996.
Whitelam "The Production of Recombinant Proteins in Plants", Journal of the Science of Food and Agriculture, 68(1): 1-9, 1995.
Official Action Dated Jan. 11, 2017 From the U.S. Patent and Trademark Office Re. U.S. Appl. No. 14/375,472. (17 pages).

* cited by examiner (a) -----------MRGMKLLGALLALAALLQGAVSLKIAAFNIQTFGETKMS
(b) MIVLSVGSASSSPIVVVFSVALLLFYFSETSLGLKIAAFNIQTFGETKMS
1 50

(a) NATLVSYIVQILSRYDIALVQEVRDSHLTAVGKLLDNLNQDAPDTYHYVV
(b) NATLVSYIVQILSRYDIALVQEVRDSHLTAVGKLLDNLNQDAPDTYHYVV
51 100

(a) SEPLGRNSYKERYLFVYRPDQVSAVDSYYYDDGCEPCGNDTFNREPAIVR
(b) SEPLGRNSYKERYLFVYRPDQVSAVDSYYYDDGCEPCGNDTFNREPAIVR
101 150

(a) FFSRFTEVREFAIVPLHAAPGDAVAEIDALYDVYLDVQEKWGLEDVMLMG
(b) FFSRFTEVREFAIVPLHAAPGDAVAEIDALYDVYLDVQEKWGLEDVMLMG
151 200

(a) DFNAGCSYVRPSQWSSIRLWTSPTFQWLIPDSADTTATPTHCAYDRIVVA
(b) DFNAGCSYVRPSQWSSIRLWTSPTFQWLIPDSADTTATPTHCAYDRIVVA
201 250

(a) GMLLRGAVVPDSALPFNFQAAYGLSDQLAQAISDHYPVEVMLK
(b) GMLLRGAVVPDSALPFNFQAAYGLSDQLAQAISDHYPVEVMLK
251 295

FIG. 1

FIG. 5B
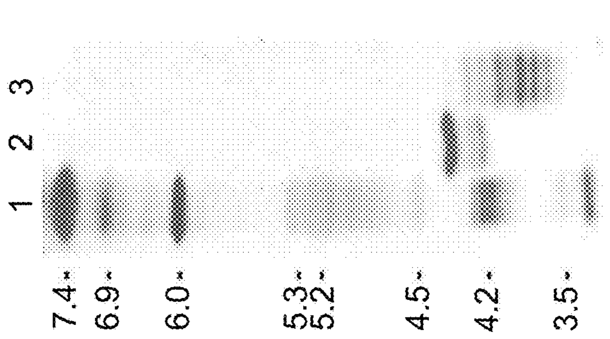
FIG. 5C
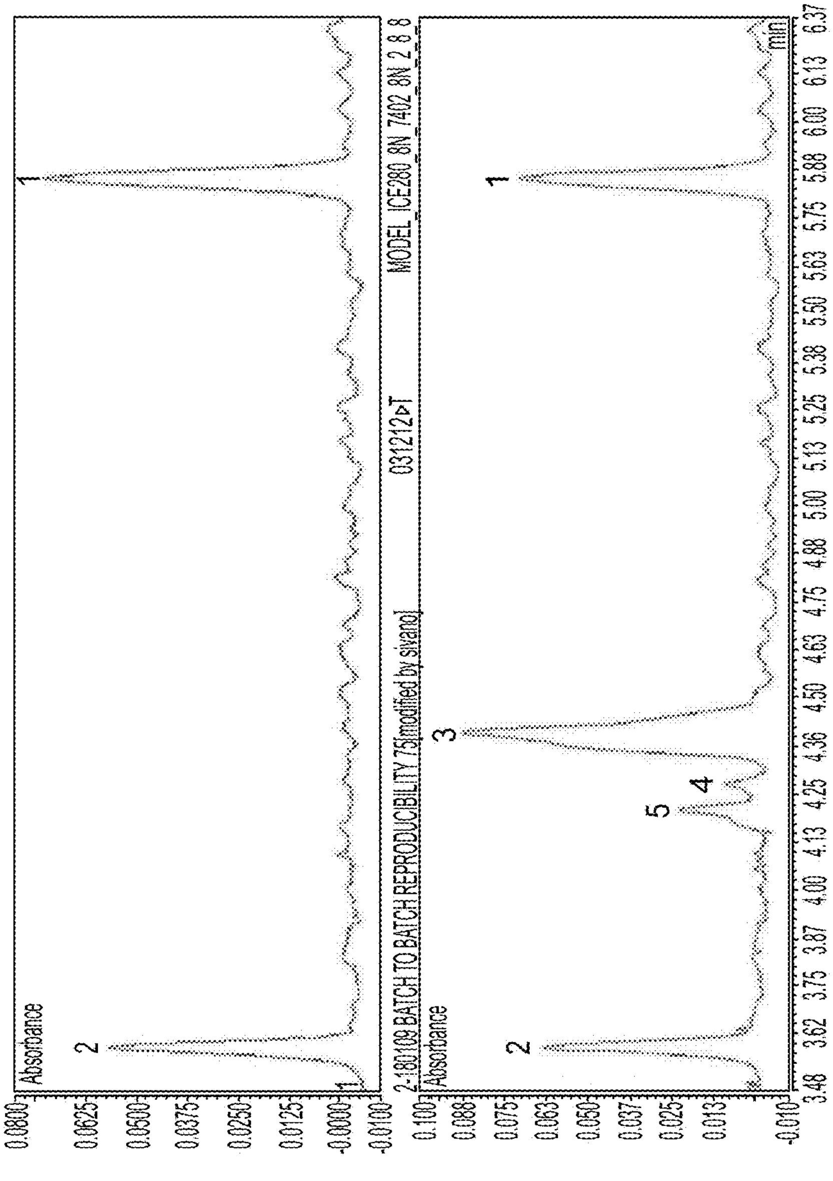
FIG. 5D

FIG. 6A
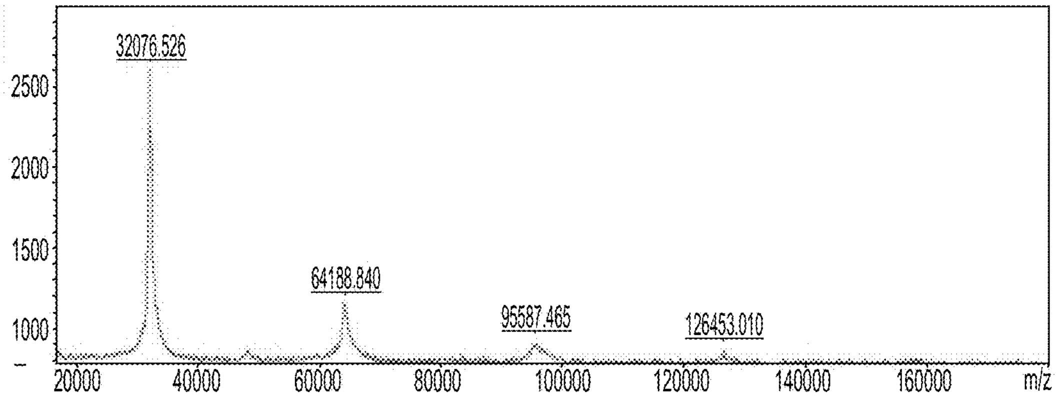
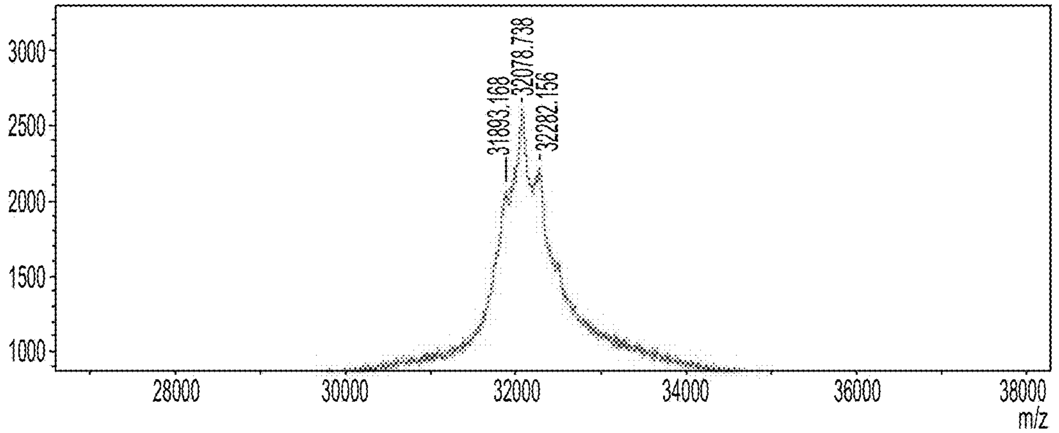
FIG. 6B
| | | | | | |
|---|---|---|---|---|---|
| 1 | GLKIAAFNIQ | TFGETKMSNA | TLVSYIVQIL | SRYDIALVQE | VRDSHLTAVG |
| 51 | KLLDNLNQDA | PDTYHYVVSE | PLGRNSYKER | YLFVYRPDQV | SAVDSYYYDD |
| 101 | GCEPCGNDTF | NREPAIVRFF | SRFTEVREFA | IVPLHAAPGD | AVAEIDALYD |
| 151 | VYLDVQEKWG | LEDVMLMGDF | NAGCSYVRPS | QWSSIRLWTS | PTFQWLIPDS |
| 201 | ADTTATPTHC | AYDRIVVAGM | LLRGAVVPDS | ALPFNFQAAY | GLSDQLAQAI |
| 251 | SDHYPVEVML | K | | | |
FIG. 7

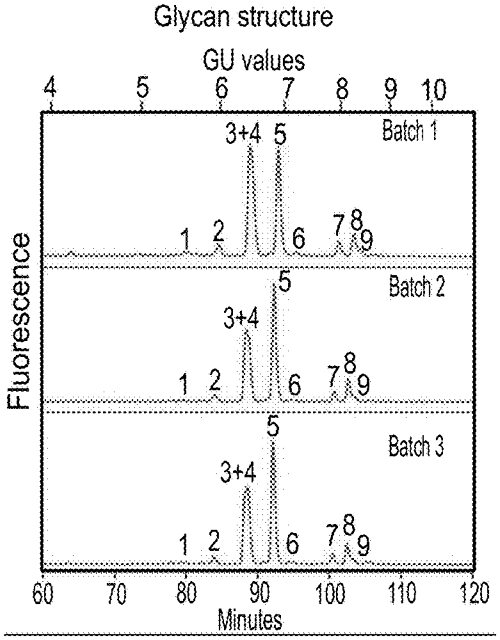
FIG. 8A
| Batch # | | Peak Number | 1 | 2 | | 3+4 | | | 5 | 6 | 7 | 8 | 9 |
|---|---|---|---|---|---|---|---|---|---|---|---|---|---|
| | | glycan formula | A1X | M4X | FcM3X | FcA[6]1X | M4XA1 | FcA[3]1X | FcA2X | hybrid | | | |
| | | Glycan structure |  |  | 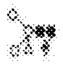 |  |  |  | 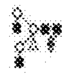 | UNDETERMINED | | | |
| | | calculated MW | 1268 | 1227 | 1211 | 1414 | 1430 | 1414 | 1618 | | | | |
| | | average GU value | 5.5 | 5.9 | | 6.4 | | | 6.9 | 7.2 | 8.1 | 8.3 | 8.5 |
| | 1 | %relative area | 2 | 4 | | 48 | | | 33 | 2 | 4 | 6 | 2 |
| | | Detected MW | 1268 | ND | 1211 | 1415 | 1431 | 1415 | 1618 | ND | ND | ND | ND |
| | 2 | %relative area | ND | 1 | 2 | 25 | 16 | | 43 | ND | 3 | 8 | 2 |
| | | Detected MW | ND | 1228 | ND | 1415 | ND | ND | 1618 | ND | ND | ND | ND |
| | 3 | %relative area | ND | 1 | 2 | 22 | 20 | | 42 | ND | 4 | 7 | 3 |
| | | Dtected MW | ND | 1228 | ND | 1415 | ND | 1415 | 1617 | ND | ND | ND | ND |
ND-not detected
FIG. 8B

SEQUENCE LISTING

```
<160> NUMBER OF SEQ ID NOS: 291

<210> SEQ ID NO 1
<211> LENGTH: 293
<212> TYPE: PRT
<213> ORGANISM: Artificial sequence
<220> FEATURE:
<223> OTHER INFORMATION: Plant recombinant human DNase I

<400> SEQUENCE: 1

Met Ile Val Leu Ser Val Gly Ser Ala Ser Ser Ser Pro Ile Val Val
1               5                   10                  15

Val Phe Ser Val Ala Leu Leu Leu Phe Tyr Phe Ser Glu Thr Ser Leu
            20                  25                  30

Gly Leu Lys Ile Ala Ala Phe Asn Ile Gln Thr Phe Gly Glu Thr Lys
        35                  40                  45

Met Ser Asn Ala Thr Leu Val Ser Tyr Ile Val Gln Ile Leu Ser Arg
    50                  55                  60

Tyr Asp Ile Ala Leu Val Gln Glu Val Arg Asp Ser His Leu Thr Ala
65                  70                  75                  80

Val Gly Lys Leu Leu Asp Asn Leu Asn Gln Asp Ala Pro Asp Thr Tyr
                85                  90                  95

His Tyr Val Val Ser Glu Pro Leu Gly Arg Asn Ser Tyr Lys Glu Arg
            100                 105                 110

Tyr Leu Phe Val Tyr Arg Pro Asp Gln Val Ser Ala Val Asp Ser Tyr
        115                 120                 125

Tyr Tyr Asp Asp Gly Cys Glu Pro Cys Gly Asn Asp Thr Phe Asn Arg
    130                 135                 140

Glu Pro Ala Ile Val Arg Phe Phe Ser Arg Phe Thr Glu Val Arg Glu
145                 150                 155                 160

Phe Ala Ile Val Pro Leu His Ala Ala Pro Gly Asp Ala Val Ala Glu
                165                 170                 175

Ile Asp Ala Leu Tyr Asp Val Tyr Leu Asp Val Gln Glu Lys Trp Gly
            180                 185                 190

Leu Glu Asp Val Met Leu Met Gly Asp Phe Asn Ala Gly Cys Ser Tyr
        195                 200                 205

Val Arg Pro Ser Gln Trp Ser Ser Ile Arg Leu Trp Thr Ser Pro Thr
    210                 215                 220

Phe Gln Trp Leu Ile Pro Asp Ser Ala Asp Thr Thr Ala Thr Pro Thr
225                 230                 235                 240

His Cys Ala Tyr Asp Arg Ile Val Val Ala Gly Met Leu Leu Arg Gly
                245                 250                 255

Ala Val Val Pro Asp Ser Ala Leu Pro Phe Asn Phe Gln Ala Ala Tyr
            260                 265                 270

Gly Leu Ser Asp Gln Leu Ala Gln Ala Ile Ser Asp His Tyr Pro Val
        275                 280                 285

Glu Val Met Leu Lys
    290
```

<210> SEQ ID NO 2
<211> LENGTH: 282
<212> TYPE: PRT
<213> ORGANISM: Homo sapiens

<400> SEQUENCE: 2

```
Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280
```

<210> SEQ ID NO 3
<211> LENGTH: 22
<212> TYPE: PRT
<213> ORGANISM: Homo sapiens

<400> SEQUENCE: 3

```
Met Arg Gly Met Lys Leu Leu Gly Ala Leu Leu Ala Leu Ala Ala Leu
1               5                   10                  15

Leu Gln Gly Ala Val Ser
            20
```

<210> SEQ ID NO 4

<211> LENGTH: 33
<212> TYPE: PRT
<213> ORGANISM: Artificial sequence
<220> FEATURE:
<223> OTHER INFORMATION: Arabidopsis derived ABPI endoplasmic reticulum targeting signal peptide

<400> SEQUENCE: 4

```
Met Ile Val Leu Ser Val Gly Ser Ala Ser Ser Ser Pro Ile Val Val
1               5                   10                  15

Val Phe Ser Val Ala Leu Leu Leu Phe Tyr Phe Ser Glu Thr Ser Leu
            20                  25                  30

Gly
```

<210> SEQ ID NO 5
<211> LENGTH: 261
<212> TYPE: PRT
<213> ORGANISM: Artificial sequence
<220> FEATURE:
<223> OTHER INFORMATION: Putative amino acid sequence of the purified, plant expressed rhDNase I

<400> SEQUENCE: 5

```
Gly Leu Lys Ile Ala Ala Phe Asn Ile Gln Thr Phe Gly Glu Thr Lys
1               5                   10                  15

Met Ser Asn Ala Thr Leu Val Ser Tyr Ile Val Gln Ile Leu Ser Arg
            20                  25                  30

Tyr Asp Ile Ala Leu Val Gln Glu Val Arg Asp Ser His Leu Thr Ala
        35                  40                  45

Val Gly Lys Leu Leu Asp Asn Leu Asn Gln Asp Ala Pro Asp Thr Tyr
    50                  55                  60

His Tyr Val Val Ser Glu Pro Leu Gly Arg Asn Ser Tyr Lys Glu Arg
65                  70                  75                  80

Tyr Leu Phe Val Tyr Arg Pro Asp Gln Val Ser Ala Val Asp Ser Tyr
                85                  90                  95

Tyr Tyr Asp Asp Gly Cys Glu Pro Cys Gly Asn Asp Thr Phe Asn Arg
            100                 105                 110

Glu Pro Ala Ile Val Arg Phe Phe Ser Arg Phe Thr Glu Val Arg Glu
        115                 120                 125

Phe Ala Ile Val Pro Leu His Ala Ala Pro Gly Asp Ala Val Ala Glu
    130                 135                 140

Ile Asp Ala Leu Tyr Asp Val Tyr Leu Asp Val Gln Glu Lys Trp Gly
145                 150                 155                 160

Leu Glu Asp Val Met Leu Met Gly Asp Phe Asn Ala Gly Cys Ser Tyr
                165                 170                 175

Val Arg Pro Ser Gln Trp Ser Ser Ile Arg Leu Trp Thr Ser Pro Thr
            180                 185                 190

Phe Gln Trp Leu Ile Pro Asp Ser Ala Asp Thr Thr Ala Thr Pro Thr
        195                 200                 205

His Cys Ala Tyr Asp Arg Ile Val Val Ala Gly Met Leu Leu Arg Gly
    210                 215                 220

Ala Val Val Pro Asp Ser Ala Leu Pro Phe Asn Phe Gln Ala Ala Tyr
225                 230                 235                 240

Gly Leu Ser Asp Gln Leu Ala Gln Ala Ile Ser Asp His Tyr Pro Val
                245                 250                 255

Glu Val Met Leu Lys
            260
```

<210> SEQ ID NO 6
<211> LENGTH: 260
<212> TYPE: PRT
<213> ORGANISM: Homo sapiens

<400> SEQUENCE: 6

```
Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260
```

<210> SEQ ID NO 7
<211> LENGTH: 261
<212> TYPE: PRT
<213> ORGANISM: Artificial sequence
<220> FEATURE:
<223> OTHER INFORMATION: Mature plant recombinant human DNaseI + G

<400> SEQUENCE: 7

```
Gly Leu Lys Ile Ala Ala Phe Asn Ile Gln Thr Phe Gly Glu Thr Lys
1               5                   10                  15

Met Ser Asn Ala Thr Leu Val Ser Tyr Ile Val Gln Ile Leu Ser Arg
            20                  25                  30

Tyr Asp Ile Ala Leu Val Gln Glu Val Arg Asp Ser His Leu Thr Ala
        35                  40                  45

Val Gly Lys Leu Leu Asp Asn Leu Asn Gln Asp Ala Pro Asp Thr Tyr
```

```
    50                  55                  60

His Tyr Val Val Ser Glu Pro Leu Gly Arg Asn Ser Tyr Lys Glu Arg
65                  70                  75                  80

Tyr Leu Phe Val Tyr Arg Pro Asp Gln Val Ser Ala Val Asp Ser Tyr
                85                  90                  95

Tyr Tyr Asp Asp Gly Cys Glu Pro Cys Gly Asn Asp Thr Phe Asn Arg
            100                 105                 110

Glu Pro Ala Ile Val Arg Phe Phe Ser Arg Phe Thr Glu Val Arg Glu
        115                 120                 125

Phe Ala Ile Val Pro Leu His Ala Ala Pro Gly Asp Ala Val Ala Glu
    130                 135                 140

Ile Asp Ala Leu Tyr Asp Val Tyr Leu Asp Val Gln Glu Lys Trp Gly
145                 150                 155                 160

Leu Glu Asp Val Met Leu Met Gly Asp Phe Asn Ala Gly Cys Ser Tyr
                165                 170                 175

Val Arg Pro Ser Gln Trp Ser Ser Ile Arg Leu Trp Thr Ser Pro Thr
            180                 185                 190

Phe Gln Trp Leu Ile Pro Asp Ser Ala Asp Thr Thr Ala Thr Pro Thr
        195                 200                 205

His Cys Ala Tyr Asp Arg Ile Val Val Ala Gly Met Leu Leu Arg Gly
    210                 215                 220

Ala Val Val Pro Asp Ser Ala Leu Pro Phe Asn Phe Gln Ala Ala Tyr
225                 230                 235                 240

Gly Leu Ser Asp Gln Leu Ala Gln Ala Ile Ser Asp His Tyr Pro Val
                245                 250                 255

Glu Val Met Leu Lys
            260


<210> SEQ ID NO 8
<211> LENGTH: 293
<212> TYPE: PRT
<213> ORGANISM: Artificial sequence
<220> FEATURE:
<223> OTHER INFORMATION: Plant recombinant human DNase I

<400> SEQUENCE: 8

Met Ile Val Leu Ser Val Gly Ser Ala Ser Ser Ser Pro Ile Val Val
1               5                   10                  15

Val Phe Ser Val Ala Leu Leu Leu Phe Tyr Phe Ser Glu Thr Ser Leu
            20                  25                  30

Gly Leu Lys Ile Ala Ala Phe Asn Ile Gln Thr Phe Gly Glu Thr Lys
        35                  40                  45

Met Ser Asn Ala Thr Leu Val Ser Tyr Ile Val Gln Ile Leu Ser Arg
    50                  55                  60

Tyr Asp Ile Ala Leu Val Gln Glu Val Arg Asp Ser His Leu Thr Ala
65                  70                  75                  80

Val Gly Lys Leu Leu Asp Asn Leu Asn Gln Asp Ala Pro Asp Thr Tyr
                85                  90                  95

His Tyr Val Val Ser Glu Pro Leu Gly Arg Asn Ser Tyr Lys Glu Arg
            100                 105                 110

Tyr Leu Phe Val Tyr Arg Pro Asp Gln Val Ser Ala Val Asp Ser Tyr
        115                 120                 125

Tyr Tyr Asp Asp Gly Cys Glu Pro Cys Gly Asn Asp Thr Phe Asn Arg
    130                 135                 140

Glu Pro Ala Ile Val Arg Phe Phe Ser Arg Phe Thr Glu Val Arg Glu
```

-continued

```
145                 150                 155                 160

Phe Ala Ile Val Pro Leu His Ala Ala Pro Gly Asp Ala Val Ala Glu
                165                 170                 175

Ile Asp Ala Leu Tyr Asp Val Tyr Leu Asp Val Gln Glu Lys Trp Gly
            180                 185                 190

Leu Glu Asp Val Met Leu Met Gly Asp Phe Asn Ala Gly Cys Ser Tyr
        195                 200                 205

Val Arg Pro Ser Gln Trp Ser Ser Ile Arg Leu Trp Thr Ser Pro Thr
    210                 215                 220

Phe Gln Trp Leu Ile Pro Asp Ser Ala Asp Thr Thr Ala Thr Pro Thr
225                 230                 235                 240

His Cys Ala Tyr Asp Arg Ile Val Val Ala Gly Met Leu Leu Arg Gly
                245                 250                 255

Ala Val Val Pro Asp Ser Ala Leu Pro Phe Asn Phe Gln Ala Ala Tyr
            260                 265                 270

Gly Leu Ser Asp Gln Leu Ala Gln Ala Ile Ser Asp His Tyr Pro Val
        275                 280                 285

Glu Val Met Leu Lys
    290


<210> SEQ ID NO 9
<211> LENGTH: 786
<212> TYPE: DNA
<213> ORGANISM: Artificial sequence
<220> FEATURE:
<223> OTHER INFORMATION: Coding sequence of the recombinant DNase I
      without the leader sequence

<400> SEQUENCE: 9

cttaaaatcg ctgctttcaa catccaaact ttcggagaga ctaagatgtc taacgctact      60

cttgtgtcct acatcgttca gattctctcc agatacgata ttgctcttgt tcaggaagtt     120

agggattctc accttactgc tgtgggaaag cttcttgata acctcaatca ggatgctcca     180

gatacttacc actacgttgt gtctgaacca cttggaagaa actcctacaa agagcgttac     240

ctctttgttt accgtccaga tcaagtttct gctgtggatt cctactacta cgatgatgga     300

tgtgagccat gcggaaacga tactttcaat agagagccag ctatcgttcg ttttttcagt     360

aggttcactg aagttcgtga gtttgctatt gtgccacttc atgctgctcc aggtgatgct     420

gttgctgaga ttgatgctct ctacgatgtg taccttgatg ttcaagagaa gtggggattg     480

gaggatgtta tgctcatggg agatttcaat gctggatgct cttatgttag gccatctcag     540

tggtcatcta ttaggctttg gacttcccca actttccaat ggcttatccc agattccgct     600

gatacaactg ctactccaac tcattgtgct tacgatagga ttgtggtggc tggaatgctt     660

cttagaggtg ctgttgttcc agattctgct ctcccattca atttccaagc tgcttacgga     720

ctttctgatc aacttgctca ggctatttct gatcactacc cagttgaggt gatgttgaag     780

tgatga                                                                786


<210> SEQ ID NO 10
<211> LENGTH: 99
<212> TYPE: DNA
<213> ORGANISM: Artificial sequence
<220> FEATURE:
<223> OTHER INFORMATION: Coding sequence of polypeptide of ABPI leader
      signal

<400> SEQUENCE: 10
```

atgattgtgc tttctgtggg atctgcttct tcttctccaa ttgtggtggt gttctctgtg 60
gctcttcttc ttttctactt ctctgagact tctcttggc 99

<210> SEQ ID NO 11
<211> LENGTH: 849
<212> TYPE: DNA
<213> ORGANISM: Homo sapiens

<400> SEQUENCE: 11
atgaggggca tgaagctgct gggggcgctg ctggcactgg cggccctact gcagggggcc 60
gtgtccctga agatcgcagc cttcaacatc cagacatttg gggagaccaa gatgtccaat 120
gccaccctcg tcagctacat tgtgcagatc ctgagccgct atgacatcgc cctggtccag 180
gaggtcagag acagccacct gactgccgtg gggaagctgc tggacaacct caatcaggat 240
gcaccagaca cctatcacta cgtggtcagt gagccactgg gacggaacag ctataaggag 300
cgctacctgt tcgtgtacag gcctgaccag gtgtctgcgg tggacagcta ctactacgat 360
gatggctgcg agccctgcgg gaacgacacc ttcaaccgag agccagccat tgtcaggttc 420
ttctcccggt tcacagaggt cagggagttt gccattgttc ccctgcatgc ggccccgggg 480
gacgcagtag ccgagatcga cgctctctat gacgtctacc tggatgtcca agagaaatgg 540
ggcttggagg acgtcatgtt gatgggcgac ttcaatgcgg gctgcagcta tgtgagaccc 600
tcccagtggt catccatccg cctgtggaca agccccacct tccagtggct gatccccgac 660
agcgctgaca ccacagctac acccacgcac tgtgcctatg acaggatcgt ggttgcaggg 720
atgctgctcc gaggcgccgt tgttcccgac tcggctcttc cctttaactt ccaggctgcc 780
tatggcctga gtgaccaact ggcccaagcc atcagtgacc actatccagt ggaggtgatg 840
ctgaagtga 849

<210> SEQ ID NO 12
<211> LENGTH: 885
<212> TYPE: DNA
<213> ORGANISM: Artificial sequence
<220> FEATURE:
<223> OTHER INFORMATION: Coding sequence of rhDNase I (ABPI+DNase I)

<400> SEQUENCE: 12
atgattgtgc tttctgtggg atctgcttct tcttctccaa ttgtggtggt gttctctgtg 60
gctcttcttc ttttctactt ctctgagact tctcttggcc ttaaaatcgc tgctttcaac 120
atccaaactt tcggagagac taagatgtct aacgctactc ttgtgtccta catcgttcag 180
attctctcca gatacgatat tgctcttgtt caggaagtta gggattctca ccttactgct 240
gtgggaaagc ttcttgataa cctcaatcag gatgctccag atacttacca ctacgttgtg 300
tctgaaccac ttggaagaaa ctcctacaaa gagcgttacc tctttgttta ccgtccagat 360
caagtttctg ctgtggattc ctactactac gatgatggat gtgagccatg cggaaacgat 420
actttcaata gagagccagc tatcgttcgt tttttcagta ggttcactga agttcgtgag 480
tttgctattg tgccacttca tgctgctcca ggtgatgctg ttgctgagat tgatgctctc 540
tacgatgtgt accttgatgt tcaagagaag tggggattgg aggatgttat gctcatggga 600
gatttcaatg ctggatgctc ttatgttagg ccatctcagt ggtcatctat taggctttgg 660
acttccccaa ctttccaatg gcttatccca gattccgctg atacaactgc tactccaact 720
cattgtgctt acgataggat tgtggtggct ggaatgcttc ttagaggtgc tgttgttcca 780
gattctgctc tcccattcaa tttccaagct gcttacggac tttctgatca acttgctcag 840

```
gctatttctg atcactaccc agttgaggtg atgttgaagt gatga                    885


<210> SEQ ID NO 13
<211> LENGTH: 6
<212> TYPE: PRT
<213> ORGANISM: Artificial sequence
<220> FEATURE:
<223> OTHER INFORMATION: Endoplasmic reticulum retention signal SEKDEL

<400> SEQUENCE: 13

Ser Glu Lys Asp Glu Leu
1               5


<210> SEQ ID NO 14
<211> LENGTH: 18
<212> TYPE: DNA
<213> ORGANISM: Artificial sequence
<220> FEATURE:
<223> OTHER INFORMATION: Coding sequence of SEKDEL (ER retention signal)

<400> SEQUENCE: 14

tctgagaagg atgagctt                                                   18


<210> SEQ ID NO 15
<211> LENGTH: 7
<212> TYPE: PRT
<213> ORGANISM: Artificial sequence
<220> FEATURE:
<223> OTHER INFORMATION: Vacuole targeting signal peptide GLLVDTM

<400> SEQUENCE: 15

Gly Leu Leu Val Asp Thr Met
1               5


<210> SEQ ID NO 16
<211> LENGTH: 21
<212> TYPE: DNA
<213> ORGANISM: Artificial sequence
<220> FEATURE:
<223> OTHER INFORMATION: Coding sequence for vacuole targeting signal
      peptide GLLVDTM

<400> SEQUENCE: 16

ggacttcttg ttgatactat g                                               21


<210> SEQ ID NO 17
<211> LENGTH: 16
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 17

Gly Leu Lys Ile Ala Ala Phe Asn Ile Gln Thr Phe Gly Glu Thr Lys
1               5                   10                  15


<210> SEQ ID NO 18
<211> LENGTH: 6
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 18
```

Leu Lys Ile Ala Ala Phe
1 5

<210> SEQ ID NO 19
<211> LENGTH: 11
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 19

Leu Lys Ile Ala Ala Phe Asn Ile Gln Thr Phe
1 5 10

<210> SEQ ID NO 20
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 20

Leu Lys Ile Ala Ala Phe Asn Ile Gln Thr Phe Gly Glu Thr Lys
1 5 10 15

<210> SEQ ID NO 21
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 21

Lys Ile Ala Ala Phe Asn Ile Gln Thr Phe Gly Glu Thr Lys
1 5 10

<210> SEQ ID NO 22
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 22

Ile Ala Ala Phe Asn Ile Gln
1 5

<210> SEQ ID NO 23
<211> LENGTH: 9
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 23

Ile Ala Ala Phe Asn Ile Gln Thr Phe
1 5

<210> SEQ ID NO 24
<211> LENGTH: 10
<212> TYPE: PRT
<213> ORGANISM: Artificial sequence
<220> FEATURE:

```
<223> OTHER INFORMATION: A peptide identified following digestion with
      Trypsin and Chymotrypsin of the plant-expressed rh DNase I

<400> SEQUENCE: 24

Ile Ala Ala Phe Asn Ile Gln Thr Phe Gly
1               5                   10


<210> SEQ ID NO 25
<211> LENGTH: 13
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 25

Ile Ala Ala Phe Asn Ile Gln Thr Phe Gly Glu Thr Lys
1               5                   10


<210> SEQ ID NO 26
<211> LENGTH: 11
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 26

Ala Phe Asn Ile Gln Thr Phe Gly Glu Thr Lys
1               5                   10


<210> SEQ ID NO 27
<211> LENGTH: 10
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 27

Phe Asn Ile Gln Thr Phe Gly Glu Thr Lys
1               5                   10


<210> SEQ ID NO 28
<211> LENGTH: 5
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 28

Asn Ile Gln Thr Phe
1               5


<210> SEQ ID NO 29
<211> LENGTH: 9
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 29

Asn Ile Gln Thr Phe Gly Glu Thr Lys
1               5
```

<210> SEQ ID NO 30
<211> LENGTH: 7
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 30

Gln Thr Phe Gly Glu Thr Lys
1 5

<210> SEQ ID NO 31
<211> LENGTH: 6
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 31

Thr Phe Gly Glu Thr Lys
1 5

<210> SEQ ID NO 32
<211> LENGTH: 9
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 32

Met Ser Asn Ala Thr Leu Val Ser Tyr
1 5

<210> SEQ ID NO 33
<211> LENGTH: 16
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 33

Met Ser Asn Ala Thr Leu Val Ser Tyr Ile Val Gln Ile Leu Ser Arg
1 5 10 15

<210> SEQ ID NO 34
<211> LENGTH: 12
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 34

Thr Leu Val Ser Tyr Ile Val Gln Ile Leu Ser Arg
1 5 10

<210> SEQ ID NO 35
<211> LENGTH: 10
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 35

```
Val Ser Tyr Ile Val Gln Ile Leu Ser Arg
1               5                   10


<210> SEQ ID NO 36
<211> LENGTH: 7
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 36

Ile Val Gln Ile Leu Ser Arg
1               5


<210> SEQ ID NO 37
<211> LENGTH: 8
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 37

Ile Val Gln Ile Leu Ser Arg Tyr
1               5


<210> SEQ ID NO 38
<211> LENGTH: 6
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 38

Val Gln Ile Leu Ser Arg
1               5


<210> SEQ ID NO 39
<211> LENGTH: 5
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 39

Gln Ile Leu Ser Arg
1               5


<210> SEQ ID NO 40
<211> LENGTH: 12
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 40

Ser Arg Tyr Asp Ile Ala Leu Val Gln Glu Val Arg
1               5                   10


<210> SEQ ID NO 41
<211> LENGTH: 6
<212> TYPE: PRT
<213> ORGANISM: Artificial sequence
```

```
<220> FEATURE:
<223> OTHER INFORMATION: A peptide identified following digestion with
      Trypsin and Chymotrypsin of the plant-expressed rh DNase I

<400> SEQUENCE: 41

Tyr Asp Ile Ala Leu Val
1               5


<210> SEQ ID NO 42
<211> LENGTH: 7
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 42

Tyr Asp Ile Ala Leu Val Gln
1               5


<210> SEQ ID NO 43
<211> LENGTH: 9
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 43

Tyr Asp Ile Ala Leu Val Gln Glu Val
1               5


<210> SEQ ID NO 44
<211> LENGTH: 10
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 44

Tyr Asp Ile Ala Leu Val Gln Glu Val Arg
1               5                   10


<210> SEQ ID NO 45
<211> LENGTH: 11
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 45

Tyr Asp Ile Ala Leu Val Gln Glu Val Arg Asp
1               5                   10


<210> SEQ ID NO 46
<211> LENGTH: 14
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 46

Tyr Asp Ile Ala Leu Val Gln Glu Val Arg Asp Ser His Leu
1               5                   10
```

```
<210> SEQ ID NO 47
<211> LENGTH: 19
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 47

Tyr Asp Ile Ala Leu Val Gln Glu Val Arg Asp Ser His Leu Thr Ala
1               5                   10                  15

Val Gly Lys


<210> SEQ ID NO 48
<211> LENGTH: 6
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 48

Asp Ile Ala Leu Val Gln
1               5


<210> SEQ ID NO 49
<211> LENGTH: 9
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 49

Asp Ile Ala Leu Val Gln Glu Val Arg
1               5


<210> SEQ ID NO 50
<211> LENGTH: 18
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 50

Asp Ile Ala Leu Val Gln Glu Val Arg Asp Ser His Leu Thr Ala Val
1               5                   10                  15

Gly Lys


<210> SEQ ID NO 51
<211> LENGTH: 8
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 51

Ile Ala Leu Val Gln Glu Val Arg
1               5


<210> SEQ ID NO 52
<211> LENGTH: 6
<212> TYPE: PRT
<213> ORGANISM: Artificial sequence
```

<220> FEATURE:
<223> OTHER INFORMATION: A peptide identified following digestion with
Trypsin and Chymotrypsin of the plant-expressed rh DNase I

<400> SEQUENCE: 52

Ala Leu Val Gln Glu Val
1 5

<210> SEQ ID NO 53
<211> LENGTH: 7
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 53

Ala Leu Val Gln Glu Val Arg
1 5

<210> SEQ ID NO 54
<211> LENGTH: 6
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 54

Leu Val Gln Glu Val Arg
1 5

<210> SEQ ID NO 55
<211> LENGTH: 5
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 55

Val Gln Glu Val Arg
1 5

<210> SEQ ID NO 56
<211> LENGTH: 12
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 56

Glu Val Arg Asp Ser His Leu Thr Ala Val Gly Lys
1 5 10

<210> SEQ ID NO 57
<211> LENGTH: 10
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 57

Arg Asp Ser His Leu Thr Ala Val Gly Lys
1 5 10

<210> SEQ ID NO 58
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 58

```
Asp Ser His Leu Thr Ala Val Gly
1               5
```

<210> SEQ ID NO 59
<211> LENGTH: 9
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 59

```
Asp Ser His Leu Thr Ala Val Gly Lys
1               5
```

<210> SEQ ID NO 60
<211> LENGTH: 32
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 60

```
Asp Ser His Leu Thr Ala Val Gly Lys Leu Leu Asp Asn Leu Asn Gln
1               5                   10                  15

Asp Ala Pro Asp Thr Tyr His Tyr Val Val Ser Glu Pro Leu Gly Arg
            20                  25                  30
```

<210> SEQ ID NO 61
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 61

```
Ser His Leu Thr Ala Val Gly Lys
1               5
```

<210> SEQ ID NO 62
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 62

```
Lys Leu Leu Asp Asn Leu Asn Gln Asp Ala Pro Asp Thr Tyr
1               5                   10
```

<210> SEQ ID NO 63
<211> LENGTH: 6
<212> TYPE: PRT
<213> ORGANISM: Artificial sequence
<220> FEATURE:

<223> OTHER INFORMATION: A peptide identified following digestion with
      Trypsin and Chymotrypsin of the plant-expressed rh DNase I

<400> SEQUENCE: 63

Leu Leu Asp Asn Leu Asn
1               5

<210> SEQ ID NO 64
<211> LENGTH: 7
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 64

Leu Leu Asp Asn Leu Asn Gln
1               5

<210> SEQ ID NO 65
<211> LENGTH: 8
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 65

Leu Leu Asp Asn Leu Asn Gln Asp
1               5

<210> SEQ ID NO 66
<211> LENGTH: 9
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 66

Leu Leu Asp Asn Leu Asn Gln Asp Ala
1               5

<210> SEQ ID NO 67
<211> LENGTH: 12
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 67

Leu Leu Asp Asn Leu Asn Gln Asp Ala Pro Asp Thr
1               5                   10

<210> SEQ ID NO 68
<211> LENGTH: 13
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 68

Leu Leu Asp Asn Leu Asn Gln Asp Ala Pro Asp Thr Tyr
1               5                   10

<210> SEQ ID NO 69
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 69

Leu Leu Asp Asn Leu Asn Gln Asp Ala Pro Asp Thr Tyr His
1 5 10

<210> SEQ ID NO 70
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 70

Leu Leu Asp Asn Leu Asn Gln Asp Ala Pro Asp Thr Tyr His Tyr
1 5 10 15

<210> SEQ ID NO 71
<211> LENGTH: 23
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 71

Leu Leu Asp Asn Leu Asn Gln Asp Ala Pro Asp Thr Tyr His Tyr Val
1 5 10 15

Val Ser Glu Pro Leu Gly Arg
20

<210> SEQ ID NO 72
<211> LENGTH: 27
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 72

Leu Leu Asp Asn Leu Asn Gln Asp Ala Pro Asp Thr Tyr His Tyr Val
1 5 10 15

Val Ser Glu Pro Leu Gly Arg Asn Ser Tyr Lys
20 25

<210> SEQ ID NO 73
<211> LENGTH: 29
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 73

Leu Leu Asp Asn Leu Asn Gln Asp Ala Pro Asp Thr Tyr His Tyr Val
1 5 10 15

Val Ser Glu Pro Leu Gly Arg Asn Ser Tyr Lys Glu Arg
20 25

```
<210> SEQ ID NO 74
<211> LENGTH: 15
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 74

Leu Asp Asn Leu Asn Gln Asp Ala Pro Asp Thr Tyr His Tyr Val
1               5                   10                  15


<210> SEQ ID NO 75
<211> LENGTH: 11
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 75

Asp Asn Leu Asn Gln Asp Ala Pro Asp Thr Tyr
1               5                   10


<210> SEQ ID NO 76
<211> LENGTH: 21
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 76

Asp Asn Leu Asn Gln Asp Ala Pro Asp Thr Tyr His Tyr Val Val Ser
1               5                   10                  15

Glu Pro Leu Gly Arg
            20


<210> SEQ ID NO 77
<211> LENGTH: 20
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 77

Asn Leu Asn Gln Asp Ala Pro Asp Thr Tyr His Tyr Val Val Ser Glu
1               5                   10                  15

Pro Leu Gly Arg
            20


<210> SEQ ID NO 78
<211> LENGTH: 19
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 78

Leu Asn Gln Asp Ala Pro Asp Thr Tyr His Tyr Val Val Ser Glu Pro
1               5                   10                  15

Leu Gly Arg


<210> SEQ ID NO 79
```

<211> LENGTH: 17
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 79

Gln Asp Ala Pro Asp Thr Tyr His Tyr Val Val Ser Glu Pro Leu Gly
1 5 10 15

Arg

<210> SEQ ID NO 80
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 80

Asp Ala Pro Asp Thr Tyr His Tyr Val Val Ser Glu Pro Leu Gly Arg
1 5 10 15

<210> SEQ ID NO 81
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 81

Ala Pro Asp Thr Tyr His Tyr
1 5

<210> SEQ ID NO 82
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 82

Ala Pro Asp Thr Tyr His Tyr Val Val Ser Glu Pro Leu Gly Arg
1 5 10 15

<210> SEQ ID NO 83
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 83

Pro Asp Thr Tyr His Tyr Val Val Ser Glu Pro Leu Gly Arg
1 5 10

<210> SEQ ID NO 84
<211> LENGTH: 13
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 84

Asp Thr Tyr His Tyr Val Val Ser Glu Pro Leu Gly Arg
1 5 10

<210> SEQ ID NO 85
<211> LENGTH: 12
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 85

Thr Tyr His Tyr Val Val Ser Glu Pro Leu Gly Arg
1 5 10

<210> SEQ ID NO 86
<211> LENGTH: 6
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 86

His Tyr Val Val Ser Glu
1 5

<210> SEQ ID NO 87
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 87

His Tyr Val Val Ser Glu Pro Leu
1 5

<210> SEQ ID NO 88
<211> LENGTH: 9
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 88

His Tyr Val Val Ser Glu Pro Leu Gly
1 5

<210> SEQ ID NO 89
<211> LENGTH: 10
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 89

His Tyr Val Val Ser Glu Pro Leu Gly Arg
1 5 10

<210> SEQ ID NO 90
<211> LENGTH: 11
<212> TYPE: PRT

```
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 90

His Tyr Val Val Ser Glu Pro Leu Gly Arg Asn
1               5                   10


<210> SEQ ID NO 91
<211> LENGTH: 14
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 91

His Tyr Val Val Ser Glu Pro Leu Gly Arg Asn Ser Tyr Lys
1               5                   10


<210> SEQ ID NO 92
<211> LENGTH: 9
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 92

Tyr Val Val Ser Glu Pro Leu Gly Arg
1               5


<210> SEQ ID NO 93
<211> LENGTH: 6
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 93

Val Val Ser Glu Pro Leu
1               5


<210> SEQ ID NO 94
<211> LENGTH: 9
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 94

Val Val Ser Glu Pro Leu Gly Arg Asn
1               5


<210> SEQ ID NO 95
<211> LENGTH: 12
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 95

Val Val Ser Glu Pro Leu Gly Arg Asn Ser Tyr Lys
1               5                   10
```

<210> SEQ ID NO 96
<211> LENGTH: 5
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 96

Glu Arg Tyr Leu Phe
1 5

<210> SEQ ID NO 97
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 97

Tyr Leu Phe Val Tyr Arg Pro Asp
1 5

<210> SEQ ID NO 98
<211> LENGTH: 10
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 98

Tyr Leu Phe Val Tyr Arg Pro Asp Gln Val
1 5 10

<210> SEQ ID NO 99
<211> LENGTH: 11
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 99

Tyr Leu Phe Val Tyr Arg Pro Asp Gln Val Ser
1 5 10

<210> SEQ ID NO 100
<211> LENGTH: 12
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 100

Tyr Leu Phe Val Tyr Arg Pro Asp Gln Val Ser Ala
1 5 10

<210> SEQ ID NO 101
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 101

Tyr Leu Phe Val Tyr Arg Pro Asp Gln Val Ser Ala Val Asp
1 5 10

<210> SEQ ID NO 102
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 102

Tyr Leu Phe Val Tyr Arg Pro Asp Gln Val Ser Ala Val Asp Ser Tyr
1 5 10 15

<210> SEQ ID NO 103
<211> LENGTH: 17
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 103

Tyr Leu Phe Val Tyr Arg Pro Asp Gln Val Ser Ala Val Asp Ser Tyr
1 5 10 15

Tyr

<210> SEQ ID NO 104
<211> LENGTH: 19
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 104

Tyr Leu Phe Val Tyr Arg Pro Asp Gln Val Ser Ala Val Asp Ser Tyr
1 5 10 15

Tyr Tyr Asp

<210> SEQ ID NO 105
<211> LENGTH: 20
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 105

Tyr Leu Phe Val Tyr Arg Pro Asp Gln Val Ser Ala Val Asp Ser Tyr
1 5 10 15

Tyr Tyr Asp Asp
20

<210> SEQ ID NO 106
<211> LENGTH: 21
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 106

Tyr Leu Phe Val Tyr Arg Pro Asp Gln Val Ser Ala Val Asp Ser Tyr
1 5 10 15

Tyr Tyr Asp Asp Gly
20

<210> SEQ ID NO 107
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 107

Leu Phe Val Tyr Arg Pro Asp Gln Val Ser Ala Val Asp Ser Tyr
1 5 10 15

<210> SEQ ID NO 108
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 108

Leu Phe Val Tyr Arg Pro Asp Gln Val Ser Ala Val Asp Ser Tyr Tyr
1 5 10 15

<210> SEQ ID NO 109
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 109

Phe Val Tyr Arg Pro Asp Gln Val Ser Ala Val Asp Ser Tyr
1 5 10

<210> SEQ ID NO 110
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 110

Phe Val Tyr Arg Pro Asp Gln Val Ser Ala Val Asp Ser Tyr Tyr
1 5 10 15

<210> SEQ ID NO 111
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 111

Val Tyr Arg Pro Asp Gln Val Ser
1 5

<210> SEQ ID NO 112

<211> LENGTH: 10
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 112

Val Tyr Arg Pro Asp Gln Val Ser Ala Val
1 5 10

<210> SEQ ID NO 113
<211> LENGTH: 11
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 113

Val Tyr Arg Pro Asp Gln Val Ser Ala Val Asp
1 5 10

<210> SEQ ID NO 114
<211> LENGTH: 13
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 114

Val Tyr Arg Pro Asp Gln Val Ser Ala Val Asp Ser Tyr
1 5 10

<210> SEQ ID NO 115
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 115

Val Tyr Arg Pro Asp Gln Val Ser Ala Val Asp Ser Tyr Tyr
1 5 10

<210> SEQ ID NO 116
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 116

Val Tyr Arg Pro Asp Gln Val Ser Ala Val Asp Ser Tyr Tyr Tyr
1 5 10 15

<210> SEQ ID NO 117
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 117

```
Val Tyr Arg Pro Asp Gln Val Ser Ala Val Asp Ser Tyr Tyr Tyr Asp
1               5                   10                  15


<210> SEQ ID NO 118
<211> LENGTH: 17
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 118

Val Tyr Arg Pro Asp Gln Val Ser Ala Val Asp Ser Tyr Tyr Tyr Asp
1               5                   10                  15

Asp


<210> SEQ ID NO 119
<211> LENGTH: 18
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 119

Val Tyr Arg Pro Asp Gln Val Ser Ala Val Asp Ser Tyr Tyr Tyr Asp
1               5                   10                  15

Asp Gly


<210> SEQ ID NO 120
<211> LENGTH: 11
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 120

Arg Pro Asp Gln Val Ser Ala Val Asp Ser Tyr
1               5                   10


<210> SEQ ID NO 121
<211> LENGTH: 12
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 121

Arg Pro Asp Gln Val Ser Ala Val Asp Ser Tyr Tyr
1               5                   10


<210> SEQ ID NO 122
<211> LENGTH: 13
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 122

Arg Pro Asp Gln Val Ser Ala Val Asp Ser Tyr Tyr Tyr
1               5                   10


<210> SEQ ID NO 123
```

<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 123

Arg Pro Asp Gln Val Ser Ala Val Asp Ser Tyr Tyr Tyr Asp Asp
1 5 10 15

<210> SEQ ID NO 124
<211> LENGTH: 11
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 124

Asp Thr Phe Asn Arg Glu Pro Ala Ile Val Arg
1 5 10

<210> SEQ ID NO 125
<211> LENGTH: 10
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 125

Thr Phe Asn Arg Glu Pro Ala Ile Val Arg
1 5 10

<210> SEQ ID NO 126
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 126

Asn Arg Glu Pro Ala Ile Val Arg
1 5

<210> SEQ ID NO 127
<211> LENGTH: 9
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 127

Asn Arg Glu Pro Ala Ile Val Arg Phe
1 5

<210> SEQ ID NO 128
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 128

-continued

Arg Glu Pro Ala Ile Val Arg
1 5

<210> SEQ ID NO 129
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 129

Ser Arg Phe Thr Glu Val Arg
1 5

<210> SEQ ID NO 130
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 130

Phe Thr Glu Val Arg Glu Phe
1 5

<210> SEQ ID NO 131
<211> LENGTH: 6
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 131

Thr Glu Val Arg Glu Phe
1 5

<210> SEQ ID NO 132
<211> LENGTH: 5
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 132

Glu Val Arg Glu Phe
1 5

<210> SEQ ID NO 133
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 133

Glu Phe Ala Ile Val Pro Leu
1 5

<210> SEQ ID NO 134
<211> LENGTH: 13
<212> TYPE: PRT
<213> ORGANISM: Artificial sequence
<220> FEATURE:

<223> OTHER INFORMATION: A peptide identified following digestion with
      Trypsin and Chymotrypsin of the plant-expressed rh DNase I

<400> SEQUENCE: 134

Glu Phe Ala Ile Val Pro Leu His Ala Ala Pro Gly Asp
1               5                   10

<210> SEQ ID NO 135
<211> LENGTH: 16
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 135

Glu Phe Ala Ile Val Pro Leu His Ala Ala Pro Gly Asp Ala Val Ala
1               5                   10                  15

<210> SEQ ID NO 136
<211> LENGTH: 19
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 136

Glu Phe Ala Ile Val Pro Leu His Ala Ala Pro Gly Asp Ala Val Ala
1               5                   10                  15

Glu Ile Asp

<210> SEQ ID NO 137
<211> LENGTH: 21
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 137

Glu Phe Ala Ile Val Pro Leu His Ala Ala Pro Gly Asp Ala Val Ala
1               5                   10                  15

Glu Ile Asp Ala Leu
            20

<210> SEQ ID NO 138
<211> LENGTH: 22
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 138

Glu Phe Ala Ile Val Pro Leu His Ala Ala Pro Gly Asp Ala Val Ala
1               5                   10                  15

Glu Ile Asp Ala Leu Tyr
            20

<210> SEQ ID NO 139
<211> LENGTH: 23
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 139

Glu Phe Ala Ile Val Pro Leu His Ala Ala Pro Gly Asp Ala Val Ala
1 5 10 15

Glu Ile Asp Ala Leu Tyr Asp
20

<210> SEQ ID NO 140
<211> LENGTH: 24
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 140

Glu Phe Ala Ile Val Pro Leu His Ala Ala Pro Gly Asp Ala Val Ala
1 5 10 15

Glu Ile Asp Ala Leu Tyr Asp Val
20

<210> SEQ ID NO 141
<211> LENGTH: 25
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 141

Glu Phe Ala Ile Val Pro Leu His Ala Ala Pro Gly Asp Ala Val Ala
1 5 10 15

Glu Ile Asp Ala Leu Tyr Asp Val Tyr
20 25

<210> SEQ ID NO 142
<211> LENGTH: 31
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 142

Glu Phe Ala Ile Val Pro Leu His Ala Ala Pro Gly Asp Ala Val Ala
1 5 10 15

Glu Ile Asp Ala Leu Tyr Asp Val Tyr Leu Asp Val Gln Glu Lys
20 25 30

<210> SEQ ID NO 143
<211> LENGTH: 17
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 143

Ala Ile Val Pro Leu His Ala Ala Pro Gly Asp Ala Val Ala Glu Ile
1 5 10 15

Asp

<210> SEQ ID NO 144

<211> LENGTH: 19
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 144

Ala Ile Val Pro Leu His Ala Ala Pro Gly Asp Ala Val Ala Glu Ile
1 5 10 15

Asp Ala Leu

<210> SEQ ID NO 145
<211> LENGTH: 20
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 145

Ala Ile Val Pro Leu His Ala Ala Pro Gly Asp Ala Val Ala Glu Ile
1 5 10 15

Asp Ala Leu Tyr
20

<210> SEQ ID NO 146
<211> LENGTH: 23
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 146

Ala Ile Val Pro Leu His Ala Ala Pro Gly Asp Ala Val Ala Glu Ile
1 5 10 15

Asp Ala Leu Tyr Asp Val Tyr
20

<210> SEQ ID NO 147
<211> LENGTH: 19
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 147

Ile Val Pro Leu His Ala Ala Pro Gly Asp Ala Val Ala Glu Ile Asp
1 5 10 15

Ala Leu Tyr

<210> SEQ ID NO 148
<211> LENGTH: 28
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 148

Ile Val Pro Leu His Ala Ala Pro Gly Asp Ala Val Ala Glu Ile Asp
1 5 10 15

Ala Leu Tyr Asp Val Tyr Leu Asp Val Gln Glu Lys 20 25

<210> SEQ ID NO 149
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 149

Leu His Ala Ala Pro Gly Asp Ala Val Ala Glu Ile Asp Ala Leu Tyr
1 5 10 15

<210> SEQ ID NO 150
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 150

His Ala Ala Pro Gly Asp Ala Val Ala Glu Ile Asp Ala Leu
1 5 10

<210> SEQ ID NO 151
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 151

His Ala Ala Pro Gly Asp Ala Val Ala Glu Ile Asp Ala Leu Tyr
1 5 10 15

<210> SEQ ID NO 152
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 152

His Ala Ala Pro Gly Asp Ala Val Ala Glu Ile Asp Ala Leu Tyr Asp
1 5 10 15

<210> SEQ ID NO 153
<211> LENGTH: 17
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 153

His Ala Ala Pro Gly Asp Ala Val Ala Glu Ile Asp Ala Leu Tyr Asp
1 5 10 15

Val

<210> SEQ ID NO 154
<211> LENGTH: 18
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 154

His Ala Ala Pro Gly Asp Ala Val Ala Glu Ile Asp Ala Leu Tyr Asp
1               5                   10                  15

Val Tyr

<210> SEQ ID NO 155
<211> LENGTH: 24
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 155

His Ala Ala Pro Gly Asp Ala Val Ala Glu Ile Asp Ala Leu Tyr Asp
1               5                   10                  15

Val Tyr Leu Asp Val Gln Glu Lys
            20

<210> SEQ ID NO 156
<211> LENGTH: 9
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 156

Ala Val Ala Glu Ile Asp Ala Leu Tyr
1               5

<210> SEQ ID NO 157
<211> LENGTH: 18
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 157

Ala Val Ala Glu Ile Asp Ala Leu Tyr Asp Val Tyr Leu Asp Val Gln
1               5                   10                  15

Glu Lys

<210> SEQ ID NO 158
<211> LENGTH: 12
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 158

Ala Leu Tyr Asp Val Tyr Leu Asp Val Gln Glu Lys
1               5                   10

<210> SEQ ID NO 159
<211> LENGTH: 11
<212> TYPE: PRT
<213> ORGANISM: Artificial sequence
<220> FEATURE:
<223> OTHER INFORMATION: A peptide identified following digestion with -continued Trypsin and Chymotrypsin of the plant-expressed rh DNase I

<400> SEQUENCE: 159

Leu Tyr Asp Val Tyr Leu Asp Val Gln Glu Lys
1               5                   10

<210> SEQ ID NO 160
<211> LENGTH: 10
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 160

Tyr Asp Val Tyr Leu Asp Val Gln Glu Lys
1               5                   10

<210> SEQ ID NO 161
<211> LENGTH: 9
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 161

Asp Val Tyr Leu Asp Val Gln Glu Lys
1               5

<210> SEQ ID NO 162
<211> LENGTH: 10
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 162

Asp Val Tyr Leu Asp Val Gln Glu Lys Trp
1               5                   10

<210> SEQ ID NO 163
<211> LENGTH: 7
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 163

Tyr Leu Asp Val Gln Glu Lys
1               5

<210> SEQ ID NO 164
<211> LENGTH: 6
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 164

Leu Asp Val Gln Glu Lys
1               5

<210> SEQ ID NO 165

<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 165

Leu Asp Val Gln Glu Lys Trp
1 5

<210> SEQ ID NO 166
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 166

Leu Asp Val Gln Glu Lys Trp Gly Leu Glu Asp Val Met Leu Met
1 5 10 15

<210> SEQ ID NO 167
<211> LENGTH: 5
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 167

Asp Val Gln Glu Lys
1 5

<210> SEQ ID NO 168
<211> LENGTH: 6
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 168

Asp Val Gln Glu Lys Trp
1 5

<210> SEQ ID NO 169
<211> LENGTH: 5
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 169

Trp Gly Leu Glu Asp
1 5

<210> SEQ ID NO 170
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 170

```
Trp Gly Leu Glu Asp Val Met
1               5


<210> SEQ ID NO 171
<211> LENGTH: 8
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 171

Trp Gly Leu Glu Asp Val Met Leu
1               5


<210> SEQ ID NO 172
<211> LENGTH: 9
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 172

Trp Gly Leu Glu Asp Val Met Leu Met
1               5


<210> SEQ ID NO 173
<211> LENGTH: 10
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 173

Trp Gly Leu Glu Asp Val Met Leu Met Gly
1               5                   10


<210> SEQ ID NO 174
<211> LENGTH: 18
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 174

Trp Gly Leu Glu Asp Val Met Leu Met Gly Asp Phe Asn Ala Gly Cys
1               5                   10                  15

Ser Tyr


<210> SEQ ID NO 175
<211> LENGTH: 20
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 175

Trp Gly Leu Glu Asp Val Met Leu Met Gly Asp Phe Asn Ala Gly Cys
1               5                   10                  15

Ser Tyr Val Arg
            20
```

<210> SEQ ID NO 176
<211> LENGTH: 28
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 176

Trp Gly Leu Glu Asp Val Met Leu Met Gly Asp Phe Asn Ala Gly Cys
1 5 10 15

Ser Tyr Val Arg Pro Ser Gln Trp Ser Ser Ile Arg
20 25

<210> SEQ ID NO 177
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 177

Gly Leu Glu Asp Val Met Leu
1 5

<210> SEQ ID NO 178
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 178

Gly Leu Glu Asp Val Met Leu Met
1 5

<210> SEQ ID NO 179
<211> LENGTH: 17
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 179

Gly Leu Glu Asp Val Met Leu Met Gly Asp Phe Asn Ala Gly Cys Ser
1 5 10 15

Tyr

<210> SEQ ID NO 180
<211> LENGTH: 17
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 180

Leu Met Gly Asp Phe Asn Ala Gly Cys Ser Tyr Val Arg Pro Ser Gln
1 5 10 15

Trp

<210> SEQ ID NO 181
<211> LENGTH: 10

```
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 181

Met Gly Asp Phe Asn Ala Gly Cys Ser Tyr
1               5                   10


<210> SEQ ID NO 182
<211> LENGTH: 12
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 182

Met Gly Asp Phe Asn Ala Gly Cys Ser Tyr Val Arg
1               5                   10


<210> SEQ ID NO 183
<211> LENGTH: 16
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 183

Met Gly Asp Phe Asn Ala Gly Cys Ser Tyr Val Arg Pro Ser Gln Trp
1               5                   10                  15


<210> SEQ ID NO 184
<211> LENGTH: 20
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 184

Met Gly Asp Phe Asn Ala Gly Cys Ser Tyr Val Arg Pro Ser Gln Trp
1               5                   10                  15

Ser Ser Ile Arg
            20


<210> SEQ ID NO 185
<211> LENGTH: 9
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 185

Gly Asp Phe Asn Ala Gly Cys Ser Tyr
1               5


<210> SEQ ID NO 186
<211> LENGTH: 11
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I
```

<400> SEQUENCE: 186

Gly Asp Phe Asn Ala Gly Cys Ser Tyr Val Arg
1 5 10

<210> SEQ ID NO 187
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 187

Gly Asp Phe Asn Ala Gly Cys Ser Tyr Val Arg Pro Ser Gln Trp
1 5 10 15

<210> SEQ ID NO 188
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 188

Gly Asp Phe Asn Ala Gly Cys Ser Tyr Val Arg Pro Ser Gln Trp Ser
1 5 10 15

<210> SEQ ID NO 189
<211> LENGTH: 14
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 189

Asp Phe Asn Ala Gly Cys Ser Tyr Val Arg Pro Ser Gln Trp
1 5 10

<210> SEQ ID NO 190
<211> LENGTH: 12
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 190

Asn Ala Gly Cys Ser Tyr Val Arg Pro Ser Gln Trp
1 5 10

<210> SEQ ID NO 191
<211> LENGTH: 11
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 191

Ala Gly Cys Ser Tyr Val Arg Pro Ser Gln Trp
1 5 10

<210> SEQ ID NO 192
<211> LENGTH: 8
<212> TYPE: PRT

<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 192

Ser Tyr Val Arg Pro Ser Gln Trp
1               5

<210> SEQ ID NO 193
<211> LENGTH: 12
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 193

Ser Tyr Val Arg Pro Ser Gln Trp Ser Ser Ile Arg
1               5                   10

<210> SEQ ID NO 194
<211> LENGTH: 7
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 194

Tyr Val Arg Pro Ser Gln Trp
1               5

<210> SEQ ID NO 195
<211> LENGTH: 6
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 195

Val Arg Pro Ser Gln Trp
1               5

<210> SEQ ID NO 196
<211> LENGTH: 10
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 196

Val Arg Pro Ser Gln Trp Ser Ser Ile Arg
1               5                   10

<210> SEQ ID NO 197
<211> LENGTH: 8
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 197

Pro Ser Gln Trp Ser Ser Ile Arg
1               5

<210> SEQ ID NO 198
<211> LENGTH: 6
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 198

Gln Trp Ser Ser Ile Arg
1               5

<210> SEQ ID NO 199
<211> LENGTH: 6
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 199

Ser Ser Ile Arg Leu Trp
1               5

<210> SEQ ID NO 200
<211> LENGTH: 6
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 200

Leu Trp Thr Ser Pro Thr
1               5

<210> SEQ ID NO 201
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 201

Leu Trp Thr Ser Pro Thr Phe
1               5

<210> SEQ ID NO 202
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 202

Leu Trp Thr Ser Pro Thr Phe Gln
1               5

<210> SEQ ID NO 203
<211> LENGTH: 9
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 203

Leu Trp Thr Ser Pro Thr Phe Gln Trp
1 5

<210> SEQ ID NO 204
<211> LENGTH: 10
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 204

Leu Trp Thr Ser Pro Thr Phe Gln Trp Leu
1 5 10

<210> SEQ ID NO 205
<211> LENGTH: 13
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 205

Leu Trp Thr Ser Pro Thr Phe Gln Trp Leu Ile Pro Asp
1 5 10

<210> SEQ ID NO 206
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 206

Leu Trp Thr Ser Pro Thr Phe Gln Trp Leu Ile Pro Asp Ser Ala Asp
1 5 10 15

<210> SEQ ID NO 207
<211> LENGTH: 23
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 207

Leu Trp Thr Ser Pro Thr Phe Gln Trp Leu Ile Pro Asp Ser Ala Asp
1 5 10 15

Thr Thr Ala Thr Pro Thr His
20

<210> SEQ ID NO 208
<211> LENGTH: 26
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 208

Leu Trp Thr Ser Pro Thr Phe Gln Trp Leu Ile Pro Asp Ser Ala Asp
1 5 10 15

```
Thr Thr Ala Thr Pro Thr His Cys Ala Tyr
            20                  25


<210> SEQ ID NO 209
<211> LENGTH: 28
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 209

Leu Trp Thr Ser Pro Thr Phe Gln Trp Leu Ile Pro Asp Ser Ala Asp
1               5                   10                  15

Thr Thr Ala Thr Pro Thr His Cys Ala Tyr Asp Arg
            20                  25


<210> SEQ ID NO 210
<211> LENGTH: 27
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 210

Trp Thr Ser Pro Thr Phe Gln Trp Leu Ile Pro Asp Ser Ala Asp Thr
1               5                   10                  15

Thr Ala Thr Pro Thr His Cys Ala Tyr Asp Arg
            20                  25


<210> SEQ ID NO 211
<211> LENGTH: 6
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 211

Thr Ser Pro Thr Phe Gln
1               5


<210> SEQ ID NO 212
<211> LENGTH: 7
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 212

Thr Ser Pro Thr Phe Gln Trp
1               5


<210> SEQ ID NO 213
<211> LENGTH: 8
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 213

Thr Ser Pro Thr Phe Gln Trp Leu
1               5
```

```
<210> SEQ ID NO 214
<211> LENGTH: 21
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 214

Thr Ser Pro Thr Phe Gln Trp Leu Ile Pro Asp Ser Ala Asp Thr Thr
1               5                   10                  15

Ala Thr Pro Thr His
            20


<210> SEQ ID NO 215
<211> LENGTH: 24
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 215

Thr Ser Pro Thr Phe Gln Trp Leu Ile Pro Asp Ser Ala Asp Thr Thr
1               5                   10                  15

Ala Thr Pro Thr His Cys Ala Tyr
            20


<210> SEQ ID NO 216
<211> LENGTH: 26
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 216

Thr Ser Pro Thr Phe Gln Trp Leu Ile Pro Asp Ser Ala Asp Thr Thr
1               5                   10                  15

Ala Thr Pro Thr His Cys Ala Tyr Asp Arg
            20                  25


<210> SEQ ID NO 217
<211> LENGTH: 22
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 217

Phe Gln Trp Leu Ile Pro Asp Ser Ala Asp Thr Thr Ala Thr Pro Thr
1               5                   10                  15

His Cys Ala Tyr Asp Arg
            20


<210> SEQ ID NO 218
<211> LENGTH: 19
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 218
```

-continued

Gln Trp Leu Ile Pro Asp Ser Ala Asp Thr Thr Ala Thr Pro Thr His
1 5 10 15

Cys Ala Tyr

<210> SEQ ID NO 219
<211> LENGTH: 21
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 219

Gln Trp Leu Ile Pro Asp Ser Ala Asp Thr Thr Ala Thr Pro Thr His
1 5 10 15

Cys Ala Tyr Asp Arg
20

<210> SEQ ID NO 220
<211> LENGTH: 19
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 220

Leu Ile Pro Asp Ser Ala Asp Thr Thr Ala Thr Pro Thr His Cys Ala
1 5 10 15

Tyr Asp Arg

<210> SEQ ID NO 221
<211> LENGTH: 16
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 221

Ile Pro Asp Ser Ala Asp Thr Thr Ala Thr Pro Thr His Cys Ala Tyr
1 5 10 15

<210> SEQ ID NO 222
<211> LENGTH: 18
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 222

Ile Pro Asp Ser Ala Asp Thr Thr Ala Thr Pro Thr His Cys Ala Tyr
1 5 10 15

Asp Arg

<210> SEQ ID NO 223
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 223

Ser Ala Asp Thr Thr Ala Thr Pro Thr His Cys Ala Tyr Asp Arg
1 5 10 15

<210> SEQ ID NO 224
<211> LENGTH: 13
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 224

Asp Thr Thr Ala Thr Pro Thr His Cys Ala Tyr Asp Arg
1 5 10

<210> SEQ ID NO 225
<211> LENGTH: 10
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 225

Thr Thr Ala Thr Pro Thr His Cys Ala Tyr
1 5 10

<210> SEQ ID NO 226
<211> LENGTH: 11
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 226

Thr Ala Thr Pro Thr His Cys Ala Tyr Asp Arg
1 5 10

<210> SEQ ID NO 227
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 227

Pro Thr His Cys Ala Tyr Asp Arg
1 5

<210> SEQ ID NO 228
<211> LENGTH: 6
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 228

Asp Arg Ile Val Val Ala
1 5

<210> SEQ ID NO 229
<211> LENGTH: 8
<212> TYPE: PRT
<213> ORGANISM: Artificial sequence
<220> FEATURE:

<223> OTHER INFORMATION: A peptide identified following digestion with Trypsin and Chymotrypsin of the plant-expressed rh DNase I

<400> SEQUENCE: 229

Asp Arg Ile Val Val Ala Gly Met
1 5

<210> SEQ ID NO 230
<211> LENGTH: 9
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 230

Asp Arg Ile Val Val Ala Gly Met Leu
1 5

<210> SEQ ID NO 231
<211> LENGTH: 10
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 231

Asp Arg Ile Val Val Ala Gly Met Leu Leu
1 5 10

<210> SEQ ID NO 232
<211> LENGTH: 11
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 232

Asp Arg Ile Val Val Ala Gly Met Leu Leu Arg
1 5 10

<210> SEQ ID NO 233
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 233

Ile Val Val Ala Gly Met Leu
1 5

<210> SEQ ID NO 234
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 234

Ile Val Val Ala Gly Met Leu Leu
1 5

<210> SEQ ID NO 235
<211> LENGTH: 9
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 235

Ile Val Val Ala Gly Met Leu Leu Arg
1               5

<210> SEQ ID NO 236
<211> LENGTH: 10
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 236

Ile Val Val Ala Gly Met Leu Leu Arg Gly
1               5                   10

<210> SEQ ID NO 237
<211> LENGTH: 8
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 237

Val Val Ala Gly Met Leu Leu Arg
1               5

<210> SEQ ID NO 238
<211> LENGTH: 7
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 238

Val Ala Gly Met Leu Leu Arg
1               5

<210> SEQ ID NO 239
<211> LENGTH: 6
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 239

Ala Gly Met Leu Leu Arg
1               5

<210> SEQ ID NO 240
<211> LENGTH: 8
<212> TYPE: PRT
<213> ORGANISM: Artificial sequence
<220> FEATURE:
<223> OTHER INFORMATION: A peptide identified following digestion with
Trypsin and Chymotrypsin of the plant-expressed rh DNase I

<400> SEQUENCE: 240

Met Leu Leu Arg Gly Ala Val Val
1               5

<210> SEQ ID NO 241
<211> LENGTH: 13
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 241

Leu Arg Gly Ala Val Val Pro Asp Ser Ala Leu Pro Phe
1               5                   10

<210> SEQ ID NO 242
<211> LENGTH: 12
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 242

Arg Gly Ala Val Val Pro Asp Ser Ala Leu Pro Phe
1               5                   10

<210> SEQ ID NO 243
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 243

Gly Ala Val Val Pro Asp Ser
1               5

<210> SEQ ID NO 244
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 244

Gly Ala Val Val Pro Asp Ser Ala
1               5

<210> SEQ ID NO 245
<211> LENGTH: 9
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 245

Gly Ala Val Val Pro Asp Ser Ala Leu
1               5

<210> SEQ ID NO 246
<211> LENGTH: 10
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 246

```
Gly Ala Val Val Pro Asp Ser Ala Leu Pro
1               5                   10
```

<210> SEQ ID NO 247
<211> LENGTH: 13
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 247

```
Gly Ala Val Val Pro Asp Ser Ala Leu Pro Phe Asn Phe
1               5                   10
```

<210> SEQ ID NO 248
<211> LENGTH: 16
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 248

```
Gly Ala Val Val Pro Asp Ser Ala Leu Pro Phe Asn Phe Gln Ala Ala
1               5                   10                  15
```

<210> SEQ ID NO 249
<211> LENGTH: 17
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 249

```
Gly Ala Val Val Pro Asp Ser Ala Leu Pro Phe Asn Phe Gln Ala Ala
1               5                   10                  15

Tyr
```

<210> SEQ ID NO 250
<211> LENGTH: 18
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 250

```
Gly Ala Val Val Pro Asp Ser Ala Leu Pro Phe Asn Phe Gln Ala Ala
1               5                   10                  15

Tyr Gly
```

<210> SEQ ID NO 251
<211> LENGTH: 19
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 251

```
Gly Ala Val Val Pro Asp Ser Ala Leu Pro Phe Asn Phe Gln Ala Ala
1               5                   10                  15

Tyr Gly Leu


<210> SEQ ID NO 252
<211> LENGTH: 21
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 252

Gly Ala Val Val Pro Asp Ser Ala Leu Pro Phe Asn Phe Gln Ala Ala
1               5                   10                  15

Tyr Gly Leu Ser Asp
            20


<210> SEQ ID NO 253
<211> LENGTH: 38
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 253

Gly Ala Val Val Pro Asp Ser Ala Leu Pro Phe Asn Phe Gln Ala Ala
1               5                   10                  15

Tyr Gly Leu Ser Asp Gln Leu Ala Gln Ala Ile Ser Asp His Tyr Pro
            20                  25                  30

Val Glu Val Met Leu Lys
        35


<210> SEQ ID NO 254
<211> LENGTH: 6
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 254

Asn Phe Gln Ala Ala Tyr
1               5


<210> SEQ ID NO 255
<211> LENGTH: 7
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I

<400> SEQUENCE: 255

Asn Phe Gln Ala Ala Tyr Gly
1               5


<210> SEQ ID NO 256
<211> LENGTH: 20
<212> TYPE: PRT
<213> ORGANISM: Artificial sequence
<220> FEATURE:
<223> OTHER INFORMATION: A peptide identified following digestion with
      Trypsin and Chymotrypsin of the plant-expressed rh DNase I
```

<400> SEQUENCE: 256

Asn Phe Gln Ala Ala Tyr Gly Leu Ser Asp Gln Leu Ala Gln Ala Ile
1 5 10 15

Ser Asp His Tyr
20

<210> SEQ ID NO 257
<211> LENGTH: 27
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 257

Asn Phe Gln Ala Ala Tyr Gly Leu Ser Asp Gln Leu Ala Gln Ala Ile
1 5 10 15

Ser Asp His Tyr Pro Val Glu Val Met Leu Lys
20 25

<210> SEQ ID NO 258
<211> LENGTH: 26
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 258

Phe Gln Ala Ala Tyr Gly Leu Ser Asp Gln Leu Ala Gln Ala Ile Ser
1 5 10 15

Asp His Tyr Pro Val Glu Val Met Leu Lys
20 25

<210> SEQ ID NO 259
<211> LENGTH: 25
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 259

Gln Ala Ala Tyr Gly Leu Ser Asp Gln Leu Ala Gln Ala Ile Ser Asp
1 5 10 15

His Tyr Pro Val Glu Val Met Leu Lys
20 25

<210> SEQ ID NO 260
<211> LENGTH: 24
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 260

Ala Ala Tyr Gly Leu Ser Asp Gln Leu Ala Gln Ala Ile Ser Asp His
1 5 10 15

Tyr Pro Val Glu Val Met Leu Lys
20

<210> SEQ ID NO 261

<211> LENGTH: 23
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 261

Ala Tyr Gly Leu Ser Asp Gln Leu Ala Gln Ala Ile Ser Asp His Tyr
1 5 10 15

Pro Val Glu Val Met Leu Lys
20

<210> SEQ ID NO 262
<211> LENGTH: 8
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 262

Gly Leu Ser Asp Gln Leu Ala Gln
1 5

<210> SEQ ID NO 263
<211> LENGTH: 10
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 263

Gly Leu Ser Asp Gln Leu Ala Gln Ala Ile
1 5 10

<210> SEQ ID NO 264
<211> LENGTH: 13
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 264

Gly Leu Ser Asp Gln Leu Ala Gln Ala Ile Ser Asp His
1 5 10

<210> SEQ ID NO 265
<211> LENGTH: 17
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 265

Gly Leu Ser Asp Gln Leu Ala Gln Ala Ile Ser Asp His Tyr Pro Val
1 5 10 15

Glu

<210> SEQ ID NO 266
<211> LENGTH: 18
<212> TYPE: PRT
<213> ORGANISM: Artificial sequence
<220> FEATURE:

<223> OTHER INFORMATION: A peptide identified following digestion with Trypsin and Chymotrypsin of the plant-expressed rh DNase I

<400> SEQUENCE: 266

Gly Leu Ser Asp Gln Leu Ala Gln Ala Ile Ser Asp His Tyr Pro Val
1 5 10 15

Glu Val

<210> SEQ ID NO 267
<211> LENGTH: 19
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 267

Gly Leu Ser Asp Gln Leu Ala Gln Ala Ile Ser Asp His Tyr Pro Val
1 5 10 15

Glu Val Met

<210> SEQ ID NO 268
<211> LENGTH: 20
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 268

Gly Leu Ser Asp Gln Leu Ala Gln Ala Ile Ser Asp His Tyr Pro Val
1 5 10 15

Glu Val Met Leu
20

<210> SEQ ID NO 269
<211> LENGTH: 21
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 269

Gly Leu Ser Asp Gln Leu Ala Gln Ala Ile Ser Asp His Tyr Pro Val
1 5 10 15

Glu Val Met Leu Lys
20

<210> SEQ ID NO 270
<211> LENGTH: 19
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 270

Ser Asp Gln Leu Ala Gln Ala Ile Ser Asp His Tyr Pro Val Glu Val
1 5 10 15

Met Leu Lys

<210> SEQ ID NO 271
<211> LENGTH: 17

<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 271

Gln Leu Ala Gln Ala Ile Ser Asp His Tyr Pro Val Glu Val Met Leu
1 5 10 15

Lys

<210> SEQ ID NO 272
<211> LENGTH: 15
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 272

Ala Gln Ala Ile Ser Asp His Tyr Pro Val Glu Val Met Leu Lys
1 5 10 15

<210> SEQ ID NO 273
<211> LENGTH: 13
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 273

Ala Ile Ser Asp His Tyr Pro Val Glu Val Met Leu Lys
1 5 10

<210> SEQ ID NO 274
<211> LENGTH: 11
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 274

Ser Asp His Tyr Pro Val Glu Val Met Leu Lys
1 5 10

<210> SEQ ID NO 275
<211> LENGTH: 9
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 275

His Tyr Pro Val Glu Val Met Leu Lys
1 5

<210> SEQ ID NO 276
<211> LENGTH: 7
<212> TYPE: PRT
<213> ORGANISM: Artificial sequence
<220> FEATURE:
<223> OTHER INFORMATION: A peptide identified following digestion with Trypsin and Chymotrypsin of the plant-expressed rh DNase I

<400> SEQUENCE: 276

```
Pro Val Glu Val Met Leu Lys
1               5


<210> SEQ ID NO 277
<211> LENGTH: 789
<212> TYPE: DNA
<213> ORGANISM: Artificial sequence
<220> FEATURE:
<223> OTHER INFORMATION: Coding sequence of the recombinant DNase I with
      an additional N' Gly residue (DNase I + G)

<400> SEQUENCE: 277

ggccttaaaa tcgctgcttt caacatccaa actttcggag agactaagat gtctaacgct     60

actcttgtgt cctacatcgt tcagattctc tccagatacg atattgctct tgttcaggaa    120

gttagggatt ctcaccttac tgctgtggga aagcttcttg ataacctcaa tcaggatgct    180

ccagatactt accactacgt tgtgtctgaa ccacttggaa gaaactccta caaagagcgt    240

tacctctttg tttaccgtcc agatcaagtt tctgctgtgg attcctacta ctacgatgat    300

ggatgtgagc catgcggaaa cgatactttc aatagagagc cagctatcgt tcgttttttc    360

agtaggttca ctgaagttcg tgagtttgct attgtgccac ttcatgctgc tccaggtgat    420

gctgttgctg agattgatgc tctctacgat gtgtaccttg atgttcaaga gaagtgggga    480

ttggaggatg ttatgctcat gggagatttc aatgctggat gctcttatgt taggccatct    540

cagtggtcat ctattaggct ttggacttcc ccaactttcc aatggcttat cccagattcc    600

gctgatacaa ctgctactcc aactcattgt gcttacgata ggattgtggt ggctggaatg    660

cttcttagag gtgctgttgt tccagattct gctctcccat tcaatttcca agctgcttac    720

ggactttctg atcaacttgc tcaggctatt tctgatcact acccagttga ggtgatgttg    780

aagtgatga                                                            789


<210> SEQ ID NO 278
<211> LENGTH: 13
<212> TYPE: PRT
<213> ORGANISM: Artificial sequence
<220> FEATURE:
<223> OTHER INFORMATION: A peptide identified following digestion with
      Trypsin and PNGaseA of the plant-expressed rh DNase I

<400> SEQUENCE: 278

Ile Ala Ala Phe Asn Ile Gln Thr Phe Gly Glu Thr Lys
1               5                   10


<210> SEQ ID NO 279
<211> LENGTH: 16
<212> TYPE: PRT
<213> ORGANISM: Artificial sequence
<220> FEATURE:
<223> OTHER INFORMATION: A peptide identified following digestion with
      Trypsin and PNGaseA of the plant-expressed rh DNase I

<400> SEQUENCE: 279

Met Ser Asn Ala Thr Leu Val Ser Tyr Ile Val Gln Ile Leu Ser Arg
1               5                   10                  15


<210> SEQ ID NO 280
<211> LENGTH: 10
<212> TYPE: PRT
<213> ORGANISM: Artificial sequence
<220> FEATURE:
<223> OTHER INFORMATION: A peptide identified following digestion with
      Trypsin and PNGaseA of the plant-expressed rh DNase I
```

<400> SEQUENCE: 280

Tyr Asp Ile Ala Leu Val Gln Glu Val Arg
1 5 10

<210> SEQ ID NO 281
<211> LENGTH: 9
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 281

Asp Ser His Leu Thr Ala Val Gly Lys
1 5

<210> SEQ ID NO 282
<211> LENGTH: 23
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 282

Leu Leu Asp Asn Leu Asn Gln Asp Ala Pro Asp Thr Tyr His Tyr Val
1 5 10 15

Val Ser Glu Pro Leu Gly Arg
20

<210> SEQ ID NO 283
<211> LENGTH: 27
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 283

Leu Leu Asp Asn Leu Asn Gln Asp Ala Pro Asp Thr Tyr His Tyr Val
1 5 10 15

Val Ser Glu Pro Leu Gly Arg Asn Ser Tyr Lys
20 25

<210> SEQ ID NO 284
<211> LENGTH: 32
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 284

Tyr Leu Phe Val Tyr Arg Pro Asp Gln Val Ser Ala Val Asp Ser Tyr
1 5 10 15

Tyr Tyr Asp Asp Gly Cys Glu Pro Cys Gly Asn Asp Thr Phe Asn Arg
20 25 30

<210> SEQ ID NO 285
<211> LENGTH: 38
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 285

Tyr Leu Phe Val Tyr Arg Pro Asp Gln Val Ser Ala Val Asp Ser Tyr
1               5                   10                  15

Tyr Tyr Asp Asp Gly Cys Glu Pro Cys Gly Asn Asp Thr Phe Asn Arg
            20                  25                  30

Glu Pro Ala Ile Val Arg
        35

<210> SEQ ID NO 286
<211> LENGTH: 6
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 286

Glu Pro Ala Ile Val Arg
1               5

<210> SEQ ID NO 287
<211> LENGTH: 4
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 287

Phe Phe Ser Arg
1

<210> SEQ ID NO 288
<211> LENGTH: 5
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 288

Phe Thr Glu Val Arg
1               5

<210> SEQ ID NO 289
<211> LENGTH: 31
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I

<400> SEQUENCE: 289

Glu Phe Ala Ile Val Pro Leu His Ala Ala Pro Gly Asp Ala Val Ala
1               5                   10                  15

Glu Ile Asp Ala Leu Tyr Asp Val Tyr Leu Asp Val Gln Glu Lys
            20                  25                  30

<210> SEQ ID NO 290
<211> LENGTH: 9
<212> TYPE: PRT
<213> ORGANISM: Artificial sequence
<220> FEATURE:
<223> OTHER INFORMATION: A peptide identified following digestion with Trypsin and PNGaseA of the plant-expressed rh DNase I -continued

```
<400> SEQUENCE: 290

Ile Val Val Ala Gly Met Leu Leu Arg
1               5


<210> SEQ ID NO 291
<211> LENGTH: 38
<212> TYPE: PRT
<213> ORGANISM: Artificial sequence
<220> FEATURE:
<223> OTHER INFORMATION: A peptide identified following digestion with
      Trypsin and PNGaseA of the plant-expressed rh DNase I

<400> SEQUENCE: 291

Gly Ala Val Val Pro Asp Ser Ala Leu Pro Phe Asn Phe Gln Ala Ala
1               5                   10                  15

Tyr Gly Leu Ser Asp Gln Leu Ala Gln Ala Ile Ser Asp His Tyr Pro
            20                  25                  30

Val Glu Val Met Leu Lys
        35
```

INHALABLE LIQUID FORMULATIONS OF DNASE I

RELATED APPLICATIONS

This application is a National Phase of PCT Patent Application No. PCT/IL2013/050096 having International filing date of Jan. 31, 2013, which claims the benefit of priority under 35 USC §119(e) of U.S. Provisional Patent Application Nos. 61/593,350 filed on Feb. 1, 2012, 61/593,676 filed on Feb. 1, 2012 and 61/593,788 filed on Feb. 1, 2012. The contents of the above applications are all incorporated by reference as if fully set forth herein in their entirety.

SEQUENCE LISTING STATEMENT

The ASCII file, entitled 59970SequenceListing.txt, created on Jul. 16, 2014, comprising 111,600 bytes, submitted concurrently with the filing of this application is incorporated herein by reference.

FIELD AND BACKGROUND OF THE INVENTION

Human DNase I is a member of the mammalian DNase I family (EC 3.1.21.1). DNase I belongs to the class of $Mg^{2+}$ and $Ca^{2+}$ dependent endonucleases, whose hydrolytic activity depends on the presence of bivalent metals. Magnesium ion is involved in electrophilic catalysis of the phosphodiester bond cleavage, whereas $Ca^{2+}$ maintains optimal enzyme conformation. DNase I cleaves DNA preferentially at phosphodiester linkages adjacent to a pyrimidine nucleotide, yielding 5'-phosphate-terminated polynucleotides with a free hydroxyl group on position 3', on average producing tetranucleotides. It acts on single-stranded DNA, double-stranded DNA, and chromatin.

The principal therapeutic use of human DNase has been to reduce the viscoelasticity of pulmonary secretions (including mucus) in such diseases as pneumonia and cystic fibrosis (CF), thereby aiding in the clearing of respiratory airways. Mucus also contributes to the morbidity of chronic bronchitis, asthmatic bronchitis, bronchiectasis, emphysema, acute and chronic sinusitis, and even the common cold. DNase I is effective in reducing the viscoelasticity of pulmonary secretions and fluids by hydrolyzing high-molecular-weight DNA present in pulmonary secretions and fluids. DNase has also been proposed for non-pulmonary disorders, for example, treatment of male infertility and uterine disorders (see US 2007/0259367), inhibition of metastatic growth (see U.S. Pat. No. 7,612,032) and for treatment of sepsis and viral, bacterial, fungal and protozoan infections.

DNA encoding human DNase I was isolated and sequenced, and expressed in recombinant host cells, thereby enabling the production of human DNase in commercially useful quantities. Recombinant human DNase (rhDNase) (e.g. dornase alfa; Pulmozyme®, Genentech, Calif.), expressed in Chinese hamster ovary (CHO) cells, has been found to be clinically effective for CF.

Recombinant human DNase (rhDNase) (e.g. dornase alfa; Pulmozyme®, Genentech, Calif.) was approved for clinical use by the FDA in 1994, and additional human clinical trials with recombinant human DNase I are currently in progress for CF (see NCT01155752; NCT0017998; NCT00117208 and NCT00204685) and other chronic, respiratory diseases such as atelectasis (see NCT01095276 and NCT00671323) and Sjogren's Syndrome. In general, safety and efficacy of the rhDNase has been demonstrated. Pulmozyme® is provided as a liquid protein formulation ready for use in nebulizer systems.

In addition to nebulizer systems, pulmonary administration of drugs and other pharmaceuticals can be accomplished by provision of an inhalable solution formulated for inhalation by means of suitable liquid-based inhalers known as metered dosage inhalers.

SUMMARY OF THE INVENTION

According to an aspect of some embodiments of the present invention there is provided an inhalable pharmaceutical composition for pulmonary administration comprising a human DNase I protein and a physiologically acceptable pharmacologically-inert liquid carrier.

According to an aspect of some embodiments of the present invention there is provided a liquid inhaler device, comprising the inhalable pharmaceutical composition comprising a human DNase I protein and a physiologically acceptable pharmacologically-inert liquid carrier, and a means for introducing the pharmaceutical composition into the airways of a subject by inhalation.

According to some embodiments of the present invention the device is a single dose or a multidose inhaler.

According to some embodiments of the present invention the device is premetered or device-metered.

According to some embodiments of the present invention the device is a metered dose inhaler or a nebulizer.

According to some embodiments of the present invention the pharmaceutical composition is provided for inhalation in particles ranging from about 1 to 10 microns in size.

According to some embodiments of the present invention the pharmaceutical composition is provided for inhalation in particles ranging from about 2 to 5 microns in size.

According to some embodiments of the present invention the human DNase I protein is a recombinant human DNase I protein.

According to some embodiments of the present invention the human DNase I protein is a plant-expressed human DNase I protein.

According to some embodiments of the present invention the human DNase I protein comprises an N-terminal Glycine residue.

According to some embodiments of the present invention the human DNase I protein comprises the amino acid sequence as set forth in SEQ ID NO: 6.

According to some embodiments of the present invention the human DNase I protein comprises the amino acid sequence as set forth in SEQ ID NO:5.

According to some embodiments of the present invention the human DNase I protein has at least one core xylose and at least one core α-(1,3) fucose.

According to some embodiments of the present invention the human DNase I protein has reduced susceptibility to actin inhibition of endonuclease activity as compared with that of mammalian cell expressed human recombinant DNase I.

According to some embodiments of the present invention the liquid carrier is selected from the group consisting of water, an aqueous alcoholic solution, perfluorocarbon and saline.

According to some embodiments of the present invention the inhalable pharmaceutical composition further comprises, as an active ingredient, a magnesium salt.

According to some embodiments of the present invention the inhalable pharmaceutical composition further comprises, as an active ingredient, an agent for inhibiting formation of G actin and/or enhancing formation of F actin.

According to some embodiments of the present invention the inhalable pharmaceutical composition further comprises one or more additive materials selected from the group consisting of a surfactant, a mucolytic agent, an adsorption enhancer and a lubricant.

According to some embodiments of the present invention human DNase I protein is formulated in liposomes.

According to some embodiments of the present invention the human DNase I protein is at least 90-95% pure human DNase I protein.

According to some embodiments of the present invention the inhalable pharmaceutical composition further comprising plant beta-acetylhexosaminidase enzyme protein. In some embodiments the plant beta-acetylhexosaminidase enzyme protein is inactivated beta-acetylhexosaminidase enzyme protein. In some embodiments the beta-acetylhexosaminidase enzyme protein is heat inactivated beta-acetylhexosaminidase enzyme protein.

According to an aspect of some embodiments of the present invention there is provided method of reducing extracellular DNA in a secretion, fluid or tissue of subject in need thereof, the method comprising administering to the subject in need to thereof an effective amount of the inhalable pharmaceutical composition comprising the human DNase I protein and a physiologically acceptable pharmacologically-inert liquid carrier of the invention.

According to some embodiments of the present invention the subject is suffering from a disease or condition selected from the group consisting of male infertility, metastatic cancer, a viral, bacterial, fungal or protozoan infection, sepsis, atherosclerosis, diabetes, delayed type hypersensitivity and a uterine disorder.

According to an aspect of some embodiments of the present invention there is provided a method for reducing DNA in a pulmonary secretion or fluid of a subject in need thereof, the method comprising administering to the subject in need thereof an effective amount of the inhalable pharmaceutical composition comprising the human DNase I protein and a physiologically acceptable pharmacologically-inert liquid carrier of the invention.

According to an aspect of some embodiments of the present invention there is provided a method for the prevention and/or treatment of a pulmonary disease or condition associated with excess DNA in a pulmonary secretion in a subject in need thereof, the method comprising administering to a subject in need thereof an effective amount of the inhalable pharmaceutical composition comprising the human DNase I protein and a physiologically acceptable pharmacologically-inert liquid carrier of the invention.

According to some embodiments of the present invention the subject is suffering from a respiratory disease selected from the group consisting of acute or chronic bronchopulmonary disease, atelectasis due to tracheal or bronchial impaction, and complications of tracheostomy.

According to some embodiments of the present invention the acute or chronic bronchopulmonary disease is selected from the group consisting of infectious pneumonia, bronchitis or tracheobronchitis, bronchiectasis, cystic fibrosis, asthma, chronic obstructive pulmonary disease (COPD), TB or fungal infections.

According to some embodiments of the present invention the effective amount of the inhalable pharmaceutical composition is a single dose of 0.1 to 25 mg DNase I, administered daily.

According to some embodiments of the present invention the effective amount of the inhalable pharmaceutical composition is a single dose of 0.5 to 15 mg DNase I, administered daily.

According to some embodiments of the present invention the effective amount of the inhalable pharmaceutical composition is a single dose of 1.0 to 10 mg DNase I, administered daily.

According to some embodiments of the present invention the effective amount of the inhalable pharmaceutical composition is a single dose of 2.0 to 5 mg DNase I, administered daily.

According to some embodiments of the present invention the effective amount of the inhalable pharmaceutical composition is a single dose of 2.0-3.0 mg DNase I, administered daily.

According to some embodiments of the present invention the effective amount of the inhalable pharmaceutical composition is a plurality of doses, each dose comprising 1.0-3.0 mg DNase, the doses administered at least twice, 2-3 times, 2-4 times or 2-6 times daily.

According to some embodiments of the present invention the effective amount of the inhalable pharmaceutical composition is a plurality of doses, each dose comprising 1.0-3.0 mg DNase, the doses administered once every 36 hours, once every 36-48 hours, once every 36-72 hours, once every 2-3 days, once every 2-4 days, once every 2-5 days, or once every week.

According to some embodiments of the present invention the effective amount of the inhalable pharmaceutical composition is a plurality of doses, each dose comprising 1.0-3.0 mg DNase, the doses administered once every 36 hours, once every 36-48 hours, once every 36-72 hours, once every 2-3 days, once every 2-4 days, once every 2-5 days, or once every week.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 2:
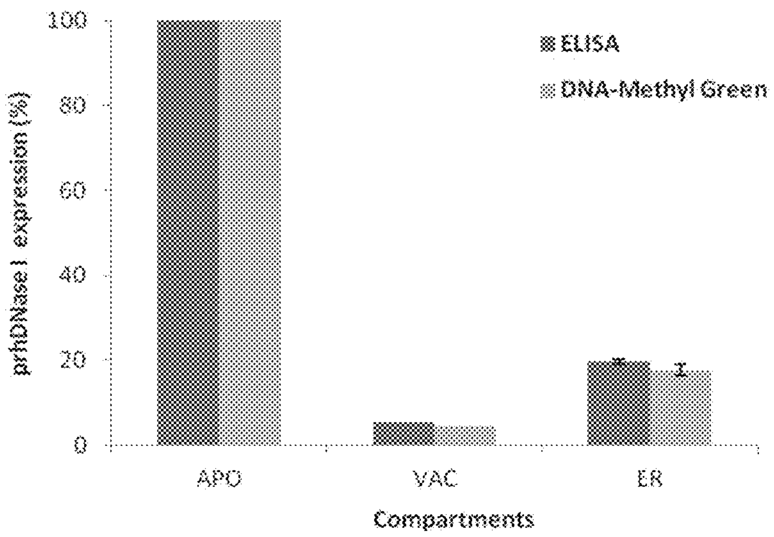
Figure 3:
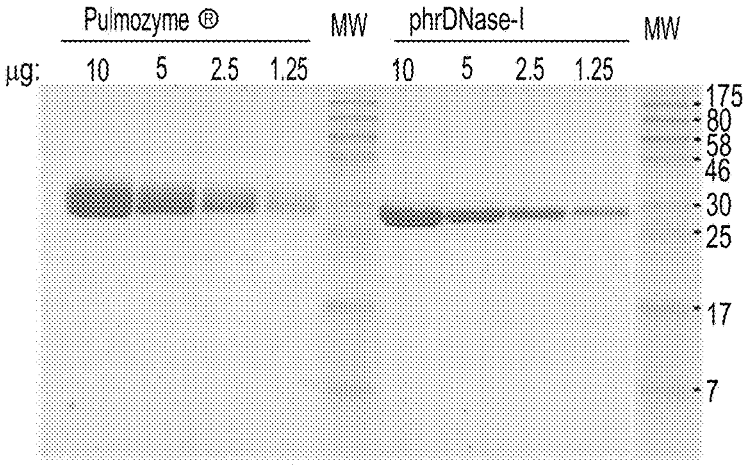
Figure 4:
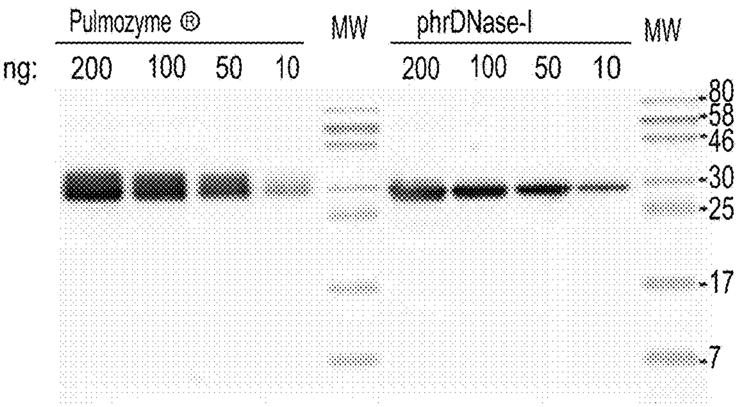
Figure 5A:
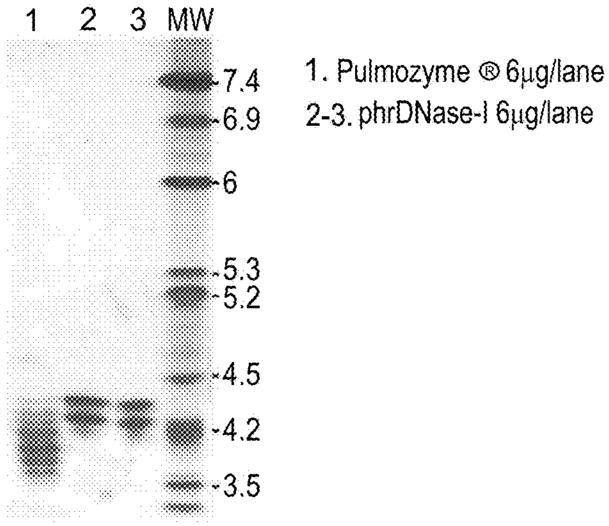
Figure 8C:
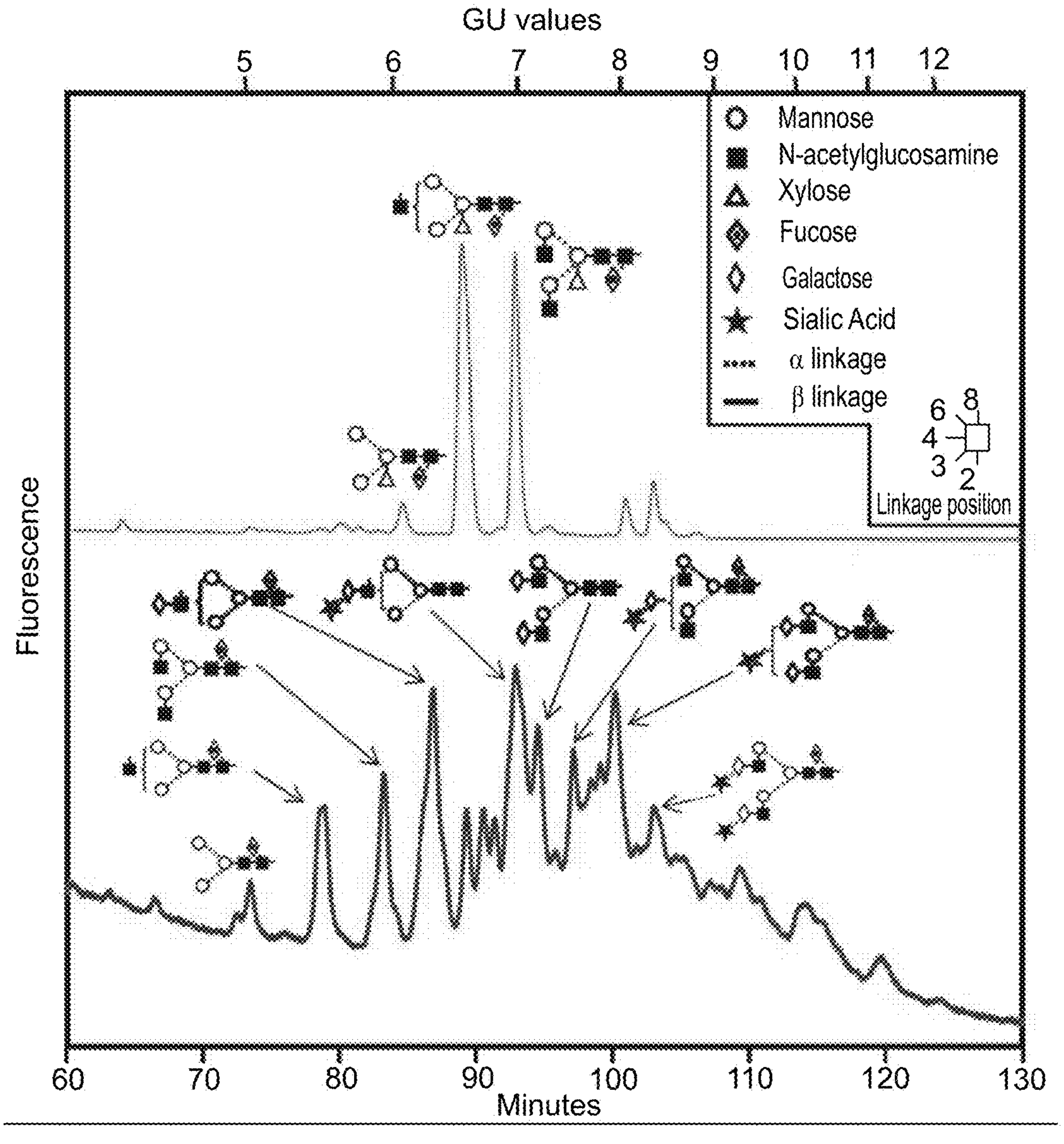
Figure 9A:
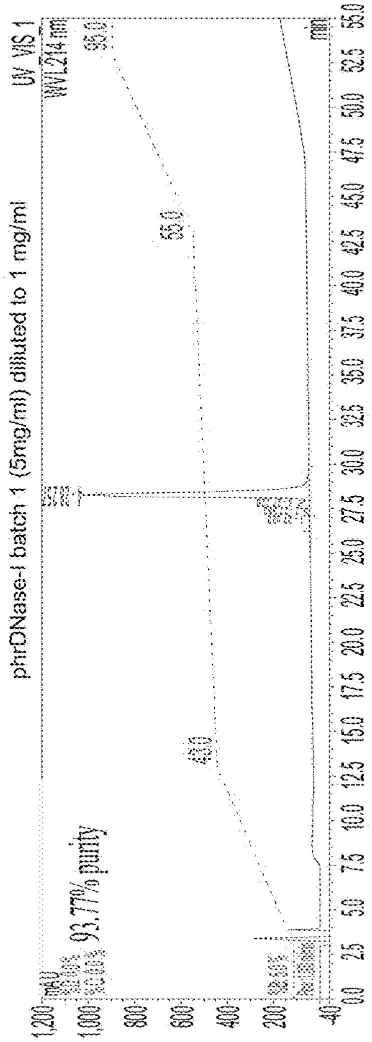
Figure 9B:
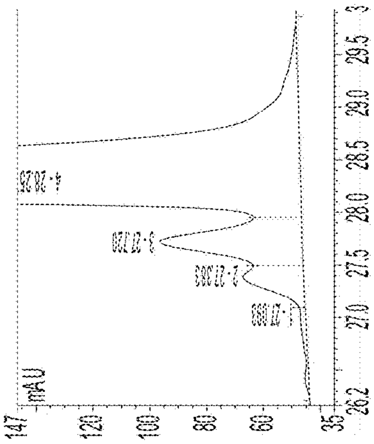
Figure 9C:
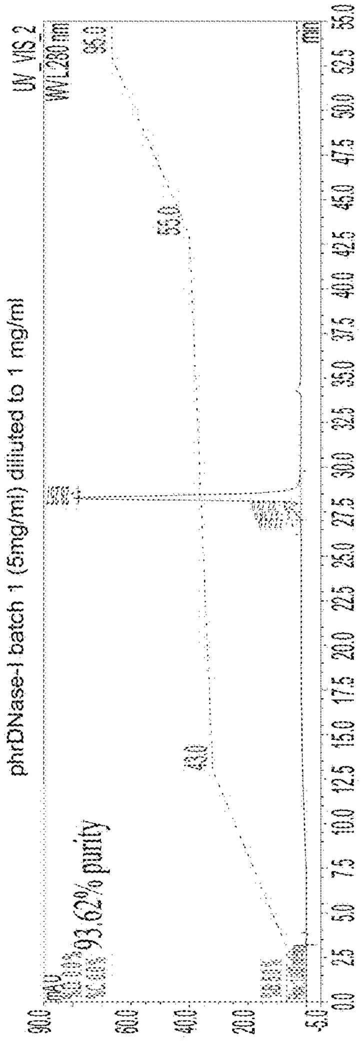
Figure 9D:
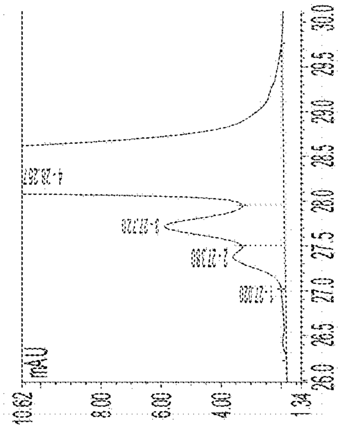

FIG. 1 is an amino acid sequence alignment of the plant recombinant human DNase I (prhDNase I) encoded by the nucleic acid of the invention [SEQ ID NO: 1, sequence (b)], and native human DNase I protein [(GenBank: NM_005223, sequence (a)](SEQ ID NO: 2), including the native signal leader peptide (highlighted in red, SEQ ID NO: 3). The *Arabidopsis* ABPI endoplasmic reticulum targeting signal peptide (SEQ ID NO: 4) is highlighted in green;

FIG. 2 is a graph showing the results of targeting expression of recombinant human DNase I to different plant organelles. rhDNase I was expressed in whole tobacco plants and targeted for secretion (to the apoplast) via an N-terminal ER targeting signal peptide (APO), targeted to the vacuole, via an N-terminal ER targeting signal and a C-terminal vacuolar targeting signal peptide (VAC) and targeted to the endoplasmic reticulum via an N-terminal ER targeting signal peptide and a C-terminal ER retention signal peptide (ER). Activity of rhDNase I in the cells of the tobacco plant was monitored by immunoreactivity (ELISA) and according to catalytic activity (DNA-methyl green assay), adjusted for amount of biomass in sample and expressed as phrDNase I relative to expression in apoplast-targeted cells (100%). Note the significantly greater yield when the rhDNase I is targeted to the apoplast;

FIG. 3 shows an SDS-PAGE gel illustrating the size and purity of plant-expressed rh DNase I. 1.25 μg, 2.5 μg, 5 μg and 10 μg of commercial human DNase (Pulmozyme®) (lanes 1-4, respectively) or purified prh DNase I (lanes 6-9, respectively) were separated on 15% Tris-Glycine SDS-PAGE, stained with Coomassie blue, and to analyzed in comparison to molecular weight standards (lanes 5 and 10). Note the single, predominant band of the plant-expressed enzyme migrating slightly but discernibly faster than that of commercial human DNase (Pulmozyme®), and the absence of detectable protein impurities;

FIG. 4 shows an SDS-PAGE gel illustrating the size, purity and antigenic identity of plant-expressed rh DNase I. 10 ng, 50 ng, 100 ng and 200 ng of commercial human DNase (Pulmozyme®) (lanes 1-4, respectively) or purified prh DNase I (lanes 6-9, respectively) were separated on 15% Tris-Glycine SDS-PAGE, transferred to nitrocellulose membrane, probed with whole antiserum primary antibody obtained from rabbits immunized against Pulmozyme®, and visualized with secondary goat anti-rabbit IgG HRP-conjugated antibody. Note the single, predominant band of the immunoreactive, plant-expressed enzyme migrating and reacting similarly to that of commercial human DNase (Pulmozyme®), and the absence of detectable protein impurities;

FIGS. 5A-5D shows an IEF gel and capillary electropherogram of human DNase (Pulmozyme®) and purified, plant expressed rh DNase I. FIG. 5A shows the resolution of 6 μg of commercial human DNase (Pulmozyme®) (lane 1) or 6 μg of purified, plant expressed rh DNase I (lanes 2-3) on an isoelectric focusing gel. FIG. 5B shows the resolution of 8 μg of commercial human DNase (Pulmozyme®) (lane 3) or 8 μg of purified, plant expressed rh DNase I from a different line of BY2 cells expressing the prhDNase I (lane 2) on an isoelectric focusing gel. Note that Pulmozyme® resolves into multiple bands with isoelectric points (pI) between pI 3.5 and pI 4.5 in a pH gradient of pH 3 to pH 7, while in both of the purified, plant expressed rh DNase I preparations the DNase I resolved at an isoelectric point (pI) between pI 4.2 and pI 4.5, in two major bands and one minor band. Electrophoresis conditions included 100 mV-1 hour, 200 mV-1 hour and 500 mV-1.5 hours. Lanes 4 (FIG. 5A) and lane 1 (FIG. 5B) contain protein standards for comparison. FIG. 5D is an electropherogram of image capillary isoelectric focusing (scale=pI 3.3-6.1) analysis of purified, plant expressed rh DNase I, showing the resolution of the prh DNase I as observed in the IEF gel [one major peak (3) at pI 4.41 and two minor peaks (4 and 5) at pI 4.27 and 4.21). 1 and 2 are pI markers 5.85 and 3.59. FIG. 5C is an electropherogram of the blank scale with pI markers 1 and 2;

FIGS. 6A-6B show the molecular mass analysis of purified, plant expressed rh DNase I by mass spectrometry using 2.5 micrograms of the purified prh DNase I using a matrix-assisted laser desorption ionization time-of-flight (MALDI-ToF) mass spectrometer, with sinapinic acid as a matrix. FIG. 6A showing the entire spectrum from 20000 to 180000 m/z and FIG. 6B showing an enlarged segment of the prh-DNaseI peak at about 32000 m/z;

FIG. 7 is a figure representing a putative amino acid sequence of the purified, plant expressed rh DNase I (SEQ ID NO: 5), derived from the sequences of overlapping peptides produced by partial proteolytic digestion (see SEQ ID NOs: 17-276) and separated and analyzed on RP-HPLC and mass spectrometry. Unconfirmed amino acids are marked in red, glycosylation sites are underlined and the N-terminal Glycine residue is marked in green;

FIGS. 8A-8C represent analysis of the glycan structure of the purified, plant expressed rh DNase I, as determined by exoglucosidase digestion and NP-HPLC analysis of the resulting de-glysosylated polypeptides. FIG. 8A is an NP-HPLC profile of total glycans released following PNGase A digestion of the glycosylated prhDNase I, derived from three separate exemplary batches of prhDNase I. The numbers above the discrete peaks correspond to specific glycan structures illustrated in FIG. 8B. FIG. 8B is a chart showing individual glycan structures released from prhDNase I by PNGase A digestion, and their relative abundance (in percentages) from total released glycans, for each of the three exemplary batches tested. Note the predominance of two main glycan peaks representing a high percentage of glycan structures (over 80%) containing mannose 3-β-(1,2) xylose-α-(1,3) fucose [Fc(3)M3X] and/or mannose 4-α-(1,2) xylose. FIG. 8C shows an NP-HPLC profile of total glycans released from prhDNase I using PNGase A endoglycosidase (top) compared to the profile of N-linked glycans released from Pulmozyme® using PNGase F endoglycosidase (specific to high mannose glycans) showing a multitude of glycan variations. The major peaks are annotated with corresponding glycan structures. Note the wide variation in glycosylation pattern found in Pulmozyme®, due to the abundance of bi- and tri-antennary glycans, and sialic acid residues.

Figure 10A:
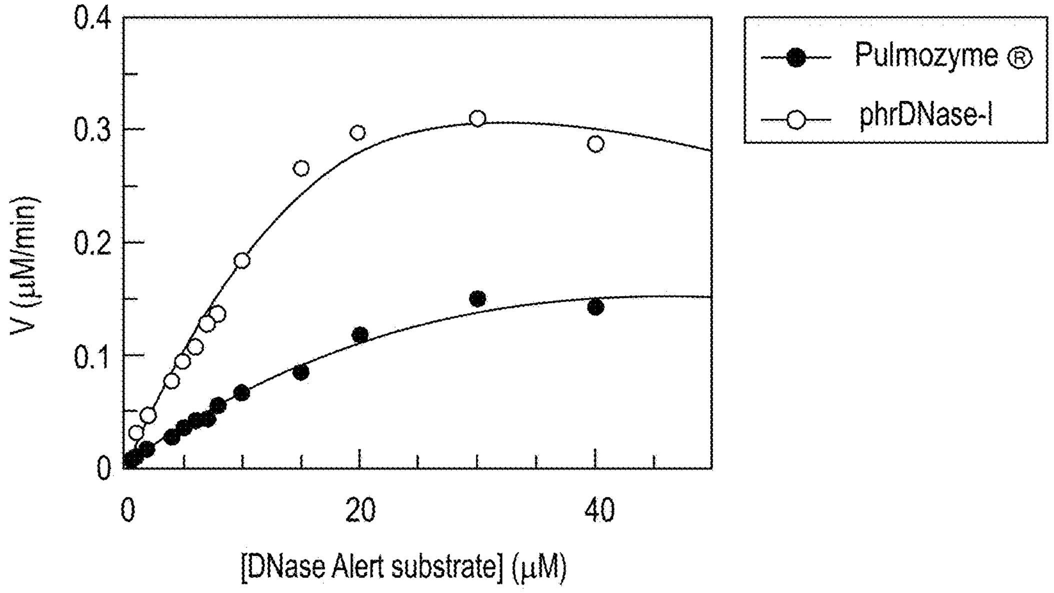
Figure 10B:
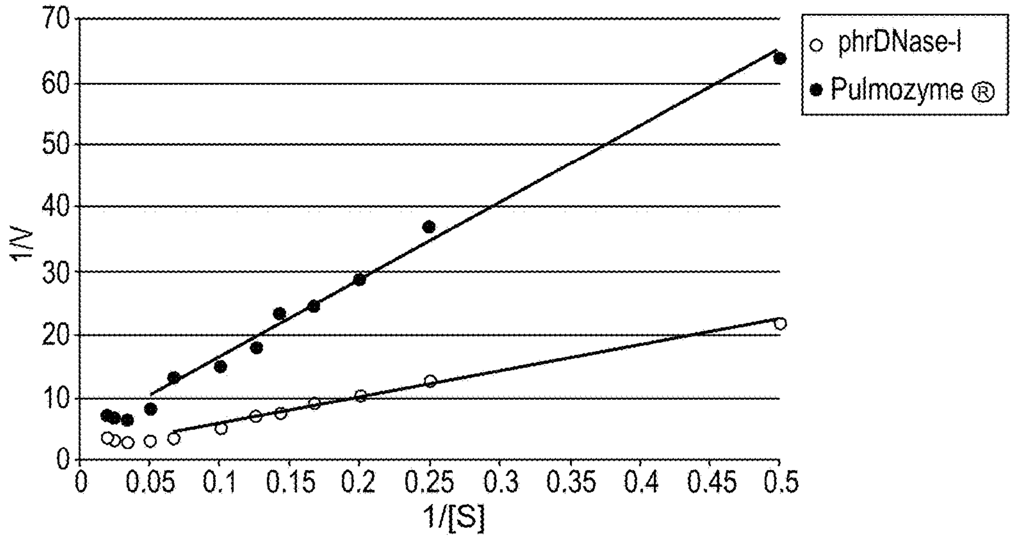
Figure 11:
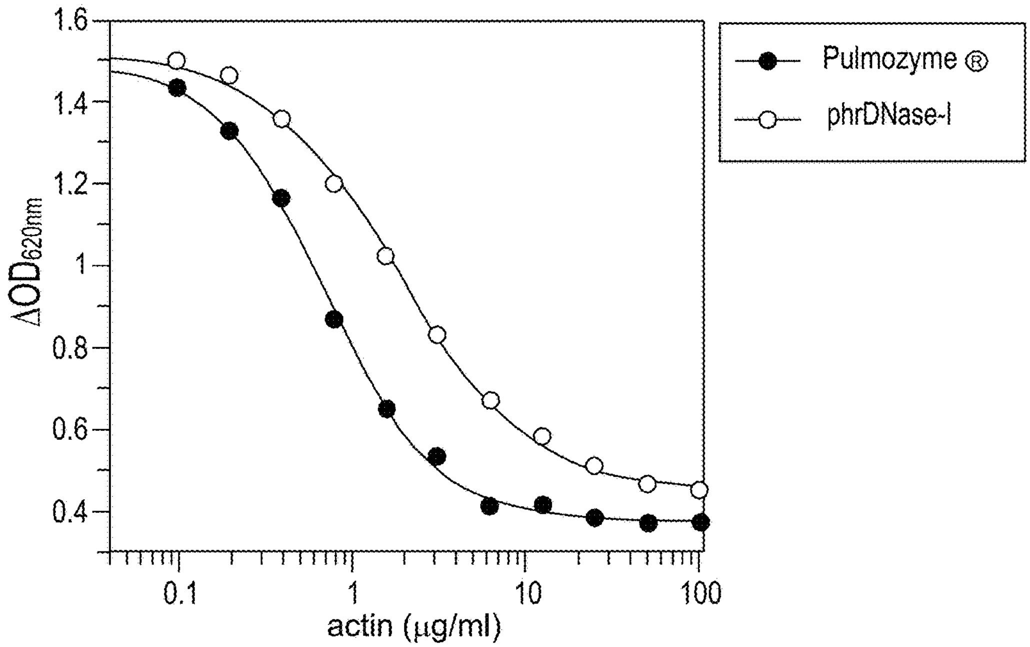
Figure 12A:
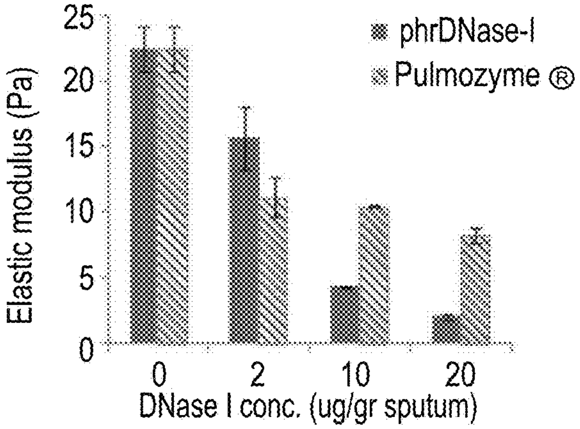
Figure 12B:
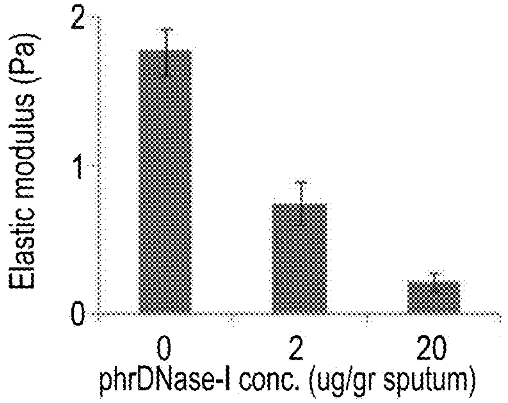
Figure 12C:
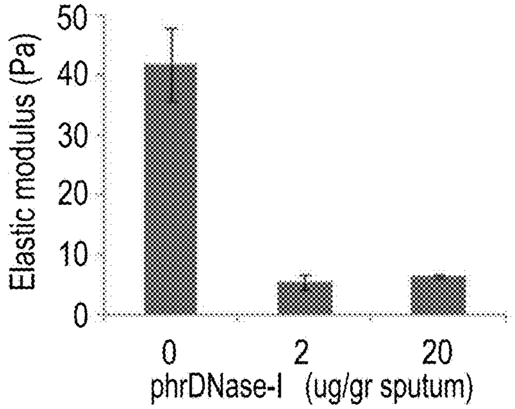
Figure 12D:
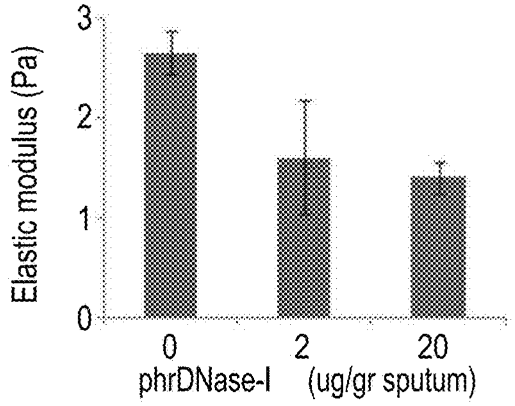
Figure 13A:
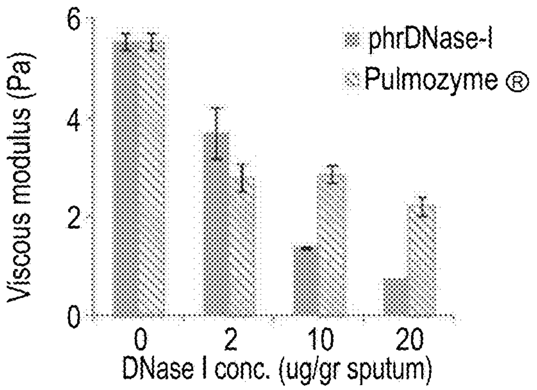
Figure 13B:
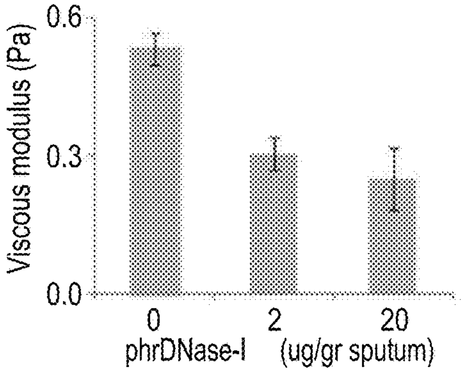
Figure 13C:
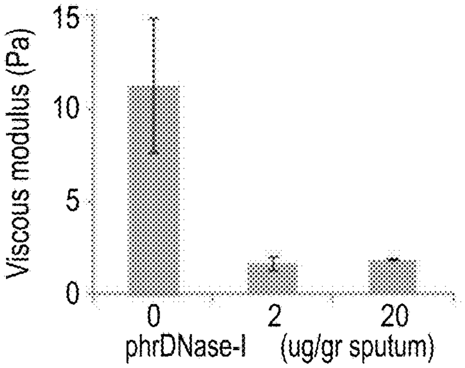
Figure 13D:
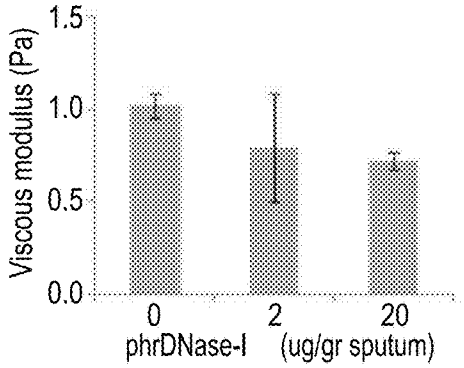
Figure 14A:
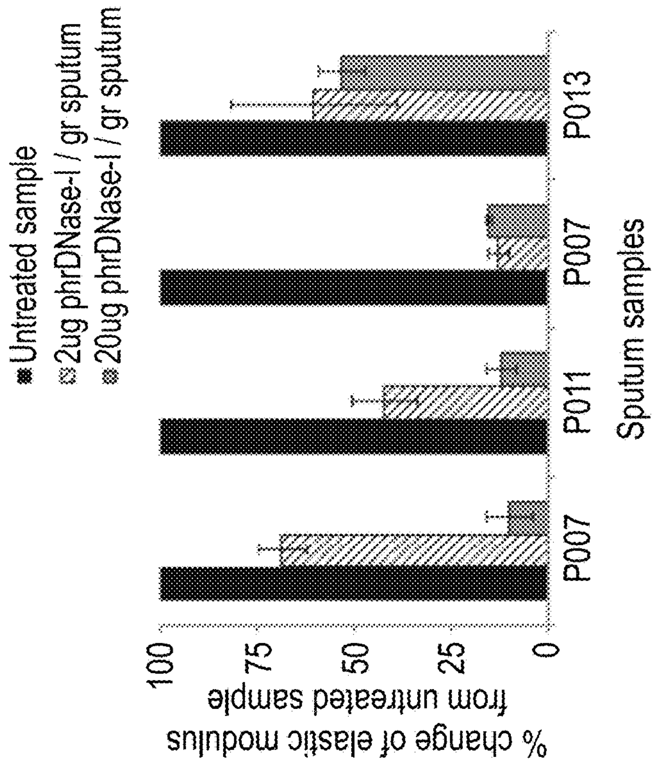
Figure 14B:
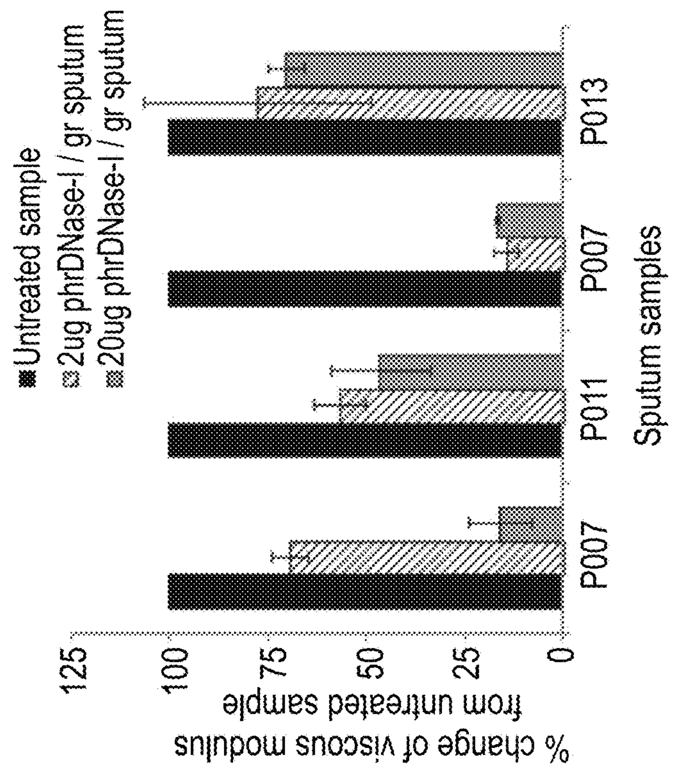
Figure 15:
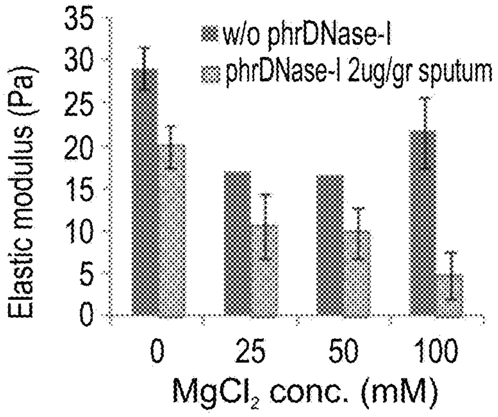
Figure 16:
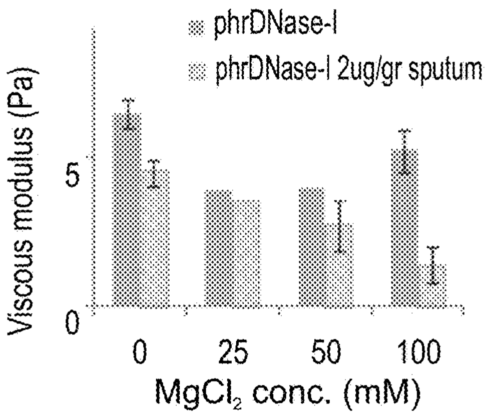
Figure 17:
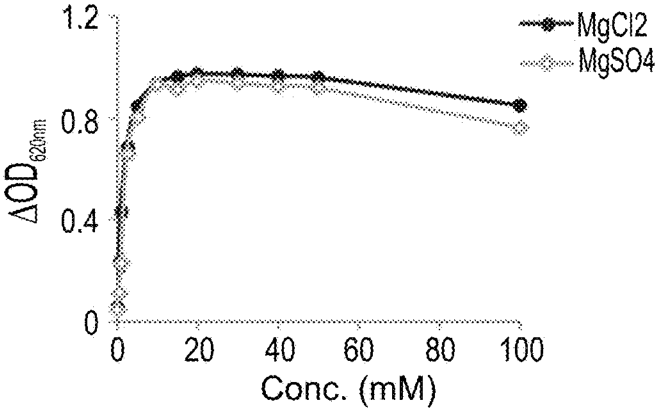
Figure 18A:
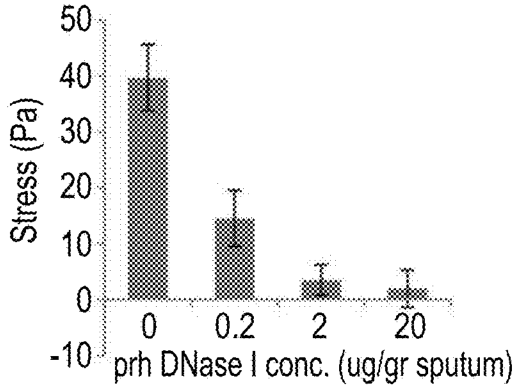
Figure 18B:
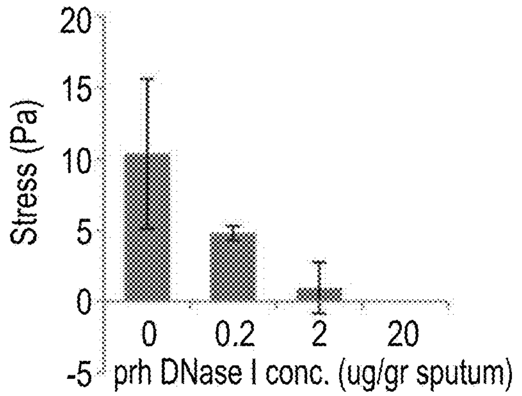
Figure 18C:
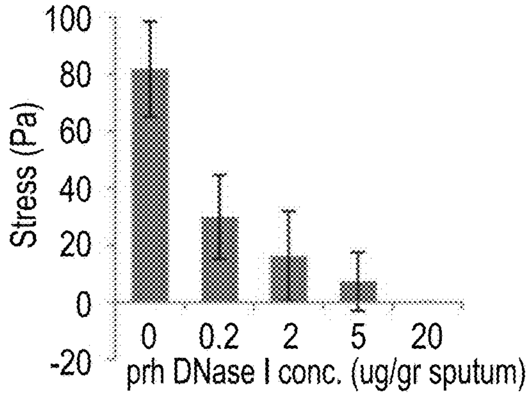
Figure 18D:
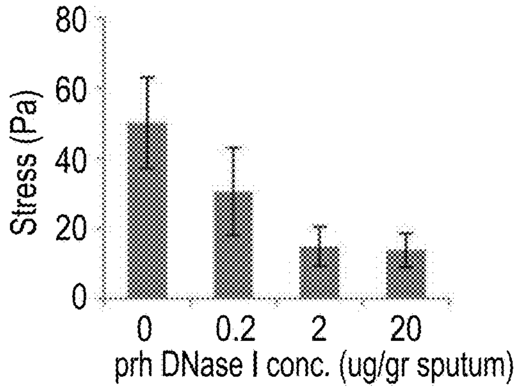
Figure 19A:
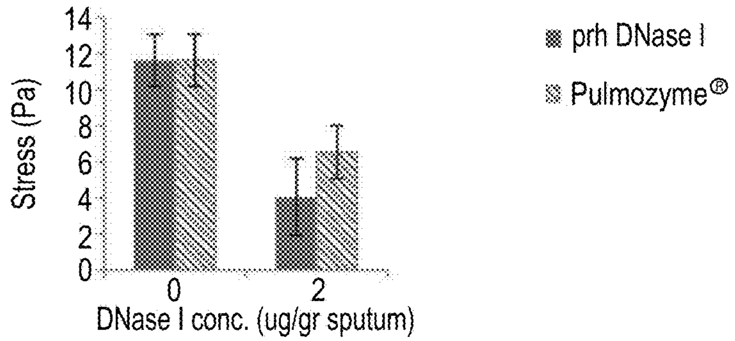
Figure 19B:
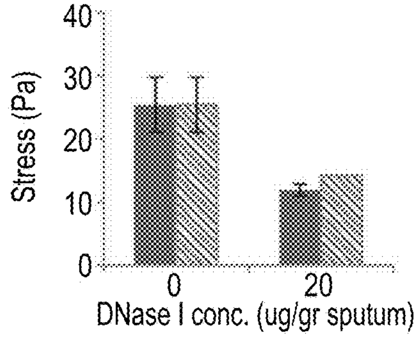
Figure 19C:
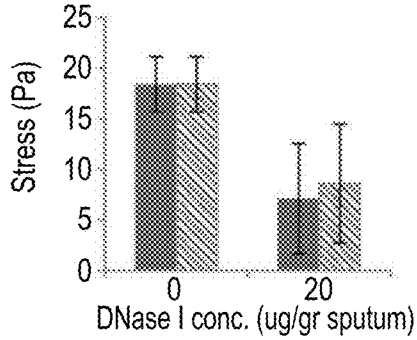
Figure 19D:
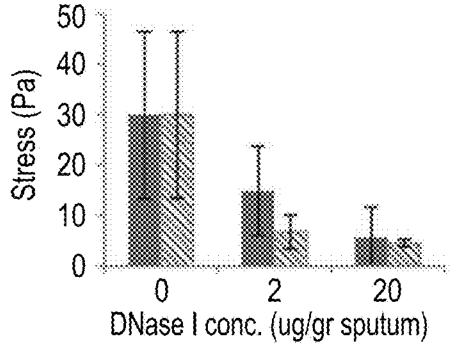

FIGS. 9A-9D are chromatograms of RP-HPLC of purified, plant expressed rh DNase I, analyzed at 214 nm (FIGS. 9A, 9B) and 280 nm (FIGS. 9C, 9D), indicating a to preparation of the prh DNase I having less than 7% impurities (93.77% pure measured at 214 nm, and 93.62% pure measured at 280 nm). Insets (FIGS. 9B and 9D) are expanded views of the prh DNase I peak at 214 nm and 280 nm, respectively;

FIGS. 10A-10B are graphs representing substrate inhibition kinetic plots of purified prh DNase I (open circles O) and commercial human DNase (Pulmozyme®) (closed circles ●), using the DNaseAlert™ fluorometric substrate detected at 535 nm and 565 nm FIG. 10A is a plot of the initial velocity as a function of substrate concentration. Note the superior kinetics (greater $V_{max}$, lower $K_M$, e.g. higher specific activity) of the purified prh DNase I. FIG. 10B is a double reciprocal plot of initial velocity as a function of substrate concentration. $K_M$ and $V_{max}$ values were calculated using the following linear regression equations (plotted at substrate concentration of 2-μM) and $R^2$ values: prh DNase I: y=41.377x+1.8693, $R^2$=0.9894; Pulmozyme®: y=120.17x+4.8316, $R^2$=0.9921, indicating substrate-inhibition-like kinetics for both prh DNase I and Pulmozyme®;

FIG. 11 is an activity plot of purified, plant expressed rh DNase I (open circles O) and commercial human DNase (Pulmozyme®) (closed circles ●), illustrating resistance to actin inhibition of DNase I activity. ΔOD (620 nm) is plotted as a function of G-actin concentration, using the Methyl Green substrate, to yield $IC_{50}$ values. Note the reduced susceptibility to G-actin inhibition of the purified prh DNase I, compared to that of commercial human DNase (Pulmozyme®);

FIGS. 12A-D are histograms illustrating the effect of increasing concentrations of DNase I on the elastic modulus of sputum from Cystic Fibrosis patients, determined using time-sweep measurements with a rheomoter (HAAKE RheoStress I, Thermo Fisher Scientific GmBH, Germany). FIG. 12A represents a comparison of the effect of purified, plant expressed rh DNase I (dark bars) and commercial human DNase (Pulmozyme®) (hatched bars) on the elastic modulus of CF patient sputa, measured at 2, 10 and 20 μg DNase I/gr sputum. DNA content of the sputum was 4.66 μg DNA/gr sputum. Each value represents at least 2 determinations measured from each sputum sample. FIGS. 12B-12D show the effect of prhDNase I on the elastic modulus of sputa collected from individual patients. Note the pronounced, superior and consistent, dose-dependent reduction of sputum elastic modulus following incubation with prh DNase I, to as compared to the Pulmozyme®;

FIGS. 13A-D are histograms illustrating the effect of increasing concentrations of DNase I on the viscous modulus of sputum from Cystic Fibrosis patients, measured using time-sweep technique with a rheomoter (HAAKE RheoStress I, Thermo Fisher Scientific GmBH, Germany). FIG. 13A represents a comparison of the effect of purified, plant expressed rh DNase I (dark bars) and commercial human DNase (Pulmozyme®) (hatched bars) on the viscous modulus of CF patient sputa, measured at 2, 10 and 20 μg DNase I/gr sputum. DNA content of the sputum was 4.66 μg DNA/gr sputum. Each value represents at least 2 determinations measured from each sputum sample. FIGS. 13B-13D shows the effect of prhDNase I on the viscous modulus of sputa collected from individual patients. Note the pronounced, superior and consistent, dose-dependent reduction of sputum viscous modulus following incubation with prh DNase I, as compared to the Pulmozyme®;

FIGS. 14A and 14B are histograms representing the effect of prhDNase I on the rheological properties of sputum from Cystic Fibrosis patients, measured using time sweep technique, expressed as percent change rheological properties (elastic modulus, FIG. 14A and viscous modulus, FIG. 14B) compared to an untreated sample. FIG. 14A shows the percent change of elastic modulus of the sputa of 4 individual patients (black bars=untreated control samples; hatched bars=2 μg prhDNase I; gray bars=20 μg prhDNase I). FIG. 14B shows the percent change of viscous modulus of the sputa of 4 individual patients (black bars=untreated control samples; hatched bars=2 μg prhDNase I; gray bars=20 μg prhDNase I). Note the consistent pronounced reduction in rheological properties following incubation of the sputa with prh DNase I;

FIG. 15 is a histogram illustrating the synergic effect of purified, plant expressed rh DNase I on the reduction of CF sputum elastic modulus by Magnesium ($MgCl_2$) (0, 25, 50 and 100 mM), measured using time sweep technique, with rheomoter (HAAKE RheoStress I, Thermo Fisher Scientific GmBH, Germany). Elastic modulus of the sputum was determined at indicated concentrations of $Mg^{2+}$ (mM $MgCl_2$) in the presence (cross-hatched bars) or absence (dark bars, buffer only) of prh DNase I (2 μg prh DNase I/gr sputum). Each value represents at least 2 determinations. Note the synergic reduction of sputum elastic modulus following incubation with the prh DNase I and Magnesium, as compared to Magnesium alone;

FIG. 16 is a histogram illustrating the effect of Magnesium salts on DNase I reduction of CF sputum viscous modulus. FIG. 16 shows the synergic effect of purified, plant expressed rh DNase I on the reduction of CF sputum viscous modulus by Magnesium ($MgCl_2$) (0, 25, 50 and 100 mM), measured with a rheomoter (HAAKE RheoStress I, Thermo Fisher Scientific GmBH, Germany). Viscous modulus of the sputum was determined at the indicated concentrations of $Mg^{2+}$ (mM $MgCl_2$) in the presence (cross hatched bars) or absence (grey bars, buffer only) of prh DNase I (2 μg DNase I/gr sputum). Each value represents at least 2 determinations. Note the synergic reduction of sputum viscous modulus following incubation with the prh DNase I and Magnesium, as compared to Magnesium alone;

FIG. 17 is a graph illustrating the effect of different Magnesium salts on the DNase catalytic activity of purified, plant expressed rh DNase I. Catalytic activity of rh DNase I was measured in the presence of increasing concentrations (0.5-100 mM) of Magnesium chloride ($MgCl_2$, closed circles ●) or Magnesium sulphate ($MgSO_4$, open diamonds ◇), using the methyl green substrate and expressed as the change in absorbance at 630 nm (Δ OD 630 nm) after 3 hours incubation with the enzyme. Note that neither magnesium salt inhibited rh DNase I activity up to 50 mM, and that rh DNase I activity was only slightly impaired by $MgSO_4$ at 100 mM.

Figure 20A:
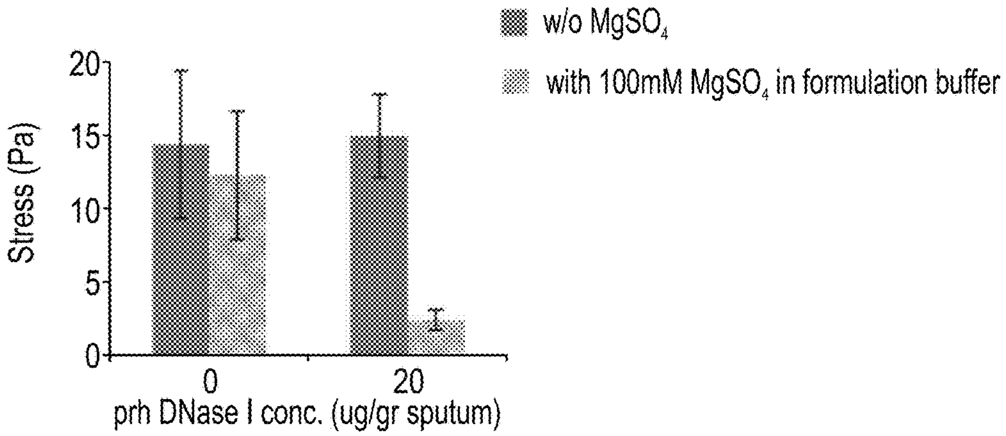
Figure 20B:
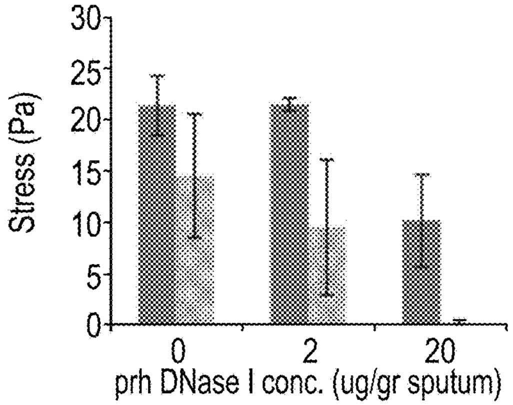
Figure 20C:
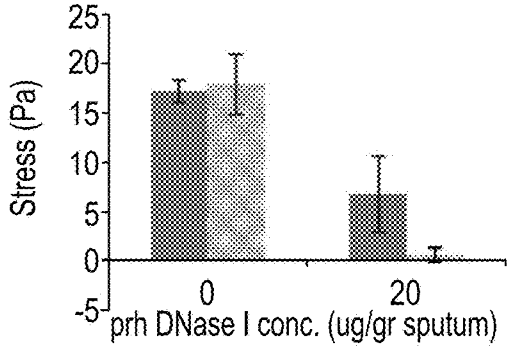
Figure 21:
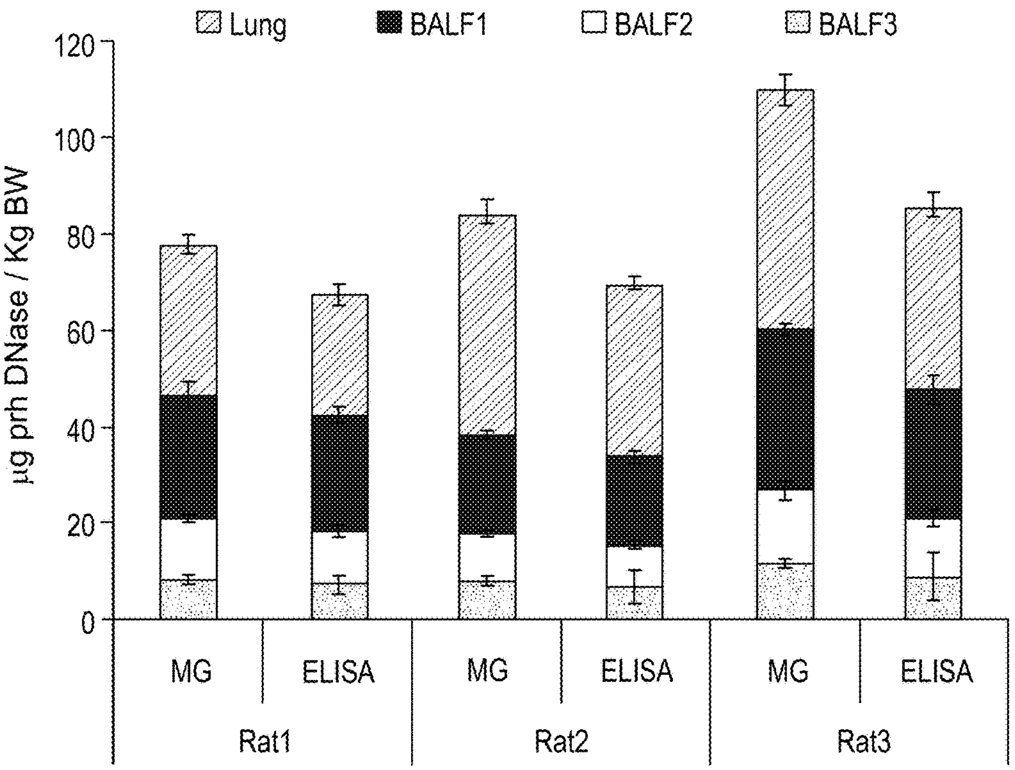

FIGS. 18A-18D are histograms illustrating the effect of increasing concentrations of DNase I on the rheological properties of sputum from Cystic Fibrosis patients, determined using the stress sweep technique with a rheomoter (HAAKE RheoStress I, Thermo Fisher Scientific GmBH, Germany), expressed as the stress (Pa) at cross-over of elastic and viscous modules (phase angle=45°). FIGS. 18A-18D represents a comparison of the effect of purified, plant expressed rh DNase I (dark bars) and commercial human DNase (Pulmozyme®) (hatched bars) on the rheological properties of four individual CF patient sputa, measured at 0.2, 2 and 20 μg DNase I/gr sputum. DNA content of the sputum was 3.09 mg DNA/gr sputum, 3.15 mg DNA/gr sputum, 8.36 mg DNA/gr sputum and 3.89 mg DNA/gr sputum (FIGS. 18A-18D, respective). Each value represents at least 2 determinations measured from each sputum sample. Note the pronounced and consistent, dose-dependent reduction in cross-over stress values following incubation with prh DNase I;

FIGS. 19A to 19D are histograms representing the effect of prhDNase I and to Pulmozyme® on the rheological properties of sputum from four different Cystic Fibrosis patients (19A-19D), measured using stress sweep technique, expressed as the stress (Pa) at cross-over of elastic and viscous modules (phase angle=45°). DNA content of the sputum was 2.16 mg DNA/gr sputum, 2.63 mg DNA/gr sputum, 3.45 mg DNA/gr sputum and 4.17 mg DNA/gr sputum (FIGS. 19A-19D, respective) Black bars=prhDNase I; hatched bars=Pulmozyme®. DNase I concentration (0, 2 or 20 μg DNase I/gr sputum). Note the consistent pronounced reduction in rheological properties following incubation of the sputa with prh DNase I, significantly outperforming Pulmozyme® in 3 out of the four patients;

FIGS. 20A-20C are histograms illustrating the effect of Magnesium salts and DNase I on the rheological properties of CF sputum samples from three different Cystic Fibrosis patients, measured using the stress sweep technique with a rheomoter (HAAKE RheoStress I, Thermo Fisher Scientific GmBH, Germany), expressed as the stress (Pa) at cross-over of elastic and viscous modules (phase angle=45°). FIG. 20A-patient A (1.84 mgDNA/g sputum), FIG. 20B-patient B (3.46 mgDNA/g sputum) and FIG. 20C (2.39 mg DNA/g sputum). Dark columns are measurements without Magnesium, grey columns are represent measurement with 100 mM $MgSO_4$, measured at 0 (control) 2 and 20 μg DNase I/gr sputum. Each value represents at least 2 determinations measured from each sputum sample. Note the pronounced and synergistic disruption of sputum elastic structure following incubation with prh DNase I and $MgSO_4$;

FIG. 21 is a histogram illustrating the measured prh DNase I content in lung and bronchial lavage from rats exposed to prh DNase I aerosol by "nose-only" inhalation exposure system. Values in columns are the sums of the recovery from lungs (diagonal lines), bronchio-alveolar lavage 1 (black), bronchio-alveolar lavage 2 (white) and bronchio-alveolar lavage 3 (stippled) for each of the three rats. Note the consistent correlation between the values measured by immunological (ELISA) and catalytic (MG) assays.

DESCRIPTION OF SPECIFIC EMBODIMENTS OF THE INVENTION

The present invention, in some embodiments thereof, relates to inhalable pharmaceutical composition comprising human DNase I as an active ingredient, suitable for pulmonary administration by inhalation by means of a metered dose inhaler or to nebulizer, processes for the preparation of such a composition, and methods of using such a composition for the prevention and/or treatment of a wide range of conditions including respiratory disorders such as cystic fibrosis (CF), asthma and chronic obstructive pulmonary disease (COPD), as well as other, non-respiratory disorders.

It is to be understood that the invention is not necessarily limited in its application to the details set forth in the following description or exemplified by the Examples. The invention is capable of other embodiments or of being practiced or carried out in various ways.

According to one aspect of some embodiments of the present invention there is provided an inhalable pharmaceutical composition for pulmonary administration comprising a human DNase I protein and a physiologically acceptable pharmacologically-inert liquid carrier.

The present inventors have devised an inhalable pharmaceutical composition comprising human DNase I, suitable for pulmonary administration and capable of providing catalytically active human DNase I for nucleolytic digestion of extracellular DNA found in secretions, fluids and tissues of the airways, as well as fluids, secretions and tissues accessible via systemic circulation. Such liquid have been found effective for providing catalytically active human DNase I protein to the sputum and other pulmonary secretions, resulting in reduction in the DNA content and improving the rheological properties of the sputum and other secretions. When comprising a plant expressed recombinant human DNase I, the efficacy of the liquid inhalable compositions of the invention in treating pulmonary secretions can be enhanced due to the surprisingly favorable kinetic properties and resistance of the prh DNase I to actin inhibition, thereby enhancing the therapeutic value of the human DNase I when provided in such a liquid inhalable pharmaceutical composition.

As used herein, the term "physiologically inert . . . carrier" refers to a carrier whose administration to the subject does not result in a physiological response or reaction associated with the response or reaction of the subject to the active ingredient, in this case, the DNase I. In some embodiments, the "physiologically inert . . . carrier" is devoid of any effect on the pharmaceutical activity of the active ingredient, e.g. the DNase I. The term "pharmaceutically acceptable" as used herein means that the compound or composition is suitable for administration to a subject to achieve the to treatments described herein, without undue deleterious side effects in light of the severity of the disease and necessity of the treatment.

As used herein, the term "liquid carrier" refers to the carrier being in a liquid form, making the pharmaceutical composition, and the active ingredient human DNase I, available for dispersion into fine, moist particles and administration as an aerosol, a mist, a vapor and the like for inhalation. In some embodiments, the liquid carrier is selected from the group consisting of water, an aqueous alcoholic solution, perfluorocarbon and saline.

Particles comprised of active compound for practicing the present invention should include particles of respirable size: that is, particles of a size sufficiently small to pass through the mouth and larynx upon inhalation and into the bronchi and alveoli of the lungs. In general, particles ranging from about 1 to 10 microns in size (more particularly, less than about 5 microns in size) are respirable. Particles of non-respirable size which are included in the aerosol or mist tend to deposit in the throat and be swallowed, and the quantity of non-respirable particles in the aerosol or mist is preferably minimized See, e.g., U.S. Pat. No. 5,292,498 to Boucher, US20070044793 to Kleinstreuer et al or US20110056492 to Longest et al.

The pharmaceutical composition can be prepared in any aqueous carrier, vehicle, or solution so as to provide a composition that is pharmaceutically suitable for in vivo administration. Methods of preparing aqueous solutions are well known to one of ordinary skill in the art. Preferably, the aqueous solution is water, or a physiologically acceptable aqueous solution containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS), and solutions containing other buffers which are compatible with endonucleases. The compositions may also contain sodium chloride and glucose or mannitol to make the solution isotonic. The composition may contain suitable auxiliary components such as pH, osmolarity and tonicity adjusting agents.

For pulmonary administration, the composition is formulated into a solution, e.g., water or isotonic saline, buffered or unbuffered, or as a suspension, at an appropriate concentration for pulmonary administration as an aerosol, mist, vapor and to the like. Preferably, such solutions or suspensions are isotonic relative to pulmonary secretions and of about the same pH, ranging e.g., from about pH 4.0 to about pH 8.0 or, from pH 6.5 to pH 7.5. Buffers should be physiologically compatible and include, simply by way of example, phosphate buffers. For example, a representative DNase I for pulmonary administration (Pulmozyme®) is buffered to a pH of about 6.3. One skilled in the art can readily determine a suitable saline content and pH for an inert aqueous solution for pulmonary administration.

Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compositions may contain minor amounts of polymers, surfactants, or other excipients well known to those of the art. In this context, "minor amounts" means no auxiliary agents or substances are present that might affect or mediate the activity of the active ingredients in the airways or on extracellular DNA.

The inhalable composition may comprise an adsorption enhancer.

The enhancer used can be any of a number of compounds which act to enhance absorption through the layer of epithelial cells lining the alveoli of the lung, and into the adjacent pulmonary vasculature. The enhancer can accomplish this by any of several possible mechanisms:

(1) Enhancement of the paracellular permeability of DNase by inducing structural changes in the tight junctions between the epithelial cells;

(2) Enhancement of the transcellular permeability of DNase by interacting with or extracting protein or lipid constituents of the membrane, and thereby perturbing the membrane's integrity;

(3) Interaction between enhancer and DNase which increases the solubility of DNase in aqueous solution. This may occur by preventing formation of DNase aggregates, or by solubilizing DNase molecules in enhancer micelles;

(4) Decreasing the viscosity of, or dissolving, the mucus barrier lining the alveoli and passages of the lung, thereby exposing the epithelial surface for direct absorption of the DNase.

Enhancers may function by only a single mechanism set forth above, or by two or more. An enhancer which acts by several mechanisms is more likely to promote efficient absorption of DNase than one which employs only one or two. For example, surfactants are a class of enhancers which are believed to act by all four mechanisms listed above. Surfactants are amphiphilic molecules having both a lipophilic and a hydrophilic moiety, with varying balance between these two characteristics. If the molecule is very lipophilic, the low solubility of the substance in water may limit its usefulness. If the hydrophilic part overwhelmingly dominates, however, the surface active properties of the molecule may be minimal. To be effective, therefore, the surfactant must strike an appropriate balance between sufficient solubility and sufficient surface activity.

As used herein the term "human DNase I protein" refers to a human DNase I (deoxyribonuclease I; EC 3.1.21.1; DNase I) polypeptide. Human DNase I is classified as an endonuclease, which cleaves DNA to produce 5' phosphodi- and 5' phosphooligonucleotide end products, with a preference for double stranded DNA substrates and alkaline pH optimum. Other members of the DNase I family of endonucleases are DNase X, DNase lambda, DNASIL2 and tear lipocalin in humans.

DNase I is also known, inter alia, as alkaline DNase, bovine pancreatic (bp) DNase, DNase A, DNA phosphatase and DNA endonuclease, for example, in *Bos taurus*. According to some embodiments of the invention, the human DNase I protein is the mature human DNase I protein, having the amino acid sequence as set forth in SEQ ID NO: 6. It will be appreciated that the human DNase I protein can be a modified human DNase I protein, having an amino acid sequence different than that of SEQ ID NO: 6 while maintaining characteristic structure and/or function of DNase I. One non-limiting example of a modified human DNase I protein encoded by the expression vector of the invention is SEQ ID NO: 5.

According to yet other embodiments of the invention, the inhalable pharmaceutical composition comprises a variant human DNase protein. Variant human DNase proteins, having altered catalytic and/or other biochemical and structural properties, such as altered actin affinity, cofactor requirements, pH optimum, increased shelf life in storage and the like, enhanced recombinant expression or fusion proteins have been disclosed (see, for example, EC 3.1.21.2; EC 3.1.21.3; EC 3.1.21.4; EC 3.1.21.5; EC 3.1.21.6 and EC 3.1.21.7). Suitable modified DNase I polypeptides include, but are not limited to DNase polypeptides disclosed in U.S. Pat. Nos. 6,348,343; 6,391,607; 7,407,785; 7,297,526 and WO2008/039989.

According to some embodiments, the inhalable pharmaceutical composition formulation comprises a DNase-like protein polypeptide. The term "DNase I-like protein" refers to an enzyme having an enzyme classification of EC 3.1.21.x, where "x" is a positive integer. As used herein, "DNase I-like proteins" are a subset of "DNases."

The amino acid sequences of many DNases, and the coding sequences encoding such DNase proteins are well known in the art, available from public genomic databases such as GenBank, SwissProt, EMBL and many others.

According to yet further embodiments of the invention, the inhalable pharmaceutical composition comprises a human DNase I protein comprising an N-terminal glycine residue, for example, SEQ ID NO: 5.

According to some embodiments of the invention, the inhalable pharmaceutical composition comprises a recombinant human DNase I protein. As used herein, the term "recombinant human DNase I protein" refers to a human DNase I protein exogenously produced in a cell transformed with, and expressing an exogenous human DNase I coding sequence. Non-limiting examples of recombinant human DNase I protein are detailed herein, include the mammalian cell-expressed Pulmozyme® and a plant-expressed human recombinant DNase I (SEQ ID NO: 5).

According to some embodiments of the invention, the inhalable pharmaceutical composition comprises a human DNase I protein comprising the amino acid sequence as set forth in SEQ ID NO: 5, expressed in plant cells. When plant human recombinant DNase I (phr DNase I) was subjected to controlled proteolytic digestion, mass spectrometry of the resulting oligopeptides revealed that the prh DNase I polypeptide could be characterized by a group of overlapping peptide fragments, which together indicated that the full length recombinant human DNase I expressed by the plant cells was identical, in amino acid sequence, to that of native human DNase I, with the addition of a N-terminal glycine residue (see Example 2 and Tables V and Va, hereinbelow). Further analysis of the amino acid sequence confirmed the accuracy of the sequence and identity with the native human DNase I. Thus, according to some embodiments of some aspects of the invention, the inhalable pharmaceutical composition comprises a prh DNase I comprising a plurality of overlapping DNase I protein peptide fragments, the fragments having the amino acid sequence as set forth in SEQ ID NOs. 17-276 and 278-291. In some further embodiments, the prh DNase I has an additional N-terminal glycine residue, and in other embodiments, the prh DNase I is devoid of an N-terminal glycine residue.

According to some embodiments of some aspects of the invention, the inhalable pharmaceutical composition comprises a prh DNase I having a molecular mass of about 30 kD, as measured by SDS-PAGE, and about 32 kD, as measured by mass spectrometry. In yet further embodiments, the inhalable pharmaceutical composition comprises a glycosylated prh DNase polypeptide, comprising a polypeptide moiety having a molecular mass of about 29 kD.

As shown in Examples 2 and 3, prh DNase I is fully cross-reactive with anti-human recombinant DNase I antiserum raised against mammalian-cell expressed recombinant human DNase I (e.g. Pulmozyme®), for example, as detected by Western blotting of the gel-separated plant-expressed recombinant human DNase I (see FIG. 4) and with ELISA (see Example 3). Thus, according to some embodiments, the inhalable pharmaceutical composition comprises a prh DNase I protein which is immunoreactive with anti-human DNase I anti-serum.

In some embodiments the prh DNase I protein is characterized by two major isoforms with isoelectric points between 4.2 and 4.5. In other embodiments, the plant-expressed recombinant human DNase I protein is further characterized by a minor isoform with a pI between 4.2 and 3.5.

According to some embodiments of some aspects of the invention, the inhalable pharmaceutical composition comprises a purified prh DNase I protein, characterized by a purity of at least 85%, at least 87%, at least 90%, at least 91%, at least 91.5%, at least 92%, at least 92.5%, at least 93%, at least 93.1%, at least 93.2%, at least 93.3%, at least 93.4%, at least 93.5%, at least 93.6%, at least 93.7%, at least 93.8%, at least 93.9%, at least 94%, at least 94.5%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, in a range of at least 92.0-99.8% or 100% purity. In some embodiments, purity of the plant-expressed recombinant to human DNase I protein is measured by HPLC.

In some embodiments the plant-expressed recombinant human DNase I composition comprises impurities derived from the plant host cell, such as, but not limited to nucleic acids and polynucleotides, amino acids, oligopeptides and polypeptides, glycans and other carbohydrates, lipids and the like. In some embodiments the host-cell derived impurities comprise biologically active molecules, such as enzymes. In other embodiments, the plant-expressed recombinant human DNase I composition comprises plant beta-N-acetylhexosaminidase. Where the host cell is a tobacco cell, or tobacco cell line cell, the plant beta-N-acetylhexosaminidase is a tobacco beta-N-acetylhexosaminidase.

In further embodiments the plant beta-N-acetylhexosaminidase is inactivated plant beta-N-acetylhexosaminidase. Inactivation of plant beta-N-acetylhexosaminidase can be effected by physical means, chemical means or biochemical means. Physical inactivation can be performed by heating, freezing, desiccation, etc. Chemical inactivation can be performed by extremes of pH, chemical denaturation, addition or removal of side chains, glycans, amino acids, etc. Biochemical inactivation includes, but is not limited to inhibition by reversible or irreversible inhibitors. Exemplary beta-N-acetylhexosaminidase inhibitors include end-product inhibitors such as N-acetyl-D-glucosamine and beta-methyl-N-acetyl glucosamine, and selective inhibitors such as the compounds disclosed in US Patent Applications US2010016386, US20110237631, US20100087477 and US20120046337. It will be appreciated that preferred methods for inhibition and/or inactivation of the plant beta-N-acetylhexosaminidase are those which also effectively preserve the structural and functional integrity of the plant-expressed human DNase I enzyme.

In some embodiments the plant beta-N-acetylhexosaminidase is inactivated by heating the plant-expressed recombinant human DNase I composition. Suitable temperatures for plant beta-N-acetylhexosaminidase inhibition and/or activation include heating within a range of 37-60° C. for a period of 2 to 5, 10, 20, 30, 40, 50 60 or more minutes. It will be appreciated that effective inhibition and/or inactivation of the plant beta-N-acetylhexosaminidase is achieved more rapidly at higher temperatures and more slowly at lower temperatures of the range. In some embodiments, the plant-expressed recombinant human DNase I composition is heated in the range of 45-55° C. for 2-10 minutes. In some embodiments, the inhibition/inactivation results in 20, 30, 40, 50, 60, 70, 80% or greater inactivation of the plant beta-N-acetylhexosaminidase.

The present inventors have constructed a plant expression vector for recombinant expression of human DNase I in plant cells comprising a polynucleotide encoding a human DNase I polypeptide, transformed tobacco plants with the vector, and have isolated catalytically active human DNase I from the plants. The biochemical properties of the plant-expressed recombinant human DNase I compare favorably with those of the commercially available clinical standard Pulmozyme® (Dornase alpha), and results with CF sputum suggest an advantageous effect of the plant-expressed recombinant human DNase I on the reduction of rheological parameters of sputum, as well as reduced susceptibility to actin inhibition of the DNase endonuclease activity. Structural differences uncovered between the plant-expressed recombinant human DNase I and mammalian-cell expressed recombinant human DNase I (e.g. Pulmozyme®) (mobility on PAGE, unity of immunoreactive DNase I species as detected on Western blots, see hereinbelow) suggest that both modifications of amino acid sequence and post translational modification resulting from processing of the expressed polypeptide by the plant cell may be responsible for some of the distinguishing functional characteristics of the plant-expressed recombinant enzyme.

Thus, in some embodiments, there is provided an isolated polynucleotide comprising a nucleic acid sequence encoding a human DNase I protein, wherein the human DNase I protein is contiguously linked at the N-terminal to a plant endoplasmic reticulum targeting signal peptide.

According to another aspect of the invention, the human DNase I protein is contiguously linked at the N-terminal to an *Arabidopsis* ABPI endoplasmic reticulum targeting signal peptide.

As used herein the term "contiguously linked at the N-terminal" refers to covalent attachment of the indicated peptide via a peptide bond to the N-terminal amino acid of the mature protein, for example, human DNase I protein. "Contiguously linked at the C-terminal" refers to covalent attachment of the indicated peptide via a peptide bond to the C-terminal amino acid of the mature protein, for example, human DNase I protein.

As used herein, the term "*Arabidopsis* ABPI endoplasmic reticulum targeting signal peptide" refers to the leader peptide sequence of the *Arabidopsis thaliana* auxin binding protein, which is capable of directing the expressed protein to the endoplasmic reticulum within the plant cell. In one embodiment, the *Arabidopsis* ABPI endoplasmic reticulum targeting signal peptide is a 33 amino acid polypeptide as set forth in SEQ ID NO: 4.

Thus, according to another aspect of the present invention, the human DNase I protein contiguously linked at the N-terminal to an *Arabidopsis* ABPI endoplasmic reticulum targeting signal peptide and the human DNase I protein has an amino acid sequence as set forth in SEQ ID NO: 1.

According to some embodiments of the invention, the human DNase I protein is encoded by a nucleic acid sequence as set forth in SEQ ID NO: 9. According to further embodiments of the invention, the *Arabidopsis* ABPI endoplasmic reticulum targeting signal peptide is encoded by a nucleic acid sequence as set forth in SEQ ID NO: 10.

According to still further embodiments of the invention the human DNase I protein contiguously linked at the N-terminal to an *Arabidopsis* ABPI endoplasmic reticulum targeting signal peptide is encoded by a nucleic acid sequence as set forth in SEQ ID NO: 12.

In order to express the polypeptide, the sequence encoding same is ligated into a "plant nucleic acid expression construct".

As used herein the term "plant nucleic acid expression construct" refers to a nucleic acid construct which includes the nucleic acid of some embodiments of the invention and at least one promoter for directing transcription of nucleic acid in a host plant cell. Further details of suitable transformation approaches are provided hereinbelow.

According to some embodiments of the invention, there is provided a nucleic acid expression construct comprising the nucleic acid sequence of the invention, and a promoter for directing transcription of the nucleic acid sequence in a plant host cell.

As used herein the term "nucleic acid sequence" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the to above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the present invention, the nucleic acid sequences encoding the polypeptides of the present invention are optimized for expression in plants. Examples of such sequence modifications include, but are not limited to, an altered G/C content to more closely approach that typically found in the plant species of interest, and the removal of codons atypically found in the plant species commonly referred to as codon optimization. In one embodiment, the codon usage of the nucleic acid sequence encoding the human DNase I protein, the human DNase I protein contiguously linked at the N-terminal to an *Arabidopsis* ABPI endoplasmic reticulum targeting signal peptide, or any other human DNase I protein described herein is optimized for *Nicotiana tabacuum* or *Nicotiana benthamiana.*

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N[(Xn−Yn)/Yn]2/N, where Xn refers to the frequency of usage of codon n in highly expressed plant genes, where Yn to the frequency of usage of codon n in the gene of interest and N refers to the total number of codons in the gene of interest.

A table of codon usage from highly expressed genes of dicotyledonous plants has been compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage table having been statistically determined based on the data present in Genbank.

By using such codon optimization tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The desired encoding nucleotide sequence may already, in advance of any modification, contain a number of codons that correspond to a statistically-favored codon in a particular plant species. Therefore, codon optimization of the native nucleotide sequence may comprise determining which codons, within the desired nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

According to some embodiments of the invention, the nucleic acid is operably linked to the promoter sequence.

A coding nucleic acid sequence is "operably linked" to a regulatory sequence (e.g., promoter) if the regulatory sequence is capable of exerting a regulatory effect on (e.g. effect on the expression of) the coding sequence linked thereto.

Any suitable promoter sequence can be used by the nucleic acid construct of the present invention. Preferably the promoter is a constitutive promoter, a tissue-specific, or an inducible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Such a promoter can be constitutive, i.e., capable of directing high level of gene expression in a plurality of tissues, tissue specific, i.e., capable of directing gene expression in a particular tissue or tissues, inducible, i.e., capable of directing gene expression under a stimulus, or chimeric, i.e., formed of portions of at least two different promoters.

Examples of preferred promoters useful for the methods of some embodiments of the invention are presented in Table I, II, III and IV.

TABLE I

Exemplary constitutive promoters for use in the performance of some embodiments of the invention

| Gene Source | Expression Pattern | Reference |
|---|---|---|
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An et al, Plant J. 10(1); 107-121, 1996 |

TABLE II

Exemplary seed-preferred promoters for use in the performance of some embodiments of the invention

| Gene Source | Expression Pattern | Reference |
|---|---|---|
| Seed specific genes | seed | Simon, et al., Plant Mol. Biol. 5. 191, 1985; Scofield, et al., J. Biol. Chem. 262: 12202, 1987.; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al. Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al Plant Mol Biol, 143). 323-32 1990 |
| napA | seed | Stalberg, et al, Planta 199: 515-519 1996 |
| wheat LMW and HMW, glutenin-1 | endosperm | Mol Gen Genet 216: 81-90, 1989; NAR 17: 461-2, |
| Wheat SPA | seed | Albanietal, Plant Cell, 9: 171-184 1997 |
| wheat a, b and g gliadins | endosperm | EMBO3: 1409-15, 1984 |
| Barley ltrl promoter | endosperm | |
| barley B1, C, D hordein | endosperm | Theor Appl Gen 98: 1253-62, 1999; Plant J 4: 343-55, 1993; Mol Gen Genet 250: 750-60, 1996 |
| Barley DOF | endosperm | Mena et al, The Plant Journal, 116(1): 53-62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice-globulin Glb-1 | endosperm | Wu et al, Plant Cell Physiology 398) 885-889, 1998 |

TABLE II-continued

| Exemplary seed-preferred promoters for use in the performance of some embodiments of the invention | | |
|---|---|---|
| Gene Source | Expression Pattern | Reference |
| rice OSH1 | embryo | Sato et al, Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| *sorghum* gamma-kafirin | endosperm | PMB 32: 1029-35, 1996 |
| KNOX | emryo | Postma-Haarsma et al, Plant Mol. Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, et al., Plant Mol. Biol. 19: 873-876, 1992 |

TABLE III

| Exemplary flower-specific promoters for use in the performance of the invention | | |
|---|---|---|
| Gene Source | Expression Pattern | Reference |
| AtPRP4 | flowers | www.dotsalus.dotmedium.dotedu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala-3 | flowers | |

TABLE IV

| Alternative rice promoters for use in the performance of the invention | | |
|---|---|---|
| PRO # | gene | expression |
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl-CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 strong root | |
| PR00111 | uclacyanin 3-like protein | weak discrimination center/shoot meristem |
| PR00116 | 26S proteasome regulatory particle non-ATPase subunit 11 | very weak meristem specific |

TABLE IV-continued

| Alternative rice promoters for use in the performance of the invention | | |
|---|---|---|
| PRO # | gene | expression |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha-globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSH1 | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PR00228 | BLZ-2_long (barley) | |

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the nucleic acid is integrated into the plant genome and as such it represents a stable and inherited trait. In transient transformation, the exogenous polynucleotide is expressed by the cell transformed but it is not integrated into the genome and as such it represents a transient trait.

Thus, according to some aspects of the present invention, there is provided an isolated cell comprising the nucleic acid construct of the invention.

As used herein, the term "isolated cell" refers to a cell at least partially separated from the natural environment e.g., from a plant. In some embodiments, the isolated cell is a plant cell of a whole plant. In some embodiments, the isolated cell is a plant cell, for example, a plant cell in culture.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalypfus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratis sima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barely, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant or plant cell is a duckweed plant, cell or nodule. Duckweed (members of the monocotyledonous family Lemnaceae, or Lemna) plant or duckweed nodule cultures can be efficiently transformed with an expression cassette containing a nucleotide sequence of interest by any one of a number of methods including *Agrobacterium*-mediated gene transfer, ballistic bombardment, or electroporation. Methods for molecular engineering of duckweed cells and detailed description of duckweed expression systems and useful for commercial production of valuable polypeptides are known in the art (see, for example, U.S. Pat. Nos. 6,040,498 and 6,815,184 to Stomp, et al, and U.S. Pat. No. 8,022,270 to Dickey et al).

According to some embodiments of the invention, the plant or plant cell used by the method of the invention is a crop plant or cell of a crop plant such as rice, maize, wheat, barley, peanut, potato, sesame, olive tree, palm oil, banana, soybean, sunflower, canola, sugarcane, alfalfa, millet, leguminosae (bean, pea), flax, lupinus, rapeseed, tobacco, poplar and cotton.

According to further embodiments the plant cells includes tobacco cells, *Agrobacterium rihzogenes* transformed root cell, celery cell, ginger cell, horseradish cell and carrot cells. In one embodiment the tobacco cells are from a tobacco cell line, such as, but not limited to *Nicotiana tabacum* L. cv Bright Yellow (BY-2) cells. The plant cells may be grown according to any type of suitable culturing method, including but not limited to, culture on a solid surface (such as a plastic culturing vessel or plate for example) or in suspension. It will be noted that some cells, such as the BY-2 and to carrot cells can be cultured and grown in suspension. Suitable devices and methods for culturing plant cells in suspension are known in the art, for example, as described in International Patent Application PCT IL2008/000614. In yet another embodiment the cells are cells of whole tobacco plants or plant tissues, including, but not limited to *Nicotiana benthamiana.*

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain to defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Galon et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol. 81)", Humana Press, 1998; Maramorosh and Koprowski, eds. "Methods in Virology" 7 vols., Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the nucleic acid sequence includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

According to some embodiments of the invention, the method further comprises growing the plant cell expressing the nucleic acid. The plant cells can be any plant cells desired. The plant cells can be cultured cells, cells in cultured tissue or cultured organs, or cells in a plant. In some embodiments, the plant cells are cultured cells, or cells in cultured tissue or cultured organs. In yet further embodiments, the plant cells are any type of plant that is used in gene transference. The plant cell can be grown as part of a whole plant, or, alternatively, in plant cell culture.

According to some aspects of the invention, the plant cells are grown in a plant cell suspension culture. As used herein, the term "suspension culture" refers to the growth of cells separate from the organism. Suspension culture can be facilitated via use of a liquid medium (a "suspension medium"). Suspension culture can refer to the growth of cells in liquid nutrient media. Methods and devices suitable for growing plant cells of the invention in plant cell suspension culture are described in detail in, for example, PCT WO2008/135991, U.S. Pat. No. 6,391,683, U.S. patent application Ser. No. 10/784,295; International Patent Publications PCT Nos. WO2004/091475, WO2005/080544 and WO 2006/040761, all of which are hereby incorporated by reference as if fully set forth herein.

Thus, the invention encompasses plants or plant cultures expressing the nucleic acid sequences, so as to produce the recombinant human DNase I protein of the invention. Once expressed within the plant cell or the entire plant, the level of the human DNase I protein encoded by the nucleic acid sequence can be determined by methods well known in the art such as, activity assays, Western blots using antibodies capable of specifically binding the human DNase I protein, Enzyme-Linked Immuno Sorbent Assay (ELISA), radioimmuno-assays (RIA), immunohistochemistry, immunocytochemistry, immunofluorescence and the like.

Methods of determining the level in the plant of the RNA transcribed from the nucleic acid sequence are well known in the art and include, for example, Northern blot analysis, reverse transcription polymerase chain reaction (RT-PCR) analysis (including quantitative, semi-quantitative or real-time RT-PCR) and RNA-in situ hybridization.

According to some embodiments of the invention, the expressed recombinant human DNase I protein is glycosylated in the plant cell, resulting in a recombinant human DNase I protein having high mannose glycosylation (e.g. exposed mannose sugar residues), and plant specific glycan residues. Thus, according to some embodiments of the invention, the cells expressing the expression vector of the invention produce a to human DNase I protein having at least one, optionally at least two, optionally at least three or optionally at least four or more exposed mannose residues. In other embodiments the cells expressing the expression vector of the invention produce a human DNase I protein having at least one, optionally at least two, optionally at least three or optionally at least four or more core xylose residues. In yet other embodiments the cells expressing the expression vector of the invention produce a human DNase I protein having at least one, optionally at least two, optionally at least three or optionally at least four or more core α-(1,3) fucose residues. In one embodiment the cells expressing the expression vector of the invention produce a human DNase I protein having at least one exposed mannose residue, at least one core xylose residue and at least one α-(1,3) fucose residue. In yet further embodiments, the cells expressing the expression vector of the invention produce a human DNase I protein having at least one, at least two, at least 3 or more terminal N-acetyl glucosamine substitutions on the outer mannose sugars.

Glycan analysis of human DNase I protein expressed in plant cells indicated that the prh DNase I lacks sialic acid residues. Thus, in yet other embodiments, the cells expressing the expression vector of the invention produce a recombinant human DNase I protein devoid of sialic acid residues.

The human DNase I protein produced by cells expressing the expression vector of the invention was shown to have DNase I catalytic activity similar or superior to that of a native human or mammalian-cell produced DNase I enzyme.

As shown in Example 3 herein, when enzyme kinetics of the plant-expressed recombinant human DNase I protein were measured (see Table VI), greater substrate affinity ($K_M$) and higher reaction velocity ($V_{max}$) were observed for the plant-expressed recombinant human DNase I protein, as compared to those of mammalian cell-expressed recombinant human DNase I (e.g. Pulmozyme®). Thus, according to some embodiments the plant expressed recombinant human DNase I is biologically active. In some embodiments, the biological activity is endonuclease catalytic activity. In yet other embodiments, the biological activity of the plant-expressed recombinant human DNase I protein is characterized by greater substrate affinity ($K_M$) and higher reaction velocity ($V_{max}$), as compared to those of mammalian cell-expressed recombinant human DNase I (e.g. Pulmozyme®). Methods for measuring biological activity of DNase I are well to known in the art, and include, inter alia, catalytic activity (e.g. methyl green assay, DNaseAlert™-based assay, fluorescence-based assay, as described herewith), immuno-reactivity with anti-DNase I antibody, Kunitz-based hyperchromicity assay, assays measuring proton release upon DNA hydrolysis, which can be monitored by using chromophoric H+ ion indicators, and the like. In still other embodiments, the biological activity of the plant-expressed recombinant human DNase I protein is characterized by specific activity (units DNase I catalytic activity per mg enzyme protein) greater than that of mammalian cell-expressed recombinant human DNase I (e.g. Pulmozyme®). In some embodiments, the specific activity of plant-expressed recombinant human DNase I protein is about 1.1, about 1.2, about 1.25, about 1.5, about 1.75, about 2.0, about 2.25, about 2.5, about 2.75, about 3.0, about 3.25, about 3.5, about 3.75, about 4.0, about 4.5 to 5.0 or more fold that of the specific activity (e.g. U/mg) of mammalian cell-expressed recombinant human DNase I (e.g. Pulmozyme®). In some embodiments, the specific activity of plant-expressed recombinant human DNase I protein is about 3.0 to 3.5 fold that of the specific activity (e.g. U/mg) of mammalian cell-expressed recombinant human DNase I (e.g. Pulmozyme®).

As shown in Example 4 herein, when enzyme activity of DNase I protein was measured (see Table VIII) in the presence of increasing concentrations of actin, greater resistance of the plant-expressed recombinant human DNase I to inhibition of catalytic activity by actin was observed, compared to that of mammalian cell-expressed recombinant human DNase I (e.g. Pulmozyme®). Thus, according to some embodiments the plant expressed recombinant human DNase I has greater resistance to actin inhibition of DNase I catalytic activity when compared to that of mammalian cell-expressed recombinant human DNase I (e.g. Pulmozyme®). In some embodiments, the inhibition of DNase I catalytic activity is expressed as half-maximal inhibitory concentration of actin ($IC_{50}$, μg actin/ml), using, for example, the methyl green DNase I assay. Thus, in some embodiments, the $IC_{50}$ actin concentration for inhibition of the plant expressed recombinant human DNase I is at least 1.25, about 1.5, about 1.75, about 2.0, about 2.25, about 2.5, about 2.75, about 3.0, about 3.25, about 3.5, about 3.75, about 4.0, about 4.5 to 5.0 or more, or a range of about 1.5 to 2.5 that of mammalian cell-expressed recombinant human DNase I (e.g. Pulmozyme®). In some embodiments, the $IC_{50}$ actin concentration for inhibition of the plant expressed recombinant human DNase I activity is about 2.0 to 2.2 fold that of mammalian cell-expressed recombinant human DNase I (e.g. Pulmozyme®).

As shown in Example 5, plant expressed recombinant human DNase I effectively reduces the rheological properties of sputum. When measured in an in-vitro assay, incubation of the plant expressed recombinant human DNase I with samples of CF sputum results in reduction of the viscous modulus (as expressed by the loss modulus, G") and reduction of the elasticity (as expressed by the storage modulus, G') of the sputum sample (see FIGS. 12A-12D, 13A-13D, 14A-14B, 16 and 17). When compared to the reduction of rheological parameters of sputum samples incubated with mammalian cell-expressed recombinant human DNase I (e.g. Pulmozyme®), the plant expressed recombinant human DNase I displayed greater efficacy in reducing viscosity and elasticity than that of mammalian cell-expressed recombinant human DNase I (e.g. Pulmozyme®) (FIGS. 12 and 13). Thus, according to some embodiments of the invention, the plant expressed recombinant human DNase I reduces viscous modulus and/or elastic modulus of sputum. In other embodiments, reduction in viscous and elastic modulus is expressed as G" and G', respectively. In yet another embodiment, reduction of viscous and/or elastic modulus of sputum by the plant expressed recombinant human DNase I is greater than that of mammalian cell-expressed recombinant human DNase I (e.g. Pulmozyme®) measured with the same assay technique. Thus, in some embodiments, the plant expressed human recombinant DNase I of the invention is biologically active, having catalytic activity, enzyme kinetics and specific activity comparable or superior to that of mammalian cell-expressed recombinant human DNase I, and effective in reducing rheological properties of CF sputum. In other embodiments, the rheological properties of sputum are assayed using stress sweep measurements, and can be characterized by the cross-over points of elastic and viscous stress values.

Thus, the human DNase I protein expressed in plant cells according to the invention can be used to produce an inhalable pharmaceutical composition for treatment or prevention of any condition or disease by pulmonary administration. According to some aspects of the invention, the pharmaceutical composition can be used for treatment or prevention of mucus-associated conditions in a subject in need thereof. In some embodiments, the mucus associated conditions comprise respiratory or pulmonary disease or conditions.

In some embodiments of the invention, the pharmaceutical composition comprising DNase I can be administered for reducing extracellular DNA in a secretion, fluid or tissue of a subject in need thereof. Secretions, tissues and fluids accessible to the pharmaceutical composition formulations of the invention include pulmonary secretions, fluids and tissues such as mucus and other extracellular bronchopulmonary fluids, and secretions, fluids and tissues accessible via the circulatory system, such as blood, intestinal mucosal secretions and the like.

Thus, according to some embodiments of the invention, there is provided a method for preventing or treating a pulmonary disease or condition associated with excess DNA in a pulmonary secretion in a subject in need thereof, the method comprising administering, via pulmonary administration, an effective amount of the inhalable pharmaceutical composition of the invention. Suitable formulations and dosage regimens are provided herewith in detail.

Respiratory conditions or diseases which can be treated by administration of the pharmaceutical composition of the invention include conditions associated with accumulation of mucus or other DNA containing secretions or fluids, for example, in the airways. Such conditions include, but are not limited to acute or chronic bronchopulmonary disease, atelectasis due to tracheal or bronchial impaction and complications of tracheostomy chronic bronchitis, asthmatic bronchitis, cystic fibrosis, pneumonia, allergic diseases such as allergic asthma, non-allergic asthma, systemic lupus erythematosus, Sjogren's syndrome, bronchiectasis, emphysema, acute and chronic sinusitis, and even the common cold.

Non-respiratory conditions that can be treated by the of the pharmaceutical composition invention include, but are not limited to, male infertility, metastatic cancer, viral, bacterial, fungal and protozoan infections and sepsis, atherosclerosis, diabetes, delayed type hypersensitivity and uterine disorders.

In further embodiments, biological activity of the pharmaceutical composition comprising human DNase I of the invention is enhanced by the presence of an additional pharmacological agent, for example, an agent which reduces actin inhibition of DNase activity, such as one or more inorganic salt selected from potassium, magnesium, calcium, zinc, lithium, manganese, cadmium, nickel, cobalt, ammonium, polyamine and macrocyclic polyammonium salts. Agents suitable for combination with the plant expressed human recombinant DNase I of the invention, for therapeutic applications such as treatment of pulmonary conditions (e.g. CF) are described in detail in U.S. Pat. No. 7,432,308 to Demeester et al., which is incorporated herein by reference in its entirety.

In some embodiments, combination of the pharmaceutical composition comprising human DNase I, for example, prh DNase I, with an additional pharmaceutical agent results in improvement, and optionally synergic improvement in reduction of rheological properties (e.g. viscous modulus and/or elastic modulus) of sputum. In some embodiments, the additional agent is magnesium chloride or magnesium sulfate.

In some embodiments of the invention, the pharmaceutical composition comprising DNase I is combined with, or administered along with an additional pharmaceutical agent, the additional pharmaceutical agent including, but not limited to one or more other pharmacologic agents used to treat the conditions listed above, such as antibiotics, bronchodilators, anti-inflammatory agents, mucolytics (e.g. n-acetylcysteine), actin binding or actin severing proteins [e.g., gelsolin; Matsudaira et al., Cell 54:139-140 (1988); Stossel, et al., PCT Patent Publication No. WO 94/22465], protease inhibitors, or gene therapy product [e.g., comprising the cystic fibrosis transmembrane conductance regulator (CFTR) gene, Riordan, et al., Science 245:1066-1073 (1989)].

Additional pharmaceutical agents can be administered prior to, along with, subsequent to or in any other temporal combination with the formulation of the invention. Regimen for combination of the formulation of the invention with additional agents can be formulated according to parameters such as specific conditions or diseases, health status of the subject, methods and dose of administration, and the like.

Determination of such combination regimen can be done, for example, by professionals such as attending physicians, hospital staff, and also according to predetermined protocols.

Herein the term "active ingredient" refers to the recombinant human DNase I protein accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient.

Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

As used herein, the term "subject in need thereof" refers to a subject diagnosed with or exhibiting one or more conditions associated with a disease or condition treatable by administration of DNase I, a subject who has been diagnosed with or exhibited one or more conditions treatable by administration of DNase I in the past, or a subject who has been deemed at risk of developing one or more conditions associated with a disease or condition treatable by administration of DNase I in the future due to hereditary or environmental factors. In certain embodiments of the invention, the subject in need thereof is suffering from a disease or condition such as, but not limited to respiratory and/or pulmonary disease or condition, male infertility, viral infection, a uterine disorder, an endometrial disorder or condition, cancer, primary cancer and/or metastatic cancer.

In some embodiments, a subject in need thereof refers to a subject with a pulmonary condition having clinically abnormal spirometry values. Examples of spirometry parameters which can indicate the need of a subject include, but are not restricted to forced expiration volume$_1$ ($FEV_1$), forced vital capacity (FVC), forced expiratory flow (FEF25-75) and the like. In some embodiments of the invention administration of the prhDNase to the subject results in an improvement in one or more of the spirometric parameters.

Pulmonary administration of DNase

Pulmonary administration may be accomplished by suitable means known to to those in the art. Pulmonary administration of DNase requires dispensing of the biologically active substance from a delivery device into the oral cavity of a subject during inhalation. For purposes of the present invention, compositions comprising DNase are administered via inhalation of the pharmaceutical composition of the invention, via a liquid mist or aerosol inhaler delivery device. Such delivery devices are well known in the art and include, but are not limited to, metered dose and premetered aerosol inhalers, nebulizers or any other appropriate delivery mechanisms that allow for dispensing of a liquid form of the pharmaceutical composition.

Metered Dose Inhaler (MDI) Device

In one embodiment, the DNase, including an enzymatically active portion thereof, is delivered to a subject through metered dose inhaler (MDI) device. An MDI device uses a propellant to deliver reproducible metered drug dose to the lung and/or airways, and comprises a drug or agent, propellants (e.g. hydrofluoroalkanes (HFA)), surfactants (e.g. phosphatidyl choline, phosphatidyl ethanolamine, phosphatidyl inositol, lysophosphatidyl choline, phosphatidic acid, triglycerides, monogycerides, soy lecithin, fatty acids, and alkyl-polyglycosides), and solvents. An MDI device is often a compact pressurized dispenser, including a canister, metering valve, and spacer. The dose administered by an MDI device is generally in mg and ranges in volume from about 25 to 100 mL. Additionally, MDI devices are advantageous as they are tamper-proof.

Examples of CFC-free MDI products include Albuterol® HFA (Ivax), Atrovent®-HFA (Boehringer-Ingelheim), Proventil®-HFA (3M), Flovent®-HFA (GSK), Qvar® (3M), Ventolin® HFA(GSK), Xopenex® HFA (3M/Sepracor), Salamol Easi-Breathe® CFC-Free (Ivax), Berotec® (Boehringer-Ingelheim), Berodual® (Boehringer-Ingelheim), Intal® Forte (Rhone/Aventis), and Seretide® EvoHaler® (GSK).

Examples of MDI devices include, but are not limited to, the following:

In one embodiment, the invention provides an MDI device for pulmonary administration of DNase to a subject, wherein the MDI device is an AutoHaler® (3M) (see U.S. Pat. No. 6,120,752). Examples of AutoHaler® devices being used to deliver therapeutic agents include Aerobid® (flunisolide), Alupent® (metaproterenol sulphate), Atrovent®/Atovent®-HFA (ipratropium bromide), Combivent® (albuterol to sulfate/ipatropium bromide), MaxAir® AutoHaler® (pirbuterol acetate), Proventil@-HFA (albuterol sulphate), Qvar® (beclomethasone dipropionate) and Xopenex® HFA (levalbuterol hydrochloride).

Another MDI device which may be used in the methods and compositions of the invention includes the breath-activated MD Turbo™ (Accentia Bio), which transforms metered-dose inhalers into a breath-activated, dose-counting inhaler.

In one embodiment, the invention provides an MDI device for pulmonary administration of DNase to a subject, wherein the MDI device is the continuous inhalation flow device WatchHaler® (Activaero GmbH).

The portable drug delivery system EZ Spacer® (AirPharma) may also be used in the methods and compositions of the invention. In another embodiment, the Asmair®(Bang and Olufsen Medicom AS) MDI. In yet another embodiment, the invention includes an Active DPI/MPI device (Bespak) (see WO9419042). In still another embodiment, the invention provides an MDI device for pulmonary administration of DNase to a subject, wherein the MDI device is a device for delivering metered aerosols comprising an active ingredient in solution in a propellant consisting of a hydrofluoroalkane (HFA) (see WO0149350; Chiesi).

Other examples of MDI devices which may be used in the invention include MDI inhalers described in U.S. Pat. No. 6,170,717 (GlaxoSmithKline); EasiBreath® MDI (Ivax; WO193933, U.S. Pat. No. 5,447,150); MDI breath coordinated inhaler and breath actuated inhaler (Kos; CA2298448 and WO2004082633); Tempo™ (MAP Pharma; U.S. Pat. Nos. 6,095,141, 6,026,808 and 6,367,471); Xcelovent™ (Meridica/Pfizer; WO9852634; a breath operated device that also has a dose counter feature); and Increased dosage MDI (Nektar see WO2004041340; a device capable of delivering 2 mg to 5 mg of a formulated drug using HFA propellants) and a MDI described in WO03053501 (Vectura).

Thus, the invention also includes a metered dose inhaler (MDI) device for pulmonary administration of DNase to a subject, the MDI device comprising a pressurized canister comprising an aerosol comprising the DNase and a propellant, and a means for introducing the aerosol into the subject via inhalation.

Nebulizer/Liquid Inhaler

In one embodiment, the DNase, including an enzymatically active portion thereof, is delivered to a subject using a nebulizer or liquid inhaler. Generally, nebulizers use compressed air to deliver medicine as wet aerosol or mist for inhalation, and, therefore, require that the drug be soluble in water. Nebulizer devices can deliver relatively large doses in comparison to MDI or DPI devices, and are especially effective for delivery to the deep lung (peripheral lung region). No propellants are required for nebulizers, which includes jet nebulizers (air-jet nebulizers and liquid-jet nebulizers) and ultrasonic nebulizers. Examples of nebulizers include Akita™ (Activaero GmbH) (see U.S. Pat. No. 7,766,012, EP1258264), a table top nebulizer inhalation system based on Pari's LC Star that provides full control over patient's breathing pattern and the portable Aeroneb® Go/Pro/Lab nebulizers (AeroGen). The Aeroneb® nebulizer is based on OnQ™ technology, i.e., an electronic micropump surrounded by a vibrational element and adaptable to the needs of a broad range of patients, including children and the elderly; single or multi-patient use.

The portable Aerocurrent™ (AerovertRx corp) may also be used in the methods and compositions of the invention (see WO2006006963).

Staccato™ (Alexza Pharma) may also be used in the methods and compositions of the invention (see WO03095012). The key to Staccato™ technology is vaporization of a drug without thermal degradation. AERx® (Aradigm), a hand held battery operated device, may also be used in the methods and compositions of the invention (see WO9848873, U.S. Pat. Nos. 5,469,750, 5,509,404, 5,522, 385, 5,694,919, 5,735,263, 5,855,564). Another example of a nebulizer device which may also be used in the methods and compositions of the invention includes Respimat® (Boehringer), a multidose reservoir system. The DNase may also be delivered using the Collegium Nebulizer™ (Collegium Pharma).

Another example of a nebulizer device which may also be used in the methods and compositions of the invention includes the Inspiration® 626 (Respironics), a compressor based nebulizer for home care delivering a particle size between 0.5 to 5 microns, Adaptive Aerosol Delivery® technology (Respironics), which delivers precise and reproducible inhaled drug doses.

Adaptive Aerosol Delivery (AAD)® systems incorporate electronics and sensors within the handpiece to monitor the patient's breathing pattern by detecting pressure changes during inspiration and expiration, allowing the patient to take breaks in therapy without medication waste. Examples of AAD® system nebulizers include the HaloLite® AAD®, ProDose® AAD®, and I-Neb® AAD®. The HaloLite® Adaptive Aerosol Delivery (AAD)® (Respironics) is a pneumatic aerosolization system powered by a portable compressor (see EP 0910421, incorporated by reference herein).

The ProDos AAD® (Respironics) is a pneumatic aerosol system powered by a portable compressor, controlled by "ProDose Disc™" system. (Respironics). (see EP1245244). Promixin® can be delivered via Prodose AAD® for management of *pseudomonas aeruginosa* lung infections, particularly in cystic fibrosis. Promixin® is supplied as a powder for nebulization that is reconstituted prior to use. The I-neb AAD® is a handheld, miniaturized AAD® system without the need for a separate compressor ("I-Neb"), based upon a combination of electronic mesh-based aerosolization technology (Omron) and AAD® technology. I-neb AAD® has been used for delivery of Ventavis® (iloprost) (CoTherix/Schering AG).

Another example of a nebulizer which may be used in the methods and compositions of the invention is Aria™ (Chrysalis). Aria is based on a capillary aerosol generation system with MMAD ranging from 0.5-2.0 urn.

In another embodiment, the TouchSpray™ nebulizer (Odem), which uses a perforate membrane, which vibrates at ultrasonic frequencies, in contact with the reservoir fluid, to generate the aerosol cloud (see U.S. Pat. No. 6,659,364) may be used to deliver DNase in accordance with the invention. Additional nebulizers which may be used in the invention include nebulizers which are portable units which maximize aerosol output when the patient inhales and minimize aerosol output when the patient exhales using two one-way valves (see PARI nebulizers (PARI GmbH), which may be designed for specific patient populations, such a patients less than three years of age (PARI BABY™) and nebulizers for older patients (PARI LC PLUS® and PARI LC STAR®).

An additional nebulizer which may be used in the invention is the e-Flow® nebulizer (PARI GmbH) which uses vibrating membrane technology to aerosolize the drug solution, as well as the suspensions or colloidal dispersions (TouchSpray™; ODEM (United Kingdom)), as described in U.S. Pat. No. 6,962,151. Additional nebulizers which may be used in the invention include the Hudson T-Updraft I or II nebulizer (Pulmo-Aide compressor), Marquest Acorn I or II nebulizer (Pulmo-Aide compressor), Durable Sidestream (Portaneb compressor), Microair® electronic nebulizer (Omron)(see U.S. Pat. No. 6,901,926) and a Mystic™ nebulizer (Ventaira)(see U.S. Pat. No. 6,397,838). The Mystic™ device is breath activated, and has been used with Corus 1030™ (lidocaine HCl), Resmycin® (doxorubicin hydrochloride), Acuair (fluticasone propionate), NCE with ViroPharm, and NCE with Pfizer. Thus, in one embodiment, the invention provides a container for use with a nebulizer device for pulmonary administration of DNase to a subject, the container comprising a propellant-free inhalable solution or suspension comprising the DNase.

Formulations

DNase for use in the methods of the invention is formulated in pharmaceutical composition suitable for inhalation. Suitable preparations include all liquid inhalable pharmaceutical preparations so long as the particles comprising the protein composition are delivered in a size range consistent with that described for the pulmonary delivery device, e.g., a pharmaceutical composition form of the formulation.

DNase for use in the methods of the invention, can be incorporated into pharmaceutical compositions suitable for pulmonary administration to a subject. The compositions for use in the methods and compositions of the invention may be in a variety of forms according to the mode of inhalation and therapeutic application. In one embodiment, the invention provides a pharmaceutical composition comprising a DNase and a pharmaceutically acceptable carrier, wherein the pharmaceutical composition is suitable for inhalation by a subject. Thus, the DNase is formulated in a liquid pharmaceutical composition suitable for inhalation. Examples of pharmaceutical compositions which are suitable for inhalation include, but are not limited to a propellant-containing aerosol, and a propellant-free inhalable solution or suspension.

Such pharmaceutical compositions may be administered according to the devices described above. For example, a propellant-free inhalable solution comprising the DNase may be administered to the subject via a nebulizer. Other suitable preparations include, but are not limited to, mist, vapor, or spray preparations so long as the particles comprising the protein composition are delivered in a size range consistent with that described for the delivery device, e.g., a pharmaceutical composition form of the pharmaceutical composition.

Where a liquid solution or suspension is used in the delivery device, a nebulizer, a metered dose inhaler, or other suitable delivery device delivers, in a single or multiple fractional dose, by pulmonary inhalation a pharmaceutically effective amount of the composition to the subject's lungs as droplets having the same particle size range noted above for the pharmaceutical composition form. Methods for preparing and using formulations suitable for use as liquid or suspension are known in the art, for example, the oil-based matrix taught in PCT WO 2011/004476.

Where the liquid pharmaceutical composition is lyophilized prior to use in the delivery methods of the invention, the lyophilized composition may be milled to obtain the finely divided dry powder consisting of particles within the desired size range noted above. Where spray-drying is used to obtain a dry powder form of the liquid pharmaceutical composition, the process is carried out under conditions that result in a substantially amorphous finely divided dry powder consisting of particles within the desired size range noted above. Similarly, if the starting pharmaceutical composition is already in a lyophilized form, the composition can be milled to obtain the dry powder form for subsequent preparation as a liquid aerosol or other liquid preparation suitable for pulmonary inhalation.

The amount of the composition placed within a delivery device is sufficient to allow for delivery of a pharmaceutically effective amount of the composition to the subject by inhalation. Following placement of the composition within a delivery device, the properly sized particles as noted above are suspended in an aerosol propellant. The pressurized nonaqueous suspension is then released from the delivery device into the air passage of the subject while inhaling. The delivery device delivers, in a single or multiple fractional dose, by pulmonary inhalation a pharmaceutically effective amount of the composition to the subject's lungs. The aerosol propellant may be any conventional material employed for this purpose, such as a chlorofluorocarbon, a hydrochloro-fluorocarbon, a hydrofluorocarbon, or a hydrocarbon, including trichlorofluoromethane, dichlorodifluoromethane, dichlorotetrafluoromethane, dichlorodifluoromethane, dichlorotetrafluoroethanol, and 1,1,1,2-tetrafluoroethane, or combinations thereof. A surfactant may be added to the formulation to reduce adhesion of the protein-containing liquid composition to the walls of the delivery device from which the aerosol is dispensed. Suitable surfactants for this intended use include, but are not limited to, sorbitan trioleate, soya lecithin, and oleic acid.

The pharmaceutical compositions may include a stabilizing agent include any sugar or sugar alcohol or any amino acid. Preferred sugars include sucrose, trehalose, raffinose, stachyose, sorbitol, glucose, lactose, dextrose or any combination thereof, preferably sucrose. When the stabilizing agent is a sugar, it is present in the range of about 0% to about 9.0% (w/v), preferably about 0.5% to about 5.0%, more preferably about 1.0% to about 3.0%, most preferably about 1.0%. When the stabilizing agent is an amino acid, it is present in the range of about 0% to about 1.0% (w/v), preferably about 0.3% to about 0.7%, most preferably about 0.5%. Stabilized lyophilized or spray-dried compositions for preparation of the liquid pharmaceutical composition of the invention may optionally comprise methionine, ethylenediaminetetracetic acid (EDTA) or one of its salts such as disodium EDTA or other chelating agent, which protect DNase against methionine oxidation. Methionine is present in the stabilized lyophilized or spray-dried formulations at a concentration of about 0 to about 10.0 mM, preferably about 1.0 to about 9.0 mM, more preferably about 2.0 to about 8.0 mM, even more preferably about 3.0 to about 7.0 mM, still more preferably about 4.0 to about 6.0 mM, most preferably about 5.0 mM. EDTA is present at a concentration of about 0 to about 10.0 mM, preferably about 0.2 mM to about 8.0 mM, more preferably about 0.5 mM to about 6.0 mM, even more preferably about 0.7 mM to about 4.0 mM, still more preferably about 0.8 mM to about 3.0 mM, even more preferably about 0.9 mM to about 2.0 mM, most preferably about 1.0 mM.

The composition of the invention can be formulated with addition ingredients.

These can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring. When the dosage unit form is a capsule, it contains, in addition to material of the above type, a liquid carrier.

Stabilized lyophilized or spray-dried compositions may be formulated using a to buffering agent, which maintains the pH of the formulation within an acceptable range when in a liquid phase, such as during the formulation process or following reconstitution of the dried form of the composition. In some embodiments the pH is in the range of about pH 4.0 to about pH 8.5, about pH 4.5 to about pH 7.5, about pH 5.0 to about pH 6.5, about pH 5.6 to about pH 6.3, and about pH 5.7 to about pH 6.2.

Suitable pH's include about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.7, about 7.8, about 7.9, about 8.0, about 8.2, about 8.4, about 8.6, about 8.8, about 9.0. In one particular embodiment, the pH is about 7.0 to 8.2. Suitable buffering agents include, but are not limited to, citrate buffer, phosphate buffer, succinate buffer, more particularly a sodium citrate/citric acid. Alternatively imidazole or histidine or other base/acid that maintains pH in the range of about pH 4.0 to about 8.5 can be used. Buffers are chosen such that they are compatible with the drying process and do not affect the quality, purity, potency, and stability of the protein during processing and upon storage.

Any of the formulations comprising human DNase I contemplated for use in the methods of the invention may be formulated with at least one surfactant. For pulmonary intracellular administration of the DNase, the surfactant can be in an amount sufficient to enhance absorption of the inhaled particles or mist comprising DNase to obtain an absorbable composition for use in pulmonary inhalation in accordance with the methods described herein. Any surfactant that enhances absorption of a formulation comprising DNase thereof in the manner disclosed herein may be used to obtain these absorbable protein-containing formulations. Surfactants suitable for use in enhancing absorption of the inhaled DNase include, but are not limited to, polyoxyethylene sorbitol esters such as polysorbate 80 (Tween 80) and polysorbate 20 (Tween 20); polyoxypropylene-polyoxyethylene esters such as Poloxamer 188; polyoxyethylene alcohols such as Brij 35; a mixture of polysorbate surfactants with phospholipids such as phosphatidylcholine and derivatives (dipalmitoyl, dioleoyl, dimyristyl, or mixed derivatives such as 1-palmitoyl, 2-olcoyl, etc.), dimyristolglycerol and other members of the phospholipid glycerol series; lysophosphatidylcholine and derivatives thereof; mixtures of polysorbates with lysolecithin or cholesterol; a mixture of polysorbate surfactants with to sorbitan surfactants (such as sorbitan monoleate, dioleate, trioleate or others from this class); poloxamer surfactants; bile salts and their derivatives such as sodium cholate, sodium deoxycholate, sodium glycodeoxycholate, sodium taurocholate, etc.; mixed micelles of DNase with bile salts and phospholipids; Brij surfactants (such as Brij 35-PEG923) lauryl alcohol, etc.). The amount of surfactant to be added is in the range of about 0.005% to about 1.0% (w/v), preferably about 0.005% to about 0.5%, more preferably about 0.01% to about 0.4%, even more preferably about 0.03% to about 0.3%, most preferably about 0.05% to about 0.2%.

The formulation of the invention may include a suitable dosage according to the disorder being treated. In one embodiment, the formulation of the invention comprises a dose of about 0.01 mg to 10 mg of DNase or enzymatically active portion thereof.

Alternatively, the formulation of the invention comprises a dose of about 0.1 mg to 5 mg; about 1 mg to 5 mg; about 2.5 mg to 5 mg, about 2.0 to 4.5 mg, about 2.2 to 4.0 mg, about 2.0 to 3.0 mg, about 2.2 to 3.0 mg, about 2.3 to 3.0 mg, about 2.4 to 2.8 mg, about 2.4 to 2.6 mg; or about 2.5 mg of the DNase or enzymatically active portion thereof. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Thus, in some embodiments, the dosage regimen includes, but is not limited to a single dose of the pharmaceutical composition of the invention, of 1.0 to 10 mg DNase I, administered daily, a single dose of 2.0 to 5 mg DNase I, administered daily, a single dose of 2.0-3.0 mg DNase I, administered daily, a plurality of doses, each dose comprising 1.0-3.0 mg DNase, the doses administered at least twice, 2-3 times, 2-4 times or 2-6 times daily, a plurality of doses, each dose comprising 1.0-3.0 mg DNase, the doses administered once every 36 hours, once every 36-48 hours, once every 36-72 hours, once every 2-3 days, once every 2-4 days, once every 2-5 days, or once every week, a plurality of doses, each dose comprising 1.0-3.0 mg DNase, the doses administered once every 36 hours, once every 36-48 hours, once every 36-72 hours, once every 2-3 days, once every 2-4 days, once every 2-5 days, or once every week.

Therapeutic compositions typically must be sterile and stable under the conditions of manufacture and storage. The formulation can be formulated as a solution, microemulsion, dispersion, liposome, or other ordered structure suitable to high drug concentration before processing into a liquid pharmaceutical composition. Sterile inhalable solutions can be prepared by incorporating the active compound (i.e., rhDNase, DNase I or other DNase) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. The proper fluidity of a solution can be maintained, for example, by the use of a coating such as lecithin, by the maintenance of the required particle size in the case of dispersion and by the use of surfactants. Prolonged action of inhalable compositions can be brought about by including in the composition an agent that delays absorption, for example, monostearate salts and gelatin.

In one embodiment, the DNase or active portion for use in the methods of the invention is incorporated into a pharmaceutical formulation as described in Examples 2-5. Supplementary active compounds can also be incorporated into the compositions for pulmonary delivery. In certain embodiments, a DNase or active portion for use in the methods of the invention is coformulated with and/or coadministered with one or more additional therapeutic agents mentioned hereinabove. For example, DNase I or active portion of the invention may be coformulated and/or coadministered with one or more additional compositions that reduce actin inhibition (e.g. magnesium or potassium salts), and/or one or more chemical agents that inhibit mucus production (such as anti-inflammatory agents, bronchodilators and/or mucus secretion blockers, as described in U.S. Pat. No. 7,763,610) or any combination thereof. Furthermore, the DNase of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

The formulations of the invention may include a "therapeutically effective amount" or a "prophylactically effective amount" of a DNase protein or active portion of the invention. A "therapeutically effective amount" refers to an amount effective, at to dosages and for periods of time necessary, to achieve the desired therapeutic result. A therapeutically effective amount of the DNase may vary according to factors such as the disease state, age, sex, and weight of the individual, and the ability of the DNase or active portion thereof to elicit a desired response in the individual. A therapeutically effective amount is also one in which any toxic or detrimental effects of the DNase are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The invention also pertains to packaged formulations or kits for pulmonary administration of a DNase, e.g., DNase I. In one embodiment of the invention, the kit comprises a DNase, such as DNase I, and instructions for pulmonary administration of the DNase, wherein the DNase is in a liquid pharmaceutical composition suitable for inhalation. The instructions may describe when, e.g., at day 1, day 4, week 0, week 2, week 4, etc., the different doses of DNase shall be administered via inhalation to a subject for treatment.

Another aspect of the invention pertains to kits containing a pharmaceutical composition comprising a DNase, such as DNase I, and a pharmaceutically acceptable liquid carrier, and one or more formulations each comprising an additional therapeutic agent, and a pharmaceutically acceptable carrier.

The package or kit alternatively can contain the DNase and it can be promoted for use, either within the package or through accompanying information, for the uses or treatment of the disorders described herein. The packaged formulations or kits further can include a second agent (as described herein) packaged with or copromoted with instructions for using the second agent with a first agent (as described herein).

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

For any preparation used in the methods of the invention, the therapeutically effective amount or dose can be estimated initially from in vitro and cell culture assays.

For example, a dose of the pharmaceutical composition can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually, for example, to provide serum and cell levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration.

Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form to prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The formulation can be used for treatment or prevention of a mucus-related respiratory condition in a subject in need thereof. Thus, according to another aspect of the present invention there is provided a method for treating or preventing a respiratory condition such as cystic fibrosis (CF) or COPD in a subject in need thereof, the method comprising administering to the subject an effective amount of the pharmaceutical composition which includes, as an active ingredient thereof, a human DNase I protein, and a liquid pharmaceutical acceptable carrier. In some embodiments of the present invention, the human DNase I protein has an N-terminal Glycine residue. In other embodiments, the human DNase I protein has an amino acid sequence as set forth in SEQ ID NO: 5.

In some embodiments of the invention, treatment of cystic fibrosis is effected by pulmonary administration of the pharmaceutical composition of the invention, the effective dosage being in a range of 0.1 to 50 mg DNase I protein (as active ingredient) per dose, 0.1 to 50 mg DNase I protein (as active ingredient) per dose, 0.5 to 25 mg DNase I protein (as active ingredient) per dose, 1.0 to 20 mg DNase I protein (as active ingredient) per dose, 1.5 to 15 mg DNase I protein (as active ingredient) per dose, 2.0 to 10 mg DNase I protein (as active ingredient) per dose, 2.5 to 7.5 mg DNase I protein (as active ingredient) per dose, 2.75 to 5 mg DNase I protein (as active ingredient) per dose or from 2.0 to 3.0 mg DNase I protein (as active ingredient) per dose. In some embodiments the effective dose of prh DNase I is 2.0-3.0 mg DNase I protein (as active ingredient) per dose, 2.1-2.9 mg DNase I protein (as active ingredient) per dose, 2.2-2.8 mg DNase I protein (as active ingredient) per dose, 2.3-2.7 mg DNase I protein (as active ingredient) per dose or 2.4-2.6 mg DNase I protein (as active ingredient) per dose. In some embodiments the effective dosage of prh DNase I is administered once to daily, once every 2 days, once every 2-5 days, once every 2-10 days or more. In some embodiments the effective dosage of prh DNase I is administered 2, 3, from 2-4, from 2-6, from 2-8 or more times per day. In some embodiments of the invention, 2.5 mg of prh DNase I is administered via pulmonary administration once daily for treatment of cystic fibrosis.

Excess DNA accumulated in secretions, fluids or tissues has been associated with a number of pathological and disease-relate conditions, not only in pulmonary conditions, but also in conditions such as sepsis, infertility and metastatic spread of cancer. The pharmaceutical compositions comprising human DNase I of the present invention, administered so as to reach the site of excess extracellular DNA, can effectively lyse such extra cellular DNA and thereby reduce the severity of, alleviate the symptoms of, treat, prevent or cure the DNA-relate condition. Thus, according to some embodiments of the present invention, the disease or condition is associated with excess extra-cellular DNA in a fluid, secretion or tissue of the subject, and the administering the pharmaceutical compositions results in nucleolysis of the extra-cellular DNA.

In yet other embodiments, the pharmaceutical composition of the invention, comprising human DNase, can be used for treatment or prevention of male infertility (see, for example US20110033438 to Bartoov et al. and US20070259367 to Ax et al.), and for the treatment or prevention of infectious disease caused by bacteria, virus, fungi and protozoa, treatment or prevention of sepsis (e.g. bacterial sepsis), treatment or prevention of tumors, both primary and metastatic, for prevention or reduction of metastatic growth, treatment and prevention of atherosclerosis, diabetes, delayed-type hypersensitivity reaction, treatment and prevention of diseases caused by somatic cell mutation and for enhancing longevity in an organism (see, for example US20080004561 to Genkin et al). Treatment of male infertility by the pharmaceutical composition comprising human DNase I may be directed towards reducing the amount of DNA in semen samples, as taught, for example, by Ax et al, via ex-vivo providing the semen samples with prh DNase I. In other embodiments, treatment of male infertility, tumors, metastatic transformation and growth, atherosclerosis, uterine and endometrial disorders, sepsis, viral, bacterial, fungal and protozoan infections, delayed type hypersensitivity reaction and diseases caused by somatic cell mutation is directed to reducing the amount of DNA in a subject, in-vivo, and the DNase can be administered by pulmonary to administration by any route or method suitable for delivery of the DNase to the desired target within the subject's body.

Thus, in some embodiments, there is provided method of treating a subject, wherein the subject is suffering from a disease or condition selected from the group consisting of male infertility, metastatic cancer, a viral, bacterial, fungal or protozoan infection sepsis, atherosclerosis, diabetes, delayed type hypersensitivity and a uterine disorder, by administering to the subject an effective amount of the pharmaceutical composition comprising human DNase I in a liquid carrier of the invention via pulmonary administration.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., a damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, to chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

It is expected that during the life of a patent maturing from this application many relevant vectors, promoter elements, plant cells and carriers will be developed and the scope of the terms provided herein is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1, 2, 317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein.

Other general references are provided throughout this document. The procedures therein are believed to be well known in the art and are provided for the convenience of the reader. All the information contained therein is incorporated herein by reference.

Example 1

Construction of the Plant Deoxyribonuclease I Expression Construct cDNA encoding the human deoxyribonuclease I (DNase I) protein (EC 3.1.21.1 GenBank: NM_005223) was optimized and synthesized by GENEART AG (Regensburg, Germany). The codon usage without the 22 amino acid leader peptide (e.g. endoplasmic reticulum target signal peptide) was adapted to the codon bias of *Nicotiana tabacum* genes. During the optimization process the following cis-acting sequence motifs were avoided: Internal TATA-boxes, chi-sites and ribosomal entry sites, AT-rich or GC-rich sequence stretches, RNA instability elements ("killer motifs"), Repeat sequences and RNA secondary structures, splice donor (cryptic) and acceptor sites, branch points. In addition, regions of very high (>80%) or very low (<30%) GC content were avoided.

The nucleotide sequence of the native human DNase I leader peptide (endoplasmic reticulum target signal peptide) (FIG. 1, first 22 amino acids in red) of the full length human DNase I protein (GenBank: NM_005223) was replaced with a nucleotide sequence encoding the 33 amino acid endoplasmic reticulum targeting signal peptide (leader peptide) of the *Arabidopsis* ABPI protein (marked in green in FIG. 1, SEQ ID NO: 4). This ER targeting signal peptide provides efficient targeting of DNase I to the secretory pathway and is then cleaved from the polypeptide, by signal peptidase, once the protein has been translocated into the endoplasmic reticulum. In some cases the cleavage of ABPI signal is not complete and the last (C-terminal) amino acid Glycine of the signal peptide remains, being added to the N terminal of the mature DNase I protein. As the optimized DNase I coding sequence does not contain any compartment (organelle) localization signal at the 3' terminus, the recombinant DNase I, absent a C-terminal localization signal is directed to the plant cell apoplast (the extracellular space surrounding the plant cell symplast), and when expressed in plant cell cultures, is subsequently secreted into the culture medium. SEQ ID NO: 1 represents the complete coding sequence of the expressed recombinant human DNase I polypeptide, including the N-terminal ABPI endoplasmic reticulum targeting signal peptide (SEQ ID NO: 4) and the human DNase I protein (SEQ ID NO: 6).

Example 2

Expression of Recombinant hDNase I in Plants

Transient Expression System in *N. benthamiana*

The use of plant viral vectors was chosen in this case as an alternative to transgenic plants, allowing for the rapid, high level transient expression of proteins in mature whole plants.

The protein of interest was expressed from a strong subgenomic viral coat protein promoter. The system relies on transient amplification (by agroinfection) of viral vectors delivered to a plant by *Agrobacterium*, in which the plant functional promoter and the cDNA encoding a viral replicon are transferred as T-DNA from *Agrobacterium* into plant cells. The T-DNA is transcribed in-planta by the plant promoter to generate biologically active viral RNA that initiates self replication.

For the transient expression a 3-vector recombination system based on the system previously developed as described (Gleba et al., Vaccine 23 2042-2048, 2005) was employed. DNase I cDNA was inserted into one of the vectors, and the two other vectors contained genes for construction of the whole viral replicon (RdRp and Integrase), thus generating a biologically active viral RNA capable of initiating self replication.

Transfection of Whole Plants—

*N. Benthamiana* plants were germinated and grown in commercial mix soil (Givaat Ada, Ill.) supplemented with granular slow release fertilizer (Scott Marysville, Ohio) under a long day (16 h light/8 h dark) light regime at 24'C-25'C.

*Agrobacteria* were transformed with the pICH20866-DNaseI based replicon vector system using electroporation (2500V, 5 msec) [den Dulk-Ra, A. and Hooykaas, P. J. (1995) Methods Mol. Biol. 55:63-72]. Plants were infiltrated with *Agrobacteria* containing the 3 ICON plasmids by vacuum infiltration with standard methods known in the art. Briefly, *N. benthamiana* plants 5-6 week old were infiltrated by immersing all aerial plant organs into a bacterial suspension and were placed in a vacuum chamber. A minus (−) 0.8 bar vacuum was applied for 1 minute, followed by a quick return to atmospheric pressure. Plants were returned to the greenhouse for additional 5-7 days under the same growth conditions.

Screening for targeting to plant cell compartments was accomplished using the 3 vector recombination system described above, with the DNase I-based vector including a sequence encoding an N-terminal *Arabidopsis* ABPI signal peptide (marked in green in FIG. 1, SEQ ID NO: 4), followed by the nucleotide sequence of human DNase I, and further followed by one of the below:

1) A nucleotide sequence (SEQ ID NO: 14) encoding the endoplasmic reticulum retention signal SEKDEL (SEQ ID 13), allowing retrieval of the expressed protein from the Golgi apparatus, effectively maintaining the protein in the endoplasmic reticulum;

2) A nucleotide sequence (SEQ ID NO: 16) encoding for the vacuole targeting signal peptide GLLVDTM (SEQ ID 15), allowing transfer of the expressed protein from the Golgi apparatus to the cell vacuole; or 3) No addition of any compartment localization signal at the 3' terminus of the nucleic acid sequence, directing localization of the expressed DNase I protein to the plant cell apoplast, by default.

Tobacco Plant Extract:

Samples of *Nicotiana benthamiana* leaves were harvested 5 days post infiltration and extracted in Laemmli buffer for SDS-PAGE, or in extraction buffer (25 mM HEPES-NaOH, 40 mM $CaCl_2$, 40 mM $MgCl_2$, pH 7.5) for assays of catalytic activity and ELISA of the plant expressed protein.

Tobacco Plant Extract Purification:

Human DNase I protein from plant extracts was purified by centrifugation of the homogenized plant mass, discarding the plant debris. The supernatant was heated to 60° C. for 10 minutes and filtered through a 3 μm filter, followed by filtration through a 0.65 μm filter. The filtrate was further purified on a hydrophobic interaction chromatography resin (Butyl 650C, Toyopearl) followed by further purification on an anion exchange chromatography resin (Poros 50HQ). The final material was filtered for sterility (0.2 μm).

Stable Expression in *N. tabacum* BY2 Cells

*Agrobacterium* mediated transformation is widely used to introduce foreign genes into a plant cell genome. This technique is based on the natural capability of the *agrobacterium* to transform plant cells by transferring a plasmid DNA segment, the transferred DNA (T-DNA), into the host cell genome. Using this approach, a T-DNA molecule, consisting of a foreign gene and its regulatory elements, is randomly introduced into the plant genome. The site of integration, as well as the copy number of to the gene insertions is not controlled, thus the transformation process results in a ‘pool’ of transgenic cells composed of cells with various levels of expression of the transgene.

The transgenic ‘pool’ is subsequently used for clone isolation. Clone isolation results in the establishment of many single cell lines, from which the clone with the highest expression level of the foreign gene is then selected.

BY2 (Bright Yellow 2) suspension culture was co-cultivated, for 48 hours, with the *Agrobacterium tumefactiens* EHA105 strain carrying the vector harboring the DNase I gene and the neomycin phosphotransferase (NPTII) selection gene.

Subsequently, the cells were kept in media supplemented with 50 mg/L of Kanamaycin and 250 mg/L Cefotaxime. The NPTII gene confers resistance to Kanamycin, thus only NPTII positive BY2 cells survive in this selection media. The Cefotaxime was used to selectively kill the *agrobacterium*, the plant cells being resistant to this antibiotic. Once a nicely growing transgenic cell suspension was established, it was used for screening and isolating individual cell lines. To allow for the selection of individual cell lines, aliquots of highly diluted cell suspension were spread on solid BY-2 medium. The cells were then grown until small calli developed. Each callus was then re-suspended in liquid culture. Media was then sampled and evaluated for DNase I levels. The lines that secreted relatively high DNase I levels were then further re-analyzed and compared for DNase I levels ending with the final selection of candidate DNase I expressing lines.

Media samples of transformed BY2 cells expressing the human DNase I protein were collected and when required, concentrated 5× by centrifugal filters (Amicon Ultra, 10K, #UFC501096). DNase I catalytic activity in cell’s media was determined by DNA-Methyl Green assay and compared to total DNase I amount, determined by Enzyme-linked immunosorbent assay (ELISA 1) as described hereinbelow.

Protein Purification from BY-2 Cells:

Recombinant human DNase-I protein secreted from tobacco suspension plant cells was purified by the following steps: at the end of the fermentation the intact tobacco cells were separated from the media by filtration using 100 mesh filter bags. The cells were discarded and the media containing the prhDNAse-I was collected for additional filtration with 0.2 μm filter sheets using filter-press apparatus. The DNase in the filtrated media was further purified by two steps of chromatography columns of an anion exchange resin (Poros 50HQ, Applied Biosystems, USA) followed by hydrophobic interaction chromatography of Phenyl 650C resin (Toyopearl, Japan). The purified DNase collected from the last column was 0.2 μm filtrated and stored at 4° C.

Gel Electrophoresis:

Sodium Dodecyl Sulfate-Polyacrylamide Gel Electrophoresis (SDS-PAGE) separates proteins primarily by their molecular weight, proteins migrating as a linear function of the logarithm of their molecular weight in SDS-PAGE. For estimating the molecular weight of prh DNase I, migration on SDS-PAGE was compared to commercial molecular weight standard proteins (New England BioLabs; cat No. P7708S) and to the migration of commercially available, mammalian-cell derived recombinant human DNase I, Pulmozyme® (Genentech, Calif.), expressed in CHO cells. prh DNase I and Pulmozyme were analyzed by 15% Tris-Glycine SDS-PAGE.

Electrophoresis was performed using Criterion™ cell vertical electrophoresis apparatus (Bio-Rad Lab.) with premixed electrophoresis Tris-Glycine-SDS running buffer (Bio-Rad Laboratories). Fifteen percent acrylamide gels were prepared using premixed solutions of 40% Acrylamide/Bis and 10% SDS solution. Identification of the proteins was performed using two methods of detection: Coomassie brilliant blue staining and Western blot analysis using specific antibodies and Enhanced Chemical Luminescence (ECL).

Coomassie Blue Staining

Following SDS-PAGE, gels were stained with Bio-Safe™ Coomasie Stain (Bio-Rad) according to manufacturer’s instructions.

Western Blotting

Western Blot

Antibodies: Detection of rh DNase1 was carried out by using either (a) whole antiserum obtained from rabbits immunized against Pulmozyme®. These antibodies were prepared according to a standard polyclonal antibody preparation protocol including four immunizations with 3 mg antigen per rabbit, and collection of the serum after the fourth immunization; or (b) affinity purified rabbit anti-prh DNase I and goat-anti-prh DNase I acquired following immunization of rabbits and goats with prh DNase and affinity purification on a Pulmozyme® column Thus, the purified antibodies detect the common backbone sequence of Pulmozyme and prh- DNase. These antibodies were prepared by GenScript USA Inc in accordance to GenScript standard polyclonal antibody preparation protocol including four immunizations with 3 mg antigen per rabbit and 8 mg antigen per goat, and collection of the serum after the forth immunization.

PAGE and Blotting: Following SDS-PAGE, proteins were transferred to a nitrocellulose membrane using iBlot™ Dry Blotting System (Invitrogen). Transfer was performed at room temperature for 8 min. Then, the membrane was blocked with 5% (v/w) non-fat dry milk powder in PBS supplemented with 0.05% (v/v) Tween-20, washed with PBS supplemented with 0.05% (v/v) Tween-20, bound to the primary antibody, followed by wash with PBS supplemented with 0.05% (v/v) Tween-20 and incubation with secondary HRP-conjugated antibody. Primary antibody was diluted 1:5000 (whole antiserum) or 1:10000 (affinity purified rabbit and goat anti prh DNase I) in 1% (w/v) non-fat dry milk powder in PBS supplemented with 0.05% (v/v) Tween-20, and the secondary antibody-goat anti-rabbit or rabbit anti-goat HRP conjugated antibody (Jackson ImmunoResearch Laboratories, Inc., PA; cat No. 111-035-003 and cat No. 305-035-003respectively) was diluted 1:10,000 in 1% (w/v) non-fat dry milk powder in PBS supplemented with 0.05% (v/v) Tween-20. Enhanced Chemi-Luminescence (ECL) reaction was performed with ECL detection kit (Pierce; cat. No. 34080). The immunoreactive bands were detected and documented using the Molecular Imager Gel Doc XR System (Bio-Rad Laboratories, UK) for time intervals up to 60 seconds, as needed.

Isoelectric Focusing

Isoelectric Focusing (IEF) separates proteins on the basis of their charge in an electrical field. The protein migrates in a pH gradient generated by an electric field until it reaches a point in which its net charge equals zero, and that pH reflects its isoelectric point (pI). To identify the pI of rh DNase I, protein was analyzed by polyacrylamide IEF gels using an XCell SureLock Electrophoresis Cell equipped with a Powerpac power supply (BIO-RAD) and by Imaged capillary isoelectric focusing (iCE) using an iCE280 analyzer (Convergent Bioscience, Toronto Canada). Pre-cast polyacrylamide IEF gels with a pH range of 3-7 were obtained from Invitrogen (Novex®, Invitrogen, cat No. EC6645BOX/EC66452BOX); buffers were obtained from Invitrogen (anode buffer: Novex®, cat. No LC5300; cathode buffer: Novex®, cat. No. 5370; sample buffer: Novex®, cat. No. 5371); pI protein standards were obtained from SERVA (cat. No. 39212). Electrophoresis conditions: 100 mV-1 h, 200 mV-1 h, 500 mV-1.5 h. Bands were visualized by Bio-Safe™ Coomassie Stain (Bio-Rad, cat No. 161-0787) according to the manufacturer's instructions. The pI profile of rh DNase I was estimated using the pI protein standards, and then the banding profile was compared to that of Pulmozyme®.

For imaged capillary isoelectric focusing analysis, a sample contained prh DNase I, pI markers 3.59 and 5.85 (protein simple, cat No. 102222 and 102225, respectively), 0.35% methylcellulose (protein simple, cat No. 101876), and SERVALYT pH 3-7 (SERVA, cat No. 42945.01) was introduced to the capillary through an autosampler (PrinCE) and was focused in a capillary column under high voltage. The focusing process was monitored in real-time using whole column imaging detection (WCID).

The resolved charge species appear as electrophoretic peaks that are detected at a fixed wavelength of UV280 nm. pI values and peak areas for each species were determined from the resultant electropherograms.

Mass Spectrometry

Molecular Weight Analysis

Molecular weight analysis was accomplished by mass spectrometry (MS) of rh DNase I, using a matrix-assisted laser desorption ionization time-of-flight (MALDI-ToF) mass spectrometer and sinapinic acid as a matrix. The equipment was calibrated using molecular weight standards. About 2.5 micrograms of rh DNase were used for mass analysis.

Amino Acid Sequence and Structural Characterization prh DNase I sequence was analysed using reverse-phase (RP-) HPLC coupled to mass spectrometry.

The protein samples were reduced using 2.8 mM DTT (60° C. for 30 minutes), modified using 8.8 mM iodoacetamide in 100 mM ammonium bicarbonate (in the dark, room temperature for 30 minutes) and digested in 10% ACN and 10 mM ammonium bicarbonate with modified trypsin (Promega) or with chymotrypsin overnight at 37° C. in a 1:50 enzyme-to-substrate ratio. 3% of the resulting peptides were resolved by reversed-phase liquid chromatography on a 0.075×200-mm fused silica capillaries (J&W) packed with Reprosil reversed phase material (Dr Maisch, GmbH, Germany).

Peptides were eluted with a linear 60 minutes gradient of 5 to 45% followed by 15 minutes at 95% acetonitrile with 0.1% formic acid in water at flow rates of 0.25 μL/min. On-line mass spectrometry was performed by an ion-trap mass spectrometer (Orbitrap, Thermo) in a positive mode using repetitively full MS scan followed by collision-induced dissociation (CID) of the 7 most dominant ions selected from the first MS scan. The mass spectrometry data was analyzed using the Sequest 3.31 software (J. Eng and J. Yates, University of Washington and Finnigan, San Jose), compared to the human reference sequence.

Further sequencing and structural characterization data was obtained from trypsin digestion of prhDNase I, with or without a further digestion with PNGaseA in the presence and absence of DTT and analysis by mass spectrometry.

Disulfide Bonds and Free Sulfhydryl Content

Human DNase-1 sequence includes four cysteine residues and contains two disulfides bonds. It was expected that the structure a recombinant human DNase-1 expressed in plant cells (prhDNase I), will be similar to the authentic human protein.

The assessment of the prhDNase I thiol content was obtained by using the Ellman's method, which is a rapid and sensitive method for quantitative analysis of the total free thiols in peptides and proteins. The number of free thiols found on prhDNase I also indicates the number of cysteine residues that are engaged in disulfide bonds.

Free thiols analysis of prhDNase I and Pulmozyme®-was carried out according to standard Ellman's method under denaturing conditions. The reaction was performed by mixing the protein solution in sodium phosphate buffer with 6M Guanidine Hydrochloride and the active substrate DTNB [5,5'-Dithiobis (2-nitrobenzoic acid)].

The solutions were incubated at ambient conditions for 5-15 min During the reaction, TNB (2-nitro-5-thiobenzoic acid) was released. A reaction of 1 mole DTNB with 1 mole thiol releases 1 mole of TNB anion with an extinction coefficient of 13,700 $M^{-1}$ $cm^{-1}$ at 412 nm. The number of thiols was calculated as direct ratio between TNB concentration and prhDNase I concentration in the analyzed sample. A protein, containing free thiols was used as positive control and DNase I formulation buffer (1 mM $CaCl_2$, 150 mM NaCl, pH 6.1-6.5) was used as blank for analysis.

Glycan Structure of rh DNase

Glycan Analysis of the Plant-Expressed Human DNAseI:

Samples of recombinant human DNAseI protein product from the transformed cells were reduced with DTT alkylated with iodoacetamide, and separated on a 12.5% SDS-PAGE. Bands corresponding to the correct molecular weight were excised and subjected to glycan analysis consisting of trypsin digestion followed by peptide extraction and by both PNGase A and PNGase F digestion. PNGase A digestion releases all the N-linked glycans and PNGase F release all glycans except those containing α 1-3 core fucose.

The free glycans were released, purified and then labeled with the fluorescent reagent anthranilamide (2AB) followed by removal of excess 2AB.

Glycans were separated using a TSK gel Amide 80 normal phase HPLC and detected using a fluorescence detector. A Dextran hydrolysate served as a ladder for calculation of glucose unit (GU) values. Glycan profile is constructed by calculating the relative peak areas from the chromatogram of the PNGase A digestion. Assignment of the glycans is established by calculation of the GU values of the peaks found in both endoglycoside digestions and based on additional various exoglycoside digestions, comparison to known databases and confirmation of results by mass spectrometric methods.

Reverse Phase-High Performance Liquid Chromatography (RP-HPLC)

RP-HPLC was used as an analysis method for the determination of purity of hr DNase I. The analysis employed a Jupiter 3μ, C18, 300 Å, 250×4 6 mm column by Phenomenex. Analyses were performed on a Dionex, Ultimate 3000 HPLC system equipped with a photodiode array detector. Chromatograms were routinely recorded at 2 wavelengths, 214 and 280 nm Elution Solvents:

Solvent A: 1 Liter, 0.1% TFA/$H_2O$(HPLC grade, J. T. Baker, cat #4218-03). Solvent A was prepared by adding 1.0 mL of TFA (Sigma, cat. # T6508) to 0.999 liter of water (HPLC grade, J. T. Baker, cat. #4218-0.3).

Solvent B: 1 Liter, 0.1% TFA/Acetonitrile (HPLC grade, Sigma, cat. #34888). Solvent B was prepared by adding 1.0 mL TFA (Sigma, cat. # T6508) to 0.999 liter of acetonitrile (HPLC grade, Sigma, cat. #34888).

Chromatographic Method:

Chromatographic separations were performed on a Jupiter 3p, C18, 300 Å, 250×4.6 mm column (Phenomenex, cat. 00G-4263-E0). Chromatograms were obtained using a linear gradient of 5% B for 3 min, followed by 5% B to 43% B for 10 min, followed by 43% B to 55% B for 30 min, followed by 55% B to 95% B for 10 min followed by 95% B for 3 min followed by 95% B to 5% B for 2 min, followed by 5% B for 21 min at a flow rate of 1 ml/min and at a temperature of 55° C. Each analysis sequence was commenced with a run of DNase I formulation buffer (1 mM $CaCl_2$.150 mM NaCl, pH 6.1-6.5) as a blank for rh DNase I.

Samples of prh DNase I (25 μg) in DNase I formulation buffer were analyzed. 25 μg of the rh DNase I was pipetted into a glass insert (250 μL), which was inserted into an HPLC auto-sampler glass vial.

Results

Characterization of Plant-Expressed hr-DNase I:

Yields of hr DNase I expressed in plant cells of whole tobacco plants varied with targeting to different plant organelles. FIG. 2 shows the differences in yield of plant expressed human DNase I (relative to that of apoplast targeting) when phr DNase I was expressed from a DNase I construct encoding an N-terminal ER targeting signal peptide only (APO) directing the protein to the apoplast, from a DNase I construct encoding an N-terminal ER targeting signal peptide and a C-terminal vacuolar targeting signal peptide (VAC), or from a DNase I construct encoding an N-terminal ER targeting signal peptide and a C-terminal ER retention signal peptide, targeting the protein for retention in the ER (ER). Clearly, targeting to the apoplast results in the highest yield of these three expression options. Further, FIG. 2 also reveals the consistent correlation between levels of immunoreactive DNase I protein and catalytic activity.

FIG. 3 shows an exemplary result of the migration of prh DNase I on SDS-PAGE (lanes 6-9), compared with mammalian cell expressed recombinant human DNase I (Pulmozyme®) (lanes 1-4). The plant expressed prh DNase I consists of one major band at a molecular weight of ~30 KDa, migrating similarly that of the commercial preparation. The prh DNase I preparation did not contain any detectable contamination, indicating a high purity. An apparent slight difference in migration characteristics was observed between the prh DNase I and the commercial preparation, with the plant expressed DNase I appearing to migrate faster. Without wishing to adhere to a single hypothesis, one possible explanation for such a difference in migration characteristics could be a difference in glycosylation patterns between the plant and mammalian cell-expressed enzymes. In order to compared for consistency between expression of phrDNase I from plants and plant cell culture, 3 batches of prh DNase I extracted from whole plants and 3 batches of prh DNase I extracted from cultured cells were analyzed on SDS-PAGE, and were observed to have the same, characteristic pattern of migration on the gel.

FIG. 4 shows an exemplary result of immunological cross reactivity of the prh DNase I separated on SDS-PAGE (lanes 6-9), compared with the commercial, mammalian cell expressed recombinant human DNase I (Pulmozyme) (lanes 1-4), when reacted with unfractionated rabbit anti-human DNase I immune serum. The cross-reactive plant-expressed prh DNase I protein migrated as the 30 kDa molecular weight, similar to the commercial preparation. Further, note that the plant-expressed prh DNase I preparation does not contain any other detectable DNase I-related immunoreactive species, indicating high purity of the preparation. Three batches of DNase extracted from whole plant and 3 batches of DNase extracted from cultured cells were analyzed and have shown the same migrating characteristics. In addition, the same results were obtained using affinity purified rabbit anti-prh DNase.

FIGS. 5A-5D show a typical pI analysis of the plant-expressed prh DNase I as compared to Pulmozyme®. The rh DNase I is characterized by 3 bands; two major isoforms ranged between 4.2-4.5 and a minor isoform with a slightly lower pI (FIG. 5A, lanes 2 and 3 and 5B, lane 2). This is in contrast to the commercial standard, Pulmozyme® (FIG. 5A, lane 1 and 5B, lane 3), which is characterized by a variety of isoforms ranging from pI 3.5 to pI 4.5. Without wishing to adhere to a single hypothesis, one possible explanation for such a difference in pI could be a difference in glycosylation patterns between the plant and mammalian cell-expressed enzymes. Three batches of DNase extracted from whole plant and 3 batches of DNase extracted from cultured cells from cultures of different transformed BY2 lines were analyzed, and demonstrated the same migration pattern upon pI analysis. pI values for each species were determined from imaged capillary isoelectric focusing electropherograms (FIGS. 5C and 5D). A main peak (MP, pI 4.41) and two acidic peaks (pre-MP1 and pre-MP2 with to pI of 4.27 and 4.21) were observed, consistent with the pI profile observed in the IEF gels (FIGS. 5A and 5B).

FIGS. 6A and 6B depict an analysis of the molecular weight of plant-expressed prh DNase I by MALDI-ToF, showing the entire spectrum from 20000 to 180000 m/z (6A) or an enlargement of the prh DNase I peak at about 32000 m/z (6B). The molecular weight of the prh DNase I enzyme extracted from the plant cells was approximately 32,070 Da, while the theoretical molecular weight of the prh DNase I polypeptide, based on the proteins' 261 amino acid sequence, is 29,311 Da. Without wishing to adhere to a single hypothesis, one likely explanation for such a difference in the chromatographic characteristics is the difference in glycosylation patterns. Therefore, glycan structures may add the remaining ~2760 Daltons. Three batches of prh DNase Iextracted from cultured cells were analyzed and have shown similar characteristics.

The difference in the molecular weight of the three phr DNase I main isoforms seen in the MALDI analysis was approximately 200 Da. (FIG. 6B) This may correspond to a difference in glycan structures that can be attributed to one or two residues of N-Acetylglucosamine (203 Da). The same indication can be found in the variability of glycan structures.

Thus, the results of the mass spectrometry analysis confirm the molecular weight determination from the SDS-PAGE analysis (see FIG. 3), and both are consistent with a molecular weight of the prh DNase I comparable to the calculated molecular weight of the expressed polypeptide, and consistent with the molecular weight of mammalian cell expressed recombinant human DNase I (Pulmozyme®).

Amino Acid Sequence of Plant-Expressed Rh DNase I

Mass spectrometry analysis of the peptides generated by trypsin and chymotrypsin digestion of plant-expressed rh DNase I showed over 97.3% coverage of the 261 DNase I amino acid sequences that matched the predicted amino acid sequence based on the DNA sequence of the expression cassette (SEQ ID NO: 6). FIG. 7 represents the composite amino acid sequence derived from the overlapping peptides, with unconfirmed amino acids in red, putative glycosylation sites bolded and underlined, and the additional N-terminal glycine marked in green. When compared to the peptide sequence of the native human enzyme (SEQ ID NO: 6, GenBank Accession No: to NP_005214.2) it is apparent that the amino acid sequence of plant-expressed rh DNase I is identical to that of commercial, mammalian cell expressed dornase alfa (Pulmozyme®), and in some embodiments, with an additional glycine residue at position 1 at the N terminus, derived from the ABPI signal peptide. Indeed, further HPLC and MS analysis of a trypsin digest and chymotrypsin sub-digest of the plant-expressed rh DNase I provided a full 261 amino acid sequence, confirming the accuracy of the sequence derived from overlapping peptides (FIG. 7) and the identity of the amino acid sequence of the plant expressed rh DNase I and that of commercial, mammalian cell expressed dornase alfa (Pulmozyme®), with the addition of a glycine residue at position 1 at the N terminus, derived from the ABPI signal peptide. Furthermore, the analysis of the trypsin digest of prhDNAse I treated and not treated with PNGase A revealed the presence of glycan sites on Asp 19 and Asp 107 as supported by the glycan analysis data in FIG. 8 (below). In addition, disulphide bridges were observed between Cys102 and Cys105 and between Cys174 and Cys210. The overlapping peptides are presented in the following coverage table (Table V), in which the first amino acid of plant-expressed rh DNase I, Gly, is numbered as amino acid 33, and where amino acids 1-32 are comprised of the ABPI signal sequence (SEQ ID NO: 4), which are cleaved from the expressed polypeptide following transfer to the endoplasmic reticulum. Table Va shows peptides produced by trypsin and PNGase digestion. In this table Gly, is denoted as amino acid number 1.

TABLE V

Peptides Identified Following Digestion with Trypsin and Chymotrypsin

| Position | % Mass | SEQ ID NO: | Sequence |
|---|---|---|---|
| 33-48 | 5.325060547 | 17 | GLKIAAFNIQTFGETK |
| 34-39 | 2.029654905 | 18 | LKIAAF |
| 34-44 | 3.878161246 | 19 | LKIAAFNIQTF |
| 34-48 | 5.150347722 | 20 | LKIAAFNIQTFGETK |
| 35-48 | 4.803860015 | 21 | KIAAFNIQTFGETK |
| 36-42 | 2.378969069 | 22 | IAAFNIQ |
| 36-44 | 3.139192685 | 23 | IAAFNIQTF |
| 36-45 | 3.313905509 | 24 | IAAFNIQTFG |
| 36-48 | 4.411379161 | 25 | IAAFNIQTFGETK |
| 38-48 | 3.847234909 | 26 | AFNIQTFGETK |
| 39-48 | 3.629578364 | 27 | FNIQTFGETK |
| 40-44 | 1.906776692 | 28 | NIQTF |
| 40-48 | 3.178963169 | 29 | NIQTFGETK |
| 42-48 | 2.483049813 | 30 | QTFGETK |
| 43-48 | 2.090680443 | 31 | TFGETK |
| 49-57 | 3.019451292 | 32 | MSNATLVSY |
| 49-64 | 5.499783699 | 33 | MSNATLVSYIVQILSR |
| 53-64 | 4.264530922 | 34 | TLVSYIVQILSR |
| 55-64 | 3.608434794 | 35 | VSYIVQILSR |
| 58-64 | 2.538602758 | 36 | IVQILSR |
| 58-65 | 3.038226108 | 37 | IVQILSRY |
| 59-64 | 2.192115051 | 38 | VQILSR |
| 60-64 | 1.888571065 | 39 | QILSR |
| 63-74 | 4.439055196 | 40 | SRYDIALVQEVR |
| 65-70 | 2.124510303 | 41 | YDIALV |
| 65-71 | 2.516879673 | 42 | YDIALVQ |
| 65-73 | 3.215808036 | 43 | YDIALVQEV |
| 65-74 | 3.694099266 | 44 | YDIALVQEVR |
| 65-75 | 4.046539923 | 45 | YDIALVQEVRD |
| 65-78 | 5.079638575 | 46 | YDIALVQEVRDSHL |
| 65-83 | 6.477641206 | 47 | YDIALVQEVRDSHLTAVGK |
| 66-71 | 2.017256323 | 48 | DIALVQ |
| 66-74 | 3.194475917 | 49 | DIALVQEVR |

TABLE V-continued

Peptides Identified Following Digestion with Trypsin and Chymotrypsin

| Position | % Mass | SEQ ID NO: | Sequence |
|---|---|---|---|
| 66-83 | 5.978017857 | 50 | DIALVQEVRDSHLTAVGK |
| 67-74 | 2.84203526 | 51 | IALVQEVR |
| 68-73 | 2.017256323 | 52 | ALVQEV |
| 68-74 | 2.495547553 | 53 | ALVQEVR |
| 69-74 | 2.277891008 | 54 | LVQEVR |
| 70-74 | 1.931403301 | 55 | VQEVR |
| 72-83 | 4.019031885 | 56 | EVRDSHLTAVGK |
| 74-83 | 3.320103521 | 57 | RDSHLTAVGK |
| 75-82 | 2.449331437 | 58 | DSHLTAVG |
| 75-83 | 2.841812291 | 59 | DSHLTAVGK |
| 75-106 | 10.83964091 | 60 | DSHLTAVGKLLDNLNQDAPDTYHYVVSEPLGR |
| 76-83 | 2.489371635 | 61 | SHLTAVGK |
| 83-96 | 4.963013347 | 62 | KLLDNLNQDAPDTY |
| 84-89 | 2.149025427 | 63 | LLDNLN |
| 84-90 | 2.541394797 | 64 | LLDNLNQ |
| 84-91 | 2.893835453 | 65 | LLDNLNQD |
| 84-92 | 3.111491998 | 66 | LLDNLNQDA |
| 84-95 | 4.070909143 | 67 | LLDNLNQDAPDT |
| 84-96 | 4.570532493 | 68 | LLDNLNQDAPDTY |
| 84-97 | 4.990478738 | 69 | LLDNLNQDAPDTYH |
| 84-98 | 5.490102088 | 70 | LLDNLNQDAPDTYHY |
| 84-106 | 8.056098967 | 71 | LLDNLNQDAPDTYHYVVSEPLGR |
| 84-110 | 9.564293519 | 72 | LLDNLNQDAPDTYHYVVSEPLGRNSYK |
| 84-112 | 10.43796913 | 73 | LLDNLNQDAPDTYHYVVSEPLGRNSYKER |
| 85-99 | 5.447158367 | 74 | LDNLNQDAPDTYHYV |
| 86-96 | 3.877557079 | 75 | DNLNQDAPDTY |
| 86-106 | 7.363123553 | 76 | DNLNQDAPDTYHYVVSEPLGR |
| 87-106 | 7.010682896 | 77 | NLNQDAPDTYHYVVSEPLGR |
| 88-106 | 6.661257247 | 78 | LNQDAPDTYHYVVSEPLGR |
| 90-106 | 5.965343891 | 79 | QDAPDTYHYVVSEPLGR |
| 91-106 | 5.572974522 | 80 | DAPDTYHYVVSEPLGR |
| 92-98 | 2.654536986 | 81 | APDTYHY |
| 92-106 | 5.220533865 | 82 | APDTYHYVVSEPLGR |
| 93-106 | 5.00287732 | 83 | PDTYHYVVSEPLGR |

TABLE V-continued

Peptides Identified Following Digestion with Trypsin and Chymotrypsin

| Position | % Mass | SEQ ID NO: | Sequence |
|---|---|---|---|
| 94-106 | 4.705509252 | 84 | DTYHYVVSEPLGR |
| 95-106 | 4.353068596 | 85 | TYHYVVSEPLGR |
| 97-102 | 2.246976996 | 86 | HYVVSE |
| 97-104 | 2.890832771 | 87 | HYVVSEPL |
| 97-105 | 3.065545596 | 88 | HYVVSEPLG |
| 97-106 | 3.543836826 | 89 | HYVVSEPLGR |
| 97-107 | 3.893262475 | 90 | HYVVSEPLGRN |
| 97-110 | 5.052031378 | 91 | HYVVSEPLGRNSYK |
| 98-106 | 3.12389058 | 92 | YVVSEPLGR |
| 99-104 | 1.971263176 | 93 | VVSEPL |
| 99-107 | 2.97369288 | 94 | VVSEPLGRN |
| 99-110 | 4.132461783 | 95 | VVSEPLGRNSYK |
| 111-115 | 2.22867221 | 96 | ERYLF |
| 113-120 | 3.286263893 | 97 | YLFVYRPD |
| 113-122 | 3.982177249 | 98 | YLFVYRPDQV |
| 113-123 | 4.248841949 | 99 | YLFVYRPDQVS |
| 113-124 | 4.466498494 | 10 | YLFVYRPDQVSA |
| 113-126 | 5.122483137 | 101 | YLFVYRPDQVSAVD |
| 113-128 | 5.888771186 | 102 | YLFVYRPDQVSAVDSY |
| 113-129 | 6.388394536 | 103 | YLFVYRPDQVSAVDSYY |
| 113-131 | 7.240458542 | 104 | YLFVYRPDQVSAVDSYYYD |
| 113-132 | 7.592899198 | 105 | YLFVYRPDQVSAVDSYYYDD |
| 113-133 | 7.767612023 | 106 | YLFVYRPDQVSAVDSYYYDDG |
| 114-128 | 5.389147837 | 107 | LFVYRPDQVSAVDSY |
| 114-129 | 5.888771186 | 108 | LFVYRPDQVSAVDSYY |
| 115-128 | 5.04266013 | 109 | FVYRPDQVSAVDSY |
| 115-129 | 5.542283479 | 110 | FVYRPDQVSAVDSYY |
| 116-123 | 2.952115698 | 111 | VYRPDQVS |
| 116-125 | 3.473316229 | 112 | VYRPDQVSAV |
| 116-126 | 3.825756886 | 113 | VYRPDQVSAVD |
| 116-128 | 4.592044935 | 114 | VYRPDQVSAVDSY |
| 116-129 | 5.091668284 | 115 | VYRPDQVSAVDSYY |
| 116-130 | 5.591291634 | 116 | VYRPDQVSAVDSYYY |
| 116-131 | 5.94373229 | 117 | VYRPDQVSAVDSYYYD |
| 116-132 | 6.296172947 | 118 | VYRPDQVSAVDSYYYDD |
| 116-133 | 6.470885771 | 119 | VYRPDQVSAVDSYYYDDG |

TABLE V-continued

| Peptides Identified Following Digestion with Trypsin and Chymotrypsin | | | |
|---|---|---|---|
| Position | % Mass | SEQ ID NO: | Sequence |
| 118-128 | 3.788877599 | 120 | RPDQVSAVDSY |
| 118-129 | 4.288500948 | 121 | RPDQVSAVDSYY |
| 118-130 | 4.788124298 | 122 | RPDQVSAVDSYYY |
| 118-132 | 5.493005611 | 123 | RPDQVSAVDSYYYDD |
| 140-150 | 4.037383416 | 124 | DTFNREPAIVR |
| 141-150 | 3.684942759 | 125 | TFNREPAIVR |
| 143-150 | 2.924719144 | 126 | NREPAIVR |
| 143-151 | 3.375334339 | 127 | NREPAIVRF |
| 144-150 | 2.575293495 | 128 | REPAIVR |
| 153-159 | 2.74066949 | 129 | SRFTEVR |
| 155-161 | 2.841713132 | 130 | FTEVREF |
| 156-161 | 2.391097937 | 131 | TEVREF |
| 157-161 | 2.081489517 | 132 | EVREF |
| 160-166 | 2.415813937 | 133 | EFAIVPL |
| 160-172 | 4.095594822 | 134 | EFAIVPLHAAPGD |
| 160-175 | 4.834451899 | 135 | EFAIVPLHAAPGDAVA |
| 160-178 | 5.928764639 | 136 | EFAIVPLHAAPGDAVAEID |
| 160-180 | 6.492908892 | 137 | EFAIVPLHAAPGDAVAEIDAL |
| 160-181 | 6.992532241 | 138 | EFAIVPLHAAPGDAVAEIDALY |
| 160-182 | 7.344972898 | 139 | EFAIVPLHAAPGDAVAEIDALYD |
| 160-183 | 7.648516884 | 140 | EFAIVPLHAAPGDAVAEIDALYDV |
| 160-184 | 8.148140234 | 141 | EFAIVPLHAAPGDAVAEIDALYDVY |
| 160-190 | 10.33084718 | 142 | EFAIVPLHAAPGDAVAEIDALYDVYLDVQEK |
| 162-178 | 5.082765067 | 143 | AIVPLHAAPGDAVAEID |
| 162-180 | 5.64690932 | 144 | AIVPLHAAPGDAVAEIDAL |
| 162-181 | 6.146532669 | 145 | AIVPLHAAPGDAVAEIDALY |
| 162-184 | 7.302140662 | 146 | AIVPLHAAPGDAVAEIDALYDVY |
| 163-181 | 5.928876124 | 147 | IVPLHAAPGDAVAEIDALY |
| 163-190 | 9.267191067 | 148 | IVPLHAAPGDAVAEIDALYDVYLDVQEK |
| 166-181 | 4.981476363 | 149 | LHAAPGDAVAEIDALY |
| 167-180 | 4.135365306 | 150 | HAAPGDAVAEIDAL |
| 167-181 | 4.634988656 | 151 | HAAPGDAVAEIDALY |
| 167-182 | 4.987429312 | 152 | HAAPGDAVAEIDALYD |

TABLE V-continued

| Peptides Identified Following Digestion with Trypsin and Chymotrypsin | | | |
|---|---|---|---|
| Position | % Mass | SEQ ID NO: | Sequence |
| 167-183 | 5.290973298 | 153 | HAAPGDAVAEIDALYDV |
| 167-184 | 5.790596648 | 154 | HAAPGDAVAEIDALYDVY |
| 167-190 | 7.973303599 | 155 | HAAPGDAVAEIDALYDVYLDVQEK |
| 173-181 | 2.955207771 | 156 | AVAEIDALY |
| 173-190 | 6.293522714 | 157 | AVAEIDALYDVYLDVQEK |
| 179-190 | 4.460352897 | 158 | ALYDVYLDVQEK |
| 180-190 | 4.242696351 | 159 | LYDVYLDVQEK |
| 181-190 | 3.896208644 | 160 | YDVYLDVQEK |
| 182-190 | 3.396585295 | 161 | DVYLDVQEK |
| 182-191 | 3.966729241 | 162 | DVYLDVQEKW |
| 184-190 | 2.740600652 | 163 | YLDVQEK |
| 185-190 | 2.240977303 | 164 | LDVQEK |
| 185-191 | 2.811121249 | 165 | LDVQEKW |
| 185-199 | 5.533190275 | 166 | LDVQEKWGLEDVMLM |
| 186-190 | 1.894489595 | 167 | DVQEK |
| 186-191 | 2.464633542 | 168 | DVQEKW |
| 191-195 | 1.897439863 | 169 | WGLED |
| 191-197 | 2.602489733 | 170 | WGLEDVM |
| 191-198 | 2.94897744 | 171 | WGLEDVML |
| 191-199 | 3.350483324 | 172 | WGLEDVMLM |
| 191-200 | 3.525196149 | 173 | WGLEDVMLMG |
| 191-208 | 6.151953511 | 174 | WGLEDVMLMGDFNAGCSY |
| 191-210 | 6.933788727 | 175 | WGLEDVMLMGDFNAGCSYVR |
| 191-218 | 9.818443147 | 176 | WGLEDVMLMGDFNAGCSYVRPSQWSSIR |
| 192-198 | 2.378833494 | 177 | GLEDVML |
| 192-199 | 2.780339378 | 178 | GLEDVMLM |
| 192-208 | 5.581809564 | 179 | GLEDVMLMGDFNAGCSY |
| 198-214 | 5.916115429 | 180 | LMGDFNAGCSYVRPSQW |
| 199-208 | 3.261246422 | 181 | MGDFNAGCSY |
| 199-210 | 4.043081638 | 182 | MGDFNAGCSYVR |
| 199-214 | 5.569627722 | 183 | MGDFNAGCSYVRPSQW |
| 199-218 | 6.927736058 | 184 | MGDFNAGCSYVRPSQWSSIR |
| 200-208 | 2.859740538 | 185 | GDFNAGCSY |
| 200-210 | 3.641575754 | 186 | GDFNAGCSYVR |
| 200-214 | 5.168121838 | 187 | GDFNAGCSYVRPSQW |

TABLE V-continued

Peptides Identified Following Digestion with Trypsin and Chymotrypsin

| Position | % Mass | SEQ ID NO: | Sequence |
|---|---|---|---|
| 200-215 | 5.434786537 | 188 | GDFNAGCSYVRPSQWS |
| 201-214 | 4.993409013 | 189 | DFNAGCSYVRPSQW |
| 203-214 | 4.190353162 | 190 | NAGCSYVRPSQW |
| 204-214 | 3.840927513 | 191 | AGCSYVRPSQW |
| 207-214 | 3.132939701 | 192 | SYVRPSQW |
| 207-218 | 4.491048037 | 193 | SYVRPSQWSSIR |
| 208-214 | 2.866275001 | 194 | YVRPSQW |
| 209-214 | 2.366651651 | 195 | VRPSQW |
| 209-218 | 3.724759988 | 196 | VRPSQWSSIR |
| 211-218 | 2.942924771 | 197 | PSQWSSIR |
| 213-218 | 2.378892004 | 198 | QWSSIR |
| 215-220 | 2.333010341 | 199 | SSIRLW |
| 219-224 | 2.158151613 | 200 | LWTSPT |
| 219-225 | 2.608766808 | 201 | LWTSPTF |
| 219-226 | 3.001136178 | 202 | LWTSPTFQ |
| 219-227 | 3.571280124 | 203 | LWTSPTFQW |
| 219-228 | 3.917767831 | 204 | LWTSPTFQWL |
| 219-231 | 4.914064263 | 205 | LWTSPTFQWLIPD |
| 219-234 | 5.750826164 | 206 | LWTSPTFQWLIPDSAD |
| 219-241 | 7.924230704 | 207 | LWTSPTFQWLIPDSADTTATPTH |
| 219-244 | 8.957129041 | 208 | LWTSPTFQWLIPDSADTTATPTHCAY |
| 219-246 | 9.787860928 | 209 | LWTSPTFQWLIPDSADTTATPTHCAYDR |
| 220-246 | 9.441373221 | 210 | WTSPTFQWLIPDSADTTATPTHCAYDR |
| 221-226 | 2.084504524 | 211 | TSPTFQ |
| 221-227 | 2.654648471 | 212 | TSPTFQW |
| 221-228 | 3.001136178 | 213 | TSPTFQWL |
| 221-241 | 7.007599051 | 214 | TSPTFQWLIPDSADTTATPTH |
| 221-244 | 8.040497388 | 215 | TSPTFQWLIPDSADTTATPTHCAY |
| 221-246 | 8.871229275 | 216 | TSPTFQWLIPDSADTTATPTHCAYDR |
| 225-246 | 7.687979666 | 217 | FQWLIPDSADTTATPTHCAYDR |
| 226-244 | 6.406632585 | 218 | QWLIPDSADTTATPTHCAY |
| 226-246 | 7.237364471 | 219 | QWLIPDSADTTATPTHCAYDR |
| 228-246 | 6.274851155 | 220 | LIPDSADTTATPTHCAYDR |

TABLE V-continued

Peptides Identified Following Digestion with Trypsin and Chymotrypsin

| Position | % Mass | SEQ ID NO: | Sequence |
|---|---|---|---|
| 229-244 | 5.097631562 | 221 | IPDSADTTATPTHCAY |
| 229-246 | 5.928363448 | 222 | IPDSADTTATPTHCAYDR |
| 232-246 | 4.932067017 | 223 | SADTTATPTHCAYDR |
| 234-246 | 4.447745772 | 224 | DTTATPTHCAYDR |
| 235-244 | 3.264573229 | 225 | TTATPTHCAY |
| 236-246 | 3.785696695 | 226 | TATPTHCAYDR |
| 239-246 | 2.948823309 | 227 | PTHCAYDR |
| 245-250 | 2.060234463 | 228 | DRIVVA |
| 245-252 | 2.636453171 | 229 | DRIVVAGM |
| 245-253 | 2.982940878 | 230 | DRIVVAGML |
| 245-254 | 3.329428586 | 231 | DRIVVAGMLL |
| 245-255 | 3.807719815 | 232 | DRIVVAGMLLR |
| 247-253 | 2.152208992 | 233 | IVVAGML |
| 247-254 | 2.498696699 | 234 | IVVAGMLL |
| 247-255 | 2.976987929 | 235 | IVVAGMLLR |
| 247-256 | 3.151700754 | 236 | IVVAGMLLRG |
| 248-255 | 2.630500222 | 237 | VVAGMLLR |
| 249-255 | 2.326956236 | 238 | VAGMLLR |
| 250-255 | 2.023412249 | 239 | AGMLLR |
| 252-259 | 2.630500222 | 240 | MLLRGAVV |
| 254-266 | 4.11110757 | 241 | LRGAVVPDSALPF |
| 255-266 | 3.764619863 | 242 | RGAVVPDSALPF |
| 256-262 | 1.974201118 | 243 | GAVVPDS |
| 256-263 | 2.191857663 | 244 | GAVVPDSA |
| 256-264 | 2.53834537 | 245 | GAVVPDSAL |
| 256-265 | 2.835713438 | 246 | GAVVPDSALP |
| 256-268 | 4.086369477 | 247 | GAVVPDSALPFNF |
| 256-271 | 4.914051937 | 248 | GAVVPDSALPFNFQAA |
| 256-272 | 5.413675286 | 249 | GAVVPDSALPFNFQAAY |
| 256-273 | 5.588388111 | 250 | GAVVPDSALPFNFQAAYG |
| 256-274 | 5.934875818 | 251 | GAVVPDSALPFNFQAAYGL |
| 256-276 | 6.553981174 | 252 | GAVVPDSALPFNFQAAYGLSD |
| 256-293 | 12.44599823 | 253 | GAVVPDSALPFNFQAAYGLSDQLAQAISDHYPVEVMLK |
| 267-272 | 2.185617005 | 254 | NFQAAY |
| 267-273 | 2.360329829 | 255 | NFQAAYG |
| 267-286 | 6.777625088 | 256 | NFQAAYGLSDQLAQAISDHY |

TABLE V-continued

| Peptides Identified Following Digestion with Trypsin and Chymotrypsin | | | |
|---|---|---|---|
| Position | % Mass | SEQ ID NO: | Sequence |
| 267-293 | 9.217939951 | 257 | NFQAAYGLSDQLAQAISDHYPVEVMLK |
| 268-293 | 8.868514302 | 258 | FQAAYGLSDQLAQAISDHYPVEVMLK |
| 269-293 | 8.417899107 | 259 | QAAYGLSDQLAQAISDHYPVEVMLK |
| 270-293 | 8.025529737 | 260 | AAYGLSDQLAQAISDHYPVEVMLK |
| 271-293 | 7.807873192 | 261 | AYGLSDQLAQAISDHYPVEVMLK |
| 273-280 | 2.547459231 | 262 | GLSDQLAQ |
| 273-282 | 3.111603483 | 263 | GLSDQLAQAI |
| 273-285 | 4.150655085 | 264 | GLSDQLAQAISDH |
| 273-289 | 5.646574866 | 265 | GLSDQLAQAISDHYPVE |
| 273-290 | 5.950118852 | 266 | GLSDQLAQAISDHYPVEV |
| 273-291 | 6.351624736 | 267 | GLSDQLAQAISDHYPVEVM |
| 273-292 | 6.698112443 | 268 | GLSDQLAQAISDHYPVEVML |
| 273-293 | 7.090593298 | 269 | GLSDQLAQAISDHYPVEVMLK |
| 275-293 | 6.569392766 | 270 | SDQLAQAISDHYPVEVMLK |
| 277-293 | 5.95028741 | 271 | QLAQAISDHYPVEVMLK |
| 279-293 | 5.211430333 | 272 | AQAISDHYPVEVMLK |
| 281-293 | 4.601404418 | 273 | AISDHYPVEVMLK |
| 283-293 | 4.037260166 | 274 | SDHYPVEVMLK |
| 285-293 | 3.41815481 | 275 | HYPVEVMLK |
| 287-293 | 2.498585215 | 276 | PVEVMLK |

TABLE Va

| Peptides Identified Following Digestion with Trypsin and PNGaseA | | |
|---|---|---|
| Position | SEQ ID NO: | Sequence |
| 4-16 | 278 | IAAFNIQTFGETK |
| 17-32 | 279 | MSNATLVSYIVQILSR |
| 33-42 | 280 | YDIALVQEVR |
| 43-51 | 281 | DSHLTAVGK |
| 52-74 | 282 | LLDNLNQDAPDTYHYVVSEPLGR |
| 52-78 | 283 | LLDNLNQDAPDTYHYVVSEPLGRNSYK |
| 81-112 | 284 | YLFVYRPDQVSAVDSYYYDDGCEPCGNDTFNR |
| 81-118 | 285 | YLFVYRPDQVSAVDSYYYDDGCEPCGNDTFNREPAIVR |

TABLE Va-continued

| Peptides Identified Following Digestion with Trypsin and PNGaseA | | |
|---|---|---|
| Position | SEQ ID NO: | Sequence |
| 113-118 | 286 | EPAIVR |
| 119-122 | 287 | FFSR |
| 123-127 | 288 | FTEVR |
| 128-158 | 289 | EFAIVPLHAAPGDAVAEIDALYDVYLDVQEK |
| 215-223 | 290 | IVVAGMLLR |
| 224-261 | 291 | GAVVPDSALPFNFQAAYGLSDQLAQAISDHYPVEVMLK |

Free Sulfhydryl Content (Ellman's Method)

Quantitative assay of the free-thiols indicated that both phr DNase I protein and Pulmozyme® lack free sulfhydryls, while the positive control detected four free sulfhydryls (thiols) as expected. These results confirm that in phr DNase I four Cysteine amino acids are bound in 2 disulfide bonds (Cys 102-Cys 105 and Cys 174-Cys210) as was suggested for DNase-1 and Pulmozyme®.

Glycan Analysis:

Preliminary analysis was performed to characterize the various glycan structures of prhDNase I produced from BY2 cell culture. FIGS. 8A-8C show NP-HPLC profile of glycans derived from three separate batches of prhDNase I using PNGase A to release the glycans. Release of glycans by PNGase F indicated a low abundance of glycans without core fucose structures in prhDNase I. The glycan profile of all three batches of prhDNase I indicated a similar profile. Peaks in the profiles shown in FIG. 8A correlate to the detailed structures in FIG. 8B indicating the relative amounts of glycans released from the batches of prhDNase I.

The glycan analysis of recombinant human DNAseI protein product from the transformed tobacco cells revealed a glycan profile comprising two main glycan peaks consisting of at least four glycan structures (e.g. peaks 3+4 and 5). Predominant glycan structures representing a high percentage of the glycan profile (over 80%) contain mannose 3-β-(1,2) xylose-α-(1,3) fucose [Fc(3)M3X] and/or mannose 4-α-(1,2) xylose (M4X) with an additional one or two N-acetylglucosamine substitution on the outer mannose sugars (FIG. 8B). The other glycans contain smaller structures missing either fucose or N-acetylglucosamine substitutions (3-6%) or hybrid structures (up to 14%).

FIG. 8C shows a comparison of glycans found in prhDNase I released by PNGase A compared to glycans released from Pulmozyme® by PNGase F. The wide variations in glycosylation pattern found in Pulmozyme® are due to the abundance of bi- and tri-antennary glycans with additional sialic acid residues attached, leading to a mixture of charged and uncharged glycan moieties. Clearly, phr DNase I glycosylation is more homogeneous and does not include charged glycans.

Purity of Plant-Expressed Rh DNase Preparation:

FIGS. 9A-9D represent a typical chromatogram of the plant-expressed prh DNase I, analyzed by RP-HPLC at 214 nm (9A, 9B) and at 280 nm (9C, 9D), after subtraction of start-of-sequence blank. Insets 9B and 9D are expanded views of the prh DNase I peak. In both chromatograms, the prh DNase I resolves as a main peak (>93.6% purity) with a retention time of 28.3 minutes and an additional two small peaks, a pattern characteristic of all batches of the prh DNase I tested.

Thus, the prh DNase I preparation is characterized by molecular weight, pI, free sulfhydryl content, immune cross-reactivity and amino acid sequence comparable to but distinct from that of commercially available mammalian cell expressed DNase I, and consistent with the translation product of the expressed human DNase I coding sequence of SEQ ID NO: 9. Further, the plant-expressed rh DNase I is secreted into the medium of cells in suspension culture, and can be purified to a high degree of purity, containing less than 7% impurities detected by HPLC at both 214 and 280 nm.

Example 3

Biological Activity of Plant-Expressed rh DNase I

Biological activity of the plant-expressed rh DNase I was assayed using several assays, and compared to that of the mammalian-cell expressed commercially available human recombinant enzyme Pulmozyme® (Genentech, Mass.).

Methods:

DNA-Methyl Green Assay

Deoxyribonuclease I (DNase I) is an endonuclease that cleaves DNA preferentially at phosphodiester linkages, yielding 5'-phosphate-terminated polynucleotides with a free hydroxyl group on position 3', on average producing tetranucleotides.

Activity of DNase I was assessed by the Methyl Green enzymatic activity assay, employing DNA from Salmon Testis (Sigma cat No. D1626) complexed with the dye methyl green (Sigma cat No. M8884) as a substrate. Methyl green intercalates between the stacked bases of double-stranded DNA. Once the long DNA molecules are hydrolyzed into tetranucleotides as a result of DNase1 activity, dissociation of methyl green from the DNA occurs, the free methyl green decolorizing in a second, nonenzymatic reaction. The spontaneous decolorization of free methyl green at neutral pH is likely to result from tautomerization of the dye.

Standard curves were prepared by dilution of purified standard phrDNase I in activity Buffer (25 mM HEPES-NaOH, 4 mM $CaCl_2$, 4 mM $MgCl_2$, 0.1% BSA, 0.05% Tween-20, pH 7.5) at concentrations ranging from 0.3 to 20 ng/ml at 2-fold series dilutions. Samples and controls were prepared in a similar matter. One hundred microliters of standards, controls and samples was added in duplicates to a 96-well plate (NUNC) containing 100 μl of DNA-methyl green substrate and the contents were mixed thoroughly. The plates were then sealed and agitated for 30 min at room temperature, to then incubated overnight at 37° C. and absorbance measured at 620 nm. Absorbance was plotted versus standards concentrations and the data were fit to a 4-parameter logistic model by the nonlinear regression method of Marquardt.

DNase I activity in different expression systems was expressed as percent of the activity measured in the apoplast targeted cells (100%) (see FIG. 2).

Enzyme-Linked Immunosorbent Assay (ELISA)

Enzyme-linked immunosorbent assay (ELISA) was used to detect the presence of immunoreactive rh Dnase I in a sample. Two different ELISA methods were performed. The first ELISA assay (ELISA 1) was developed using antibodies acquired against Pulmozyme®. The second ELISA assay (ELISA 2) was developed using antibodies acquired against plant derived DNase I.

The total content of prh DNase I was assessed by indirect sandwich ELISA assays. The antibodies used in ELISA 1 include unfractionated rabbit anti-human DNase I antiserum and chicken yolk IgY fraction. These antibodies were prepared following immunization of rabbits and chickens with commercially available, mammalian cell expressed human DNase I (Pulmozyme®). Unfractionated rabbit anti-human DNase I antiserum was prepared in accordance with a standard polyclonal antibody preparation protocol including four immunizations with 3 mg antigen per rabbit, and collection of the serum after the fourth immunization. Anti-human DNase I yolk IgY fraction was prepared in accordance to a standard polyclonal antibody preparation protocol including four immunizations with 2.5 mg antigen per chicken, and collection of the yolks after the fourth immunization.

The antibodies used in ELISA 2 included rabbit anti-prh DNase I and goat-anti-prh DNase I. These antibodies were prepared by immunization of rabbits and goats with prh DNase and affinity purification on a Pulmozyme® column. Thus, the purified antibodies detect/bind the common backbone sequence of Pulmozyme® and prh DNase I. The antibodies were prepared by GenScript USA Inc in accordance to GenScript standard polyclonal antibody preparation protocol including four immunizations with 3 mg antigen per rabbit and 8 mg antigen per goat, and collection of the serum after the forth immunization.

Microtiter 96-well plates (Costar cat No. 9018 for ELISA 1 and NUNC cat No. 442404 for ELISA 2) were incubated for overnight at 4° C. with 100 μl/well of whole rabbit antiserum 2500-fold diluted (ELISA 1) or 1 ug/ml goat anti-prh DNase I antibody (ELISA 2) and diluted in carbonate-bicarbonate buffer pH 9.6 (Sigma cat No. C3041).

Plates were then washed four times with wash buffer prepared according to manufacturer's instructions (KPL cat No. 50-63-00), blocked with 300 μl of Blocker Casein™ (Pierce cat No. 37528), incubated for one hour at 25° C. and washed again four times with wash buffer. A standard curve was prepared by dilution of standard prh DNase I in dilution buffer (1% (w/v) BSA in phosphate buffered saline) at concentrations ranging from 0.3125 to 20 ng/ml (ELISA 1) or 0.1562 to 10 ng/ml (ELISA 2) at 2-fold series dilutions. Similarly, samples and controls were diluted 100- to 100,000-fold in dilution buffer. One hundred microliters of standards, controls and samples were added in duplicates to the wells of pre-coated and pre-blocked plates, and agitated for two hours at 25° C. or incubated overnight at 4° C. Plates were then washed 4 times and incubated for 1.5 hours at 25° C. with 100 μl/well of chicken yolk IgY fraction diluted 20,000-fold in the dilution buffer (ELISA 1) or rabbit anti-prh DNase I antibody diluted 10,000-fold in the dilution buffer. Following four additional washing steps, 100 μl of donkey anti-chicken HRP conjugated antibody (Jackson ImmunoResearch Laboratories, Inc., PA; cat No. 703-035-155) (ELISA 1) or donkey anti-rabbit HRP conjugated antibody (Jackson ImmunoResearch Laboratories, Inc., PA; cat No. 711-035-152) (ELISA 2), diluted 5000-fold in dilution buffer, was added and plates were incubated for one hour at 25° C. Next, plates were washed extensively and supplemented with 100 μl TMB solution (Millipore; cat No. ES001). Upon color development reaction was stopped by addition of 100 μl of 10% (v/v) HCl and then read at 450 nm.

Absorbance was plotted versus the standards concentrations and data were fit to a 4-parameter logistic model by the nonlinear regression method of Marquardt.

DNase I immunoreactivity in different expression systems was expressed as percent of the activity measured in the apoplast targeted cells (100%) (see FIG. 2).

Enzyme Kinetics:

The kinetics of an enzymatic reaction are typically studied by varying the concentration of substrate and plotting the rate of product formation as a function of substrate concentration (velocity). In the conventional case, this yields a typical hyperbolic Michaelis-Menten curve and a linear reciprocal Lineweaver-Burk plot, from which the kinetic constants of the enzyme can be calculated. For enzyme reactions exhibiting simple Michaelis-Menten kinetics, the Michaelis constant ($K_M$), or the substrate concentration at half maximum velocity ($V_{max}/2$) represents the dissociation constant of the enzyme-substrate (ES) complex or the affinity for substrate. Low $K_M$ values indicate higher substrate affinity.

The kinetic constant ($k_2$), often called $k_{cat}$, represents the number of substrate molecules converted into product per unit time at a single catalytic site when the enzyme is fully saturated with substrate. $k_{cat}$ is usually the reaction rate limiting step and is calculated by dividing $V_{max}$ by the enzyme's concentration. $k_{cat}/K_m$ is often thought of as a measure of enzyme efficiency.

Many enzymes do not behave in a conventional way, their velocity curves rising to a maximum and then declining as the substrate concentration rises, referred to as substrate inhibition, and thought to be the result of binding of more than one substrate molecule to an active site. Substrate inhibition is considered a biologically relevant regulatory mechanism although it is often observed when using artificially high substrate concentrations, in a laboratory setting.

Kinetic plots for substrate inhibition represent variation of initial velocity as a function of substrate concentration or as double-reciprocal plot of the variation of initial velocity with substrate concentration. Since the same compound acts at the same time as both substrate and inhibitor the double reciprocal plot does not yield a straight line. it may be assumed that inhibitory effect is negligible at low substrate concentration and from an asymptote to the curve in this region $K_m$ and $V_{max}$ can be estimated.

Assays of the enzyme kinetics of DNase I activity were performed using the DNaseAlert™ (custom made by IDT) fluorescence-quenched oligonucleotide probe, which has a HEX™ reporter dye (hexachlorofluorescein) on one end and a dark quencher on the other end, and which emits a detectable fluorescent signal upon nuclease degradation. The DNA sequence has been carefully optimized to react with a wide variety of nucleases; it contains domains that will react with single-stranded endonucleases, certain single-stranded exonucleases, and double-stranded nucleases.

The intact substrate has little or no fluorescence, but when cleaved by a DNase, the hydrolyzed substrate fluoresces pink (536 nm or UV excitation, 556 nm emission) when cleaved, and can be detected visually or using a fluorometer. Plots of DNase I initial velocity versus substrate concentration display a velocity curve that rises to a maximum and then declines as the substrate concentration increases (FIG. 10A). This pattern can characterize a typical substrate inhibition behavior. The double reciprocal plot allows the extraction of $K_M$ and $V_{max}$ values by abscissa intercept with an asymptote to the high substrate region (approaching the origin), where the inhibitory effect predominates (FIG. 10B).

DNaseAlert™ Based Kinetic Assay

DNaseAlert™ substrate (IDT; custom made) was diluted in Activity Buffer (25 mM HEPES-NaOH, 4 mM $CaCl_2$, 4 mM $MgCl_2$, 0.1% BSA, 0.05% Tween-20, pH 7.5) at concentrations ranging from 1 to 40 μM. Ten microliters of substrate was divided in duplicates into a black 96-well plate (Greiner cat No. 655900) and the reaction was initiated by rapid addition of 10 ul DNase I to a final concentration of 50 ng/mL. The plate was immediately incubated in a fluorometer and real-time data was collected (535 nm excitation, 565 nm emission) at 30 seconds intervals for 3 minutes.

Initial velocities were extracted by using fluorescent product standard curve.

Product standard curve was prepared by dilution of 6-HEX (AnaSpec) in activity buffer at concentrations ranging from 7 to 250 nM at 1.67-fold series dilutions.

Fluorescence units were transformed to concentration values (μM) by applying the calibration curve formula (y=ax+b when y=FU and a=nM). A double reciprocal plot of initial velocity versus substrate concentration (at 2-15 μM) allows the extraction of $K_M$ and $V_{max}$ values by abscissa intercept with an asymptote to the high substrate region (FIG. 10B).

Specific Activity

Specific activity of human DNase I was evaluated using the DNaseAlert™ fluorescence-quenched oligonucleotide probe (supplied by Ambion, cat #AM1970, manufactured by IDT) that emits a fluorescent signal upon nuclease degradation. One unit (U) of DNase is defined as the amount of enzyme that releases 1 μmol of fluorescent product per minute at 22° C. The value of specific activity (U/mg) is calculated by dividing the value of total activity (U) by the amount of enzyme used in the reaction. Enzyme concentration was determined by absorbance at 280 nm, based on to extinction coefficient. The calculated extinction coefficient of phr DNase I is 1.45 g/L.

2 nmol of DNaseAlert™ substrate (Ambion, cat #AM1970) was resuspended with 1 mL nuclease free water. Prh DNase I and Pulmozyme® samples were diluted 10,000-40,000-fold in activity buffer (25 mM HEPES-NaOH, 4 mM $CaCl_2$, 4 mM $MgCl_2$, 0.1% BSA, 0.05% Tween-20, pH 7.5). 80 uL of activity buffer was divided in duplicates to a black 96-well plate (Greiner cat No. 655900). Ten microliters of substrate was then added and the reaction was initiated by rapid addition of 10 ul Rh DNase I or Pulmozyme®. The plate was immediately incubated in a fluorometer and real-time data was collected (535 nm excitation, 565 nm emission) at 30-second intervals for 3 minutes. Product standard curve was prepared by dilution of 6-HEX (AnaSpec cat #81019) in activity buffer at concentrations ranging from 7 to 250 nM at 1.67-fold series dilutions. Fluorescence units were transformed to concentration values (μM) by applying the calibration curve formula (y=ax+b when y=FU and a=nM). 1 U is defined as the amount of enzyme that releases 1 μmol of fluorescent product per minute at 22° C. The value of specific activity (U/mg) was calculated by dividing the value of total activity (U) by the amount of enzyme used in the reaction.

Results:

Plant Expressed rh DNase I has Superior Enzyme Kinetics Compared to Mammalian Cell Expressed Human DNase I FIG. 10A shows representative substrate inhibition kinetic plots of plant expressed rh DNase I and Pulmozyme®. Initial velocity versus substrate concentration plots yielded a curve that is typical for a substrate inhibition pattern (see Table VI) for both enzymes. The $K_M$, and $V_{max}$ values were calculated from asymptote equation plotted in a region of low substrate concentrations (2-15 μM) in double reciprocal plots (FIG. 10B). $k_{cat}$ values of phr DNase I and Pulmozyme® were calculated by dividing $V_{max}$ with enzyme's concentration (Table VI), further indicating that prh DNase I and Pulmozyme® enzyme kinetics exhibit characteristics of the substrate inhibition kinetic model.

However, it is evident that although both enzymes comprise the same DNase I amino acid sequence, prh DNase I exhibits improved kinetic properties (greater substrate affinity and greater enzyme velocity) compared to Pulmozyme®. Without wishing to adhere to a single hypothesis, this may be due to unique post-translational modifications to of the plant-expressed rh DNase I generated as a result of expression of the nucleic acid construct of the present invention in plant, rather than mammalian expression systems.

Three batches of DNase extracted from cultured cells were analyzed and have shown similar characteristics. Further analysis of batches of DNase extracted from cells sampled from different lines of transformed BY2 cells at different times confirmed the reproducible, favorable kinetic characteristics of the plant expressed rh DNase as compared to Pulmozyme®.

TABLE VI

Kinetic parameters of plant expressed rh DNase I vs. Pulmozyme ®

| DNase I | $K_M$ (μM) | $V_{max}$ (μM/min) | $k_{cat}$ ($sec^{-1}$) | $k_{cat}/K_M$ ($sec^{-1}μM^{-1}$) |
|---|---|---|---|---|
| Plant-expressed rh DNase I | 24.3 | 0.58 | 6.24 | 0.26 |
| Pulmozyme ® | 60.9 | 0.44 | 4.76 | 0.08 |

TABLE VIa

Kinetic parameters of 3 plant expressed rh DNase I batches

| prhDNase I line | $K_M$ (μM) | $V_{max}$ (μM/min) | $k_{cat}$ ($sec^{-1}$) | $k_{cat}/K_M$ ($sec^{-1}μM^{-1}$) |
|---|---|---|---|---|
| 1 | 16.77 | 0.37 | 5.58 | 0.33 |
| 2 | 12.54 | 0.36 | 5.44 | 0.43 |
| 2 | 12.07 | 0.35 | 5.29 | 0.44 |

Specific Activity of Plant-Expressed Rh DNase I

Specific activity values of plant-expressed rh DNase I and mammalian cell expressed DNase I (Pulmozyme®) are presented in Table VII. Significantly, the specific activity of plant-expressed rh DNase I, as assayed with the DNase-Alert™ fluorescence-quenched oligonucleotide probe is about 3-fold higher than that of the Pulmozyme®.

This difference in plant-expressed rh DNase I and Pulmozyme® specific activity reflects the improved kinetic properties of plant-expressed rh DNase I compared to Pulmozyme® (see FIGS. 10A and 10B and Table VI above).

TABLE VII

Specific activity of plant-expressed rh DNase I vs. Pulmozyme

| DNase I | Specific activity (U/mg) |
|---|---|
| Plant-expressed rh DNase I | 0.258 ± 0.055 |
| Pulmozyme ® | 0.091 ± 0.018 |

Thus, plant-expressed prh DNase I is fully active catalytically, towards conventional DNase I substrates, exhibits significantly superior enzyme kinetics, and possesses a higher specific activity, consistent with the improved enzyme kinetics, when compared to that of the commercially available, clinical standard mammalian cell to expressed recombinant DNase I.

Example 4

Superior Resistance of Plant-Expressed Rh Dnase I to Actin Inhibition

Analysis of the composition of CF sputum reveals large quantities (3 to 14 mg/ml) of DNA and actin (0.06 to 5 mg/ml) released by necrosing neutrophils after their recruitment into the airways during response to infection. In addition to hydrolysis of deoxynucleic acid, DNase I can depolymerize filamentous actin (F-actin).

Monomeric globular actin (G-actin) is a potent inhibitor (Ki 1 nM) of DNase I enzymatic activity, potentially influencing the effectiveness of inhaled DNase I in CF lungs.

To evaluate G-actin inhibitory effect on DNase I activity, an $IC_{50}$ assay (half maximal inhibitory concentration) was developed, applying Methyl Green enzymatic activity assay in the presence of elevated concentrations of human non-muscle actin (Cytoskeleton; cat No. APHL99).

One hundred microliters of actin/DNase-I mixture was divided in duplicates to a 96-well plate (NUNC cat No. 442404) containing 100 ul of DNA-methyl green substrate.

Human non-muscle actin (Cytoskeleton; cat No. APHL99) was diluted in activity buffer (25 mM HEPES-NaOH, 4 mM $CaCl_2$, 4 mM $MgCl_2$, 0.1% BSA, 0.05% Tween-20, pH 7.5) containing 0.1 mM ATP (Sigma cat No. A26209) to reach concentrations ranging from 100 to 0.1 ug/mL, at 2-fold series dilutions. Prh DNase I and Pulmozyme® (control) were diluted to reach concentration of 100 ng/mL. Each plate's content was then mixed thoroughly, plates were read at 620 nm, sealed and incubated for 4 hr at 37° C. and read again (620 nm). The change in absorbance was plotted versus actin concentrations and $IC_{50}$ parameters were calculated by non-linear fit using GraFit software (Erithacus Software, UK).

Results: Plant Expressed rh DNase I Exhibits Improved Resistance to Actin Inhibition FIG. 11 shows plots describing plant expressed rh DNase I and Pulmozyme® catalytic activity (expressed as $\Delta OD_{620nm}$) in the presence of increasing concentrations of human G-actin. The plot of the change in absorbance versus actin concentration yields hyperbolic curves allowing the extraction of $IC_{50}$ (Table VIII, below). Although both enzymes have the same amino acid sequence, the plant expressed rh DNase I displays greater resistance to inhibition by human actin than that of the commercial, mammalian cell expressed DNase (Pulmozyme®). Three batches of DNase extracted from cultured cells were analyzed and have shown similar characteristics. Yet further, comparison of resistance/susceptibility to actin inhibition of the plant expressed rhDNase I sampled from different lines of transformed BY2 cells expressing the recombinant enzyme (see Table VIIIa below) confirmed the reproducible improved resistance to actin inhibition.

Without wishing to be limited to a single hypothesis, one explanation for this increased resistance to actin inhibition could be the result of the improved affinity of the plant expressed enzyme for its DNA substrate, as compared to that of the mammalian expressed enzyme, or actual reduced affinity of the prhDNase I for actin monomers, or both.

TABLE VIII

| IC$_{50}$ of plant expressed rh DNase I vs. Pulmozyme ® | |
|---|---|
| DNase I | IC$_{50}$ (μg/ml) |
| Prh DNase I | 1.8191 ± 0.1003 |
| Pulmozyme ® | 0.6870 ± 0.0204 |

TABLE VIIIa

| IC$_{50}$ of plant expressed rh DNase I vs. Pulmozyme ® | |
|---|---|
| DNase I | IC$_{50}$ (μg/ml) |
| Prh DNase I batch 1 | 1.7067 ± 0.0568 |
| Prh DNase I batch 2 | 1.8453 ± 0.0429 |
| Pulmozyme ® | 0.5458 ± 0.0115 |

Example 5

Effect of rh DNase I on the Rheological Properties of Sputum

Mucus is defined as the heterogeneous, adhesive, viscoelastic gel produced by goblet cells and submucosal glands. At the chemical level, mucus is an integrated structure of biopolymers. Its physical behavior is complex (non-Newtonian), with highly variable properties that are between those of a viscous liquid and an elastic solid.

Characterization of the physical properties of mucus largely focuses on two properties: (i) viscous modulus, also termed loss modulus (G", expressed in pascal-seconds-Pa·s), which is the extent to which the gel resists the tendency to flow, and (ii) elastic modulus, also termed storage modulus (G', expressed in pascals-seconds-Pa·s), which expresses the tendency for the gel to recover its original shape following stress-induced deformation. Together, these properties describe the rheology of complex biological fluids. The phase angle or loss tangent value δ, calculated from the inverse tangent of G"/G' (tan $-\delta_G$=G"/G') is also a common parameter for characterizing mucus, reflecting the overall elastic or viscous nature of the sample and used to quantify the extent of elastic behaviour of material. A phase angle close to zero indicates strongly elastic behaviour, as opposed to 90°, which indicates purely viscous behaviour. A phase angle of 45° is considered the "cross over" value between G" and G'.

CF Sputum Collection, Storage and Sample Treatment

CF sputum samples were collected from patients with severe lung disease attending the Cystic Fibrosis Centers. Sputum was directly expectorated into a sterile hermetically sealed container and transported on ice to laboratories equipped for rheological characterization. Saliva was removed and each sputum sample was homogenized gently and divided into 200-300 mg aliquots and stored at −70° C. until analyzed. Frozen samples were thawed at room temperature before analysis, as freezing of the sputum samples followed by a single thawing step was shown to afford accurate and reproducible analysis of sputum rheology, similar to those of the fresh sample before freezing.

In order to ensure that the sputum is free of exogenous DNase I activity (e.g. Pulmozyme®), sputum samples were collected 12-24 hours after treatment with Pulmozyme® aerosol, as it has been reported that inhaled aerosol DNase I is cleared from the sputum from patients as soon as two hours.

Study Design

Each sputum aliquot was incubated for 30 min at 37° C. with DNase I formulation buffer (1 mM $CaCl_2$, 150 mM NaCl, pH 6.1-6.5) containing either prh to DNase I or Pulmozyme® (final concentration 0.2, 2, 5, 10 and 20 ug/gr sputum). Control samples were treated with DNase I formulation buffer only.

Four percent (vol/wt) of drug or control were added to the sputum sample.

Following incubation, rheological properties of sputum samples were immediately measured.

Sputum Rheology Assay

Rheological properties of the sputum samples were determined using a controlled stress rheometer (HAAKE RheoStress 1, Thermo Fisher Scientific GmbH, Karlsruhe, Germany). The measurements were conducted at 20° C. using two techniques: a time-sweep (FIGS. 12A-12D and 13A-13D) and a stress sweep (FIGS. 18A-18D and 19A-19D).

Time sweep measurements were performed using a 35 mm cone plate set-up. The angle between the cone and the plate was 0.5° and the sample volume required was 150 ul. Nondestructive oscillatory stress was applied to the sample and the elastic (G') and viscous (G") modulus were recorded versus time. To avoid disruption of the weak biopolymer network in the sputum due to the oscillation forces, the measurements were performed in the linear viscoelastic region at a constant frequency of 1 Hz with a stress of 0.10 Pascals (Pa).

Stress sweep measurements were performed using 20 mm sandblasted parallel plate geometry. The sputum samples (200 ul) were loaded onto the rheometer with a gap width of 0.5 mm A stress sweep was performed from 0.1 to 100 Pa at a constant frequency of 1 Hz and the elastic modulus, (G'), viscous modulus (G") and phase angle (δ) were measured. The applied stress in which G' and G" cross over (or phase angle reaches 45°) is the stress in which the sample begins to act more liquid-like than solid-like. At this point stress values were recorded and compared between DNase I treated and untreated samples.

Rheological parameters were determined using RheoWin 4 (HAAKE, Thermo Fisher Scientific GmbH, Karlsruhe, Germany). Before measurements, sputum samples were loaded into the rheometer plate and equilibrated for 30 seconds to allow relaxation to the original gel structure. In order to slow down the dehydration of the sputum, a solvent trap was used. Experiments were performed on at least two sputum fractions taken from each sputum sample and the data were averaged.

Measurements of Total DNA Content in Sputum

Sputum DNA content was determined by the modified aminobenzoic acid (DABA) assay. Salmon sperm DNA (Sigma #D1626, ~2 mg/mL) and sputum samples (~100 mg) were diluted 10-fold in a dilution buffer (25 mM HEPES-NaOH, 4 mM $CaCl_2$, 4 mM $MgCl_2$, 0.1% BSA, 0.05% Tween-20, pH 7.5) and incubated at 60° C. for 1 hour.

Samples were repeatedly vortexed to allow sputum disintegration. DNA concentration of the diluted salmon sperm sample was then measured (NanoDrop 2000, Thermo Fisher Scientific) and standard curve was prepared by dilution of the salmon sperm sample in the dilution buffer at concentrations ranging from 3.13 to 200 μg/ml at 2-fold series dilutions. Similarly, sputum samples were further diluted at 2-fold series dilution up to 1280-fold. Next, fifty microliters of standards and samples was added in duplicates to a black 96-well plate (Greiner cat No. 655900) and incubated with 50 μL of 20% 3,5-diaminobenzoic acid (TCI Europe cat No. D0079) at 60° C. for 1 hour. Fifty (50) ul of 5N HCl was then added to stop the reaction and fluorescence was measured by fluorometer (390 nm excitation/530 nm emission). Fluorescence units were plotted versus standard DNA concentrations and the data were fit to a 4-parameter logistic model by the nonlinear regression method of Marquardt. DNA concentration in sputum was then interpolated.

Magnesium Chloride and Rh DNase I Effect on Rheological Properties of Sputum

Magnesium ion is a cofactor of DNase I, hence promoting DNA hydrolysis.

Studies suggest that increasing magnesium concentration in the airway surface liquid by aerosolization of magnesium solutions or oral magnesium supplements could improve the removal of highly viscous mucus in chronic lung disease by improving DNase activity. Furthermore, it was suggested that magnesium indirectly triggers the activity of rhDNase I in CF sputum by promoting polymerization of G-actin into F-actin, hence, reducing inhibition of DNase-I by G-actin. Consequently, magnesium supplement may overcome poor response to rhDNase treatment in non-responding CF patients exhibiting low levels of magnesium in their sputum.

Magnesium Sulfate and rh DNase I Effect on Catalytic Activity of rh DNase I

Several trials conducted with inhaled magnesium sulfate in patients with acute asthma have shown that magnesium sulfate inhalation is tolerable. Magnesium ions, required for DNase I activity, can therefore be supplemented to rh DNase I formulation as magnesium sulfate. To verify that magnesium sulfate does not produce an inhibitory effect on rh DNase I activity a methyl green activity assay was applied in the presence of elevated concentrations of magnesium sulfate and compared to magnesium chloride effect.

One hundred microliters of plant expressed rh DNase I was divided in duplicates to a 96-well plate (NUNC cat No. 442404) containing 100 ul of DNA-methyl green substrate to reach concentration of 100 ng/mL. Reaction was prepared in a modified activity buffer (25 mM HEPES-NaOH, 4 mM $CaCl_2$, 0.1% BSA, 0.05% Tween-20, pH 7.5) containing elevated concentration of magnesium sulfate or magnesium chloride (0.5-100 mM). The plate's contents were then mixed thoroughly, and the plates were read at 620 nm, sealed and incubated for 3 hr at 37° C. and re-read (620 nm). Change in absorbance was plotted versus concentrations of magnesium sulfate or magnesium chloride added.

Results:

Plant Expressed rh DNase I is Highly Effective in Reducing Rheological Properties of Sputum of CF Patients.

The rheological properties of sputum samples were measured following incubation of CF sputum with DNase I formulation buffer or different concentrations of plant expressed rh DNase I and Pulmozyme®, diluted in DNase I formulation buffer (final concentration 0.2, 2, 5, 10 and 20 ug/gr sputum) (see FIGS. 12A-12D; 13A-13D; 18A-18D and 19A-19D). DNase I concentrations correspond to the concentrations detected 15 min after aerosolization of Pulmozyme® recommended therapeutic dose (mean value of 2.9 μg/ml mucus).

Time sweep measurement (FIGS. 12A-12D and 13A-13D) clearly revealed that incubation with the plant expressed rh DNase I significantly reduced sputum elastic modulus (FIGS. 12A-12D) and viscous modulus (FIGS. 13A-13D), in a concentration-dependent manner, and with a consistently greater efficiency (per ug DNase I; FIG. 12A) than the clinically approved mammalian cell-expressed Pulmozyme®. Even greater expression of the improved rheological properties of the prh DNase I-treated sputa was observed when the reduction elastic and viscous modulus following incubation with prh DNase I was expressed as percent change compared to the untreated control (see FIGS. 14A and 14B). In addition, stress sweep measurements (see FIGS. 18A-18D and 19A-19D) reveals that the plant expressed rh DNase I disrupts the sputa elastic structure (the internal network of the sputa) in a dose-dependent manner and with greater efficiency than the clinically approved mammalian cell-expressed Pulmozyme®. The improved efficacy of the prh DNase I is consistent with the improved enzyme kinetics and the higher specific activity of the prh DNase I, compared to Pulmozyme® (see Examples 2 and 3 above).

Synergistic Reduction of CF Sputum Rheological Properties with Plant Expressed rh DNase I and Magnesium Time sweep measurements evaluating rheological properties of CF sputum were performed following incubation of sputum samples with plant expressed rh DNase I protein, diluted in DNase I formulation buffer (final concentration of 2 ug/gr sputum), or DNase I formulation buffer (control), in the presence or absence of 25, 50 and 100 mM magnesium chloride, prepared in DNase I formulation buffer. FIGS. 15 and 16 clearly indicate that incubation of sputum with 25-100 mM magnesium chloride (grey bars), or prhDNase alone ("0" $MgCl_2$ in FIGS. 15 and 16) results in reduction in both the sputum elastic (FIG. 15) and viscous (FIG. 16) modulus. When the sputum is incubated with both magnesium chloride and plant expressed rh DNase I, (hatched bars, 25-100 mM $MgCl_2$), a significant synergistic reduction can be observed following a threshold of added Mg (in this experiment 100 mM Mg) in both sputum rheological properties assayed [elastic (FIG. 15) and viscous (FIG. 16) modulus].

Stress sweep measurements were performed following incubation of sputum samples with plant expressed rh DNase I protein, diluted in DNase I formulation buffer, or DNase I formulation buffer (control), in the presence or absence of 100 mM magnesium sulfate, prepared in DNase I formulation buffer (see FIGS. 20A-20C).

Taken together, these results demonstrate that incubation of CF sputum with both magnesium sulfate (FIGS. 20A-20C, grey bars) and prhDNase (FIGS. 20A-20C, dark bars) results in a synergistically greater and more significant disruption in sputum elastic structure than incubation with prhDNase or magnesium sulfate alone. This is particularly evident in patient sample A, FIG. 20A, where reduction in the stress sweep values for sputum sample by prhDNase was detected primarily when magnesium sulfate is added.

Magnesium Salts do not Inhibit Plant Expressed rh DNase I Activity

When catalytic activity of plant expressed rh DNase I was assayed in the presence of different concentrations of magnesium sulfate and magnesium chloride, a dose-dependent improvement of DNA hydrolytic activity was observed with concentrations between 0.5 to 10 mM magnesium, with no difference between activity in the presence of chloride salt ($MgCl_2$) or sulphate salt ($MgSO_4$) (FIG. 16). DNA hydrolytic activity of the plant expressed rh DNase I remained optimal with both magnesium sulfate and magnesium chloride at concentration of 10-50 mM, with only a slight depression of activity with magnesium sulphate, compared to magnesium chloride, at 100 mM. Thus, neither the chloride salt ($MgCl_2$) or sulphate salt ($MgSO_4$) significantly impairs DNA hydrolytic activity of the plant expressed rh DNase I over a wide range of concentrations.

Taken together, these results show that incubation with plant expressed rh DNase I improves the rheological properties of CF sputum. The dose dependent reduction in sputum rheological properties achieved with prh DNase I is more dramatic than that observed with mammalian cell expressed DNae I (Pulmozyme®). Yet further, it was observed that addition of magnesium chloride can improve the effect of plant expressed rh DNase I on the rheological properties of sputum, and that the DNA hydrolytic activity of plant expressed rh DNase I is enhanced by both magnesium chloride and magnesium sulphate over a wide range of concentrations. Thus, magnesium sulfate can be supplemented to prh DNase I to improve the prh DNase Is mucolytic activity in-vivo.

Example 6

Pulmonary Delivery of Plant-Expressed rh Dnase I by Inhalation of Liquid prhDNase I Evaluation of plant-expressed rhDNase I delivery to the lung of Sprague-Dawley rats using a nose-only inhalation exposure system, was conducted with a liquid composition comprising plant expressed rhDNase I.

Materials and Methods

Plant Expressed rhDNase I: The prh DNase I was suspended in formulation buffer (150 mM NaCl, 1 mM $CaCl_2$).

"Nose Only" Inhalation Chamber: Aerosols were generated from a solution of prh DNase I with a Pari LC Plus® compressed air jet nebulizer [PARI nebulizers (PARI GmbH)] with an inlet pressure of 20 psi, and directed into a flow-past-port "nose-only" rodent exposure chamber. The chamber exhaust flow rate was adjusted to a volumetric flow rate of approximately 13 L/min, resulting in the chamber being under slightly negative pressure relative to ambient conditions. The chamber's negative pressure was maintained to ensure adequate air flow for the animals and prevent inadvertent escape of test material from the device.

Aerosol Sampling and Particle Size Analysis: During exposure, the aerosol concentration and particle size were evaluated. The aerosol concentration was determined via collection of a filter sample at the breathing zone of the nose-only exposure system using a controlled vacuum flow. The content of prh DNaseI on the filter was quantified by ELISA, Methyl green (MG) activity assay and DNase Alert-based activity assay as described hereinabove. Aerosol concentration was determined by dividing prh DNase I content by the total volume of air pulled through the filter. The particle size of the prh DNase I aerosol was measured, as above, with a mercer seven stage cascade impactor. Substrates were weighed before and after collection of the impactor. The mass median aerodynamic diameter (MMAD) and geometric standard deviation (GSD) were then calculated.

Animals and Tissue Samples: Adult male Sprague-Dawley rats, 8-10 weeks old and about 200-300 grams each, were used Animals were acclimated (conditioned) to the nose-only exposure tubes for no less than 3 times prior to exposure, with the last conditioning period occurring no more than 3 days prior to the day of exposure.

Conditioning is used to alleviate undue stress during the exposure period. All animals were weighed prior to inhalation exposure and at sacrifice. Lungs were harvested, weighed and removed, lavaged three times with 3 ml of Ca- and Mg-free phosphate buffered saline. Lavage fluid was centrifuged, and the supernatants of each sample were frozen (−70 to −90° C.) until analysis. Following lavage the lungs were snap frozen in liquid nitrogen and maintained frozen at −70 to −90° C. until analysis.

Prh DNase I was administered in a single dose, exposure duration of 60 minutes in the "nose-only" exposure chamber.

Results

No abnormal behavior or health issues were noted in the animals throughout the study period. Animals were exposed to prhDNase I for 60 minutes Immediately post exposure, animals were euthanized and body weights, lung weights, and lavage recoveries documented. No abnormal gross observations were noted at the time of necropsy.

The total aerosol concentration measured, and particle size data are shown below in Tables IX and X.

TABLE IX prhDNase I Aerosol Concentrations (μg/L), evaluated by different quantitation assays

| Assay: | ELISA | Methylgreen | DNase Alert | Average |
|---|---|---|---|---|
| | 34.4 | 31.3 | 29.2 | 31.6 |

TABLE XI

Particle Size Analysis

| MMAD (μm) | GSD |
|---|---|
| 2.02 | 2.33 |

Delivery of prhDNase I to the Lung Following Single Aerosol Inhalation:Lungs and lavage fluid of the rats were analyzed using the ELISA (immunological) and methyl-green activity assay. FIG. 21 shows the total prh DNase I content, representing enzyme recovered from the lungs (diagonal lines) and bronchialveolar lavages BAL1 (black), BAL2 (white) and BAL3 (stippled) for each of the three subject rats. An average of 82.5 μg prhDNase I per kg rat body weight was measured in the lung (lung and lavage fluid) immediately post inhalation exposure.

When the animals were exposed for 60 minutes to prh DNase I aerosols, characterized by MMAD of 2.02 um, GSD of 2.33 and aerosol concentration of 31.6 μg/L, the average amount of prh DNase I recovered in the lung and lavage fluid of the animals was 82.5 μg/kg (FIG. 21 and Table XI).

TABLE XI

Pulmonary Delivery of prh DNase I

| Animal ID | Prh DNase I content in lung and BALF (μg/Kg), as evaluated by ELISA | MG |
|---|---|---|
| 1 | 67.3 | 77.8 |
| 2 | 69.7 | 84.8 |
| 3 | 85.8 | 109.8 |
| Average | 73.4 | 90.8 |

These results provide an indication that liquid formulation of prhDNase I can be reliably delivered as an aerosol by inhalation with no obvious detriment to the subject or to the enzyme's biological activity, and with consistent and accurate targeting of pulmonary airways.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An inhalable pharmaceutical composition for pulmonary administration comprising a human DNase I protein and a physiologically acceptable pharmacologically-inert liquid carrier, wherein said human DNase I protein is a plant expressed recombinant human DNase I protein comprising an N-terminal Glycine residue at position 1 of said human DNase I protein.

2. The inhalable pharmaceutical composition of claim 1, wherein said human DNase I protein comprising an N-terminal Glycine residue at position 1 of said human DNase I protein comprises the amino acid sequence as set forth in SEQ ID NO:6.

3. The inhalable pharmaceutical composition of claim 1, wherein said human DNase I protein comprises the amino acid sequence as set forth in SEQ ID NO:5.

4. The inhalable pharmaceutical composition of claim 1, wherein said human DNase I protein has at least one core α-(1,3) fucose.

5. The inhalable pharmaceutical composition of claim 1, wherein said human DNase I protein has reduced susceptibility to actin inhibition of endonuclease activity as compared with that of mammalian cell expressed human recombinant DNase I.

6. The inhalable pharmaceutical composition of claim 1, further comprising, as an active ingredient, a magnesium salt.

7. The inhalable pharmaceutical composition of claim 1, further comprising, as an active ingredient, an agent for inhibiting formation of G actin and/or enhancing formation of F actin.

8. The inhalable pharmaceutical composition of claim 1, wherein said human DNase I protein is formulated in liposomes.

9. The inhalable pharmaceutical composition of claim 1, wherein said human DNase I protein is at least 90-95% pure human DNase I protein.

10. The inhalable pharmaceutical composition of claim 1, further comprising plant beta-acetylhexosaminidase enzyme protein.

11. The inhalable pharmaceutical composition of claim 9, wherein said plant beta-acetylhexosaminidase enzyme protein is inactivated beta-acetylhexosaminidase enzyme protein.

12. A method of reducing extraceullular DNA in a secretion, fluid or tissue of a subject in need thereof, the method comprising administering to the subject the inhalable pharmaceutical composition of claim 1, thereby reducing extraceullular DNA in the secretion, fluid or tissue of the subject.

13. The method of claim 12, wherein said subject is suffering from a disease or condition selected from the group consisting of male infertility, metastatic cancer, a viral, bacterial, fungal or protozoan infection, sepsis, atherosclerosis, diabetes, delayed type hypersensitivity and a uterine disorder.

14. A method of reducing DNA in a pulmonary secretion or fluid of a subject in need thereof, the method comprising administering to the subject the inhalable pharmaceutical composition of claim 1, thereby reducing DNA in the pulmonary secretion or fluid of the subject.

15. A method of treating a pulmonary disease or condition associated with excess DNA in a pulmonary secretion in a subject in need thereof, the method comprising administering to the subject the inhalable pharmaceutical composition of claim 1, thereby treating the pulmonary disease or condition associated with excess DNA in the pulmonary secretion in the subject.

16. The method of claim 14, wherein said subject is suffering from a respiratory disease selected from the group consisting of acute or chronic bronchopulmonary disease, atelectasis due to tracheal or bronchial impaction, and complications of tracheostomy.

17. The method of claim 16, wherein said acute or chronic bronchopulmonary disease is selected from the group consisting of infectious pneumonia, bronchitis or tracheobronchitis, bronchiectasis, cystic fibrosis, asthma, chronic obstructive pulmonary disease (COPD), TB or fungal infections.

18. The method of claim 15, wherein an effective amount of said inhalable pharmaceutical composition is a single dose of 0.1 to 25 mg DNase I, administered daily.

19. The method of claim 17, wherein an effective amount of said inhalable pharmaceutical composition is a plurality of doses, each dose comprising 1.0-3.0 mg DNase, said doses administered at least twice, 2-3 times, 2-4 times or 2-6 times daily.

* * * * *